US00RE46965E

(19) United States
(12) Reissued Patent
Austad et al.

(10) Patent Number: US RE46,965 E
(45) Date of Reissued Patent: *Jul. 24, 2018

(54) INTERMEDIATES FOR THE PREPARATION OF ANALOGS OF HALICHONDRIN B

(71) Applicant: Eisai R&D Management Co., Ltd., Tokyo (JP)

(72) Inventors: Brian Austad, Tewksbury, MA (US); Charles E. Chase, Londonderry, NH (US); Francis G. Fang, Andover, MA (US); Trevor Calkins, Stoughton, WI (US); Bryan M. Lewis, North Brunswick, NJ (US)

(73) Assignee: Eisai R&D Management Co., Ltd., Tokyo (JP)

( * ) Notice: This patent is subject to a terminal disclaimer.

(21) Appl. No.: 13/924,892

(22) Filed: Jun. 24, 2013

Related U.S. Patent Documents

Reissue of:
(64) Patent No.: 7,982,060
Issued: Jul. 19, 2011
Appl. No.: 11/628,396
PCT Filed: Jun. 3, 2005
PCT No.: PCT/US2005/019669
§ 371 (c)(1),
(2) Date: Mar. 28, 2007
PCT Pub. No.: WO2005/118565
PCT Pub. Date: Dec. 15, 2005

U.S. Applications:
(62) Division of application No. 13/495,909, filed on Jun. 13, 2012, now Pat. No. Re. 45,324, which is an
(Continued)

(51) Int. Cl.

| | |
|---|---|
| ***C07D 307/12*** | (2006.01) |
| ***C07F 7/18*** | (2006.01) |
| ***C07D 407/06*** | (2006.01) |
| ***C07D 407/14*** | (2006.01) |
| ***C07D 493/04*** | (2006.01) |
| ***C07D 493/08*** | (2006.01) |

(Continued)

(52) U.S. Cl.
CPC ..... *C07F 7/1844* (2013.01); *A61K 31/341* (2013.01); *C07C 33/423* (2013.01); *C07D 307/12* (2013.01); *C07D 307/28* (2013.01); *C07D 307/33* (2013.01); *C07D 317/72* (2013.01); *C07D 407/06* (2013.01); *C07D 407/14* (2013.01); *C07D 493/04* (2013.01); *C07D 493/08* (2013.01); *C07D 493/10* (2013.01); *C07D 493/18* (2013.01); *C07D 493/20* (2013.01); *C07D 493/22* (2013.01); *C07F 7/188* (2013.01); *C07F 7/1856* (2013.01); *C07H 15/26* (2013.01); *Y02P 20/55* (2015.11)

(58) Field of Classification Search
CPC ..... C07F 7/1844; C07F 7/188; C07F 7/1856; C07C 33/423; C07D 307/12; C07D 317/72; C07D 493/10; C07D 493/20; C07D 493/22; C07D 493/18; C07D 493/08; C07D 493/04; C07D 407/14; C07D 407/06; C07D 307/33; C07D 307/28; A61K 31/341; C07H 15/26; Y02P 20/55
USPC ..... 514/450; 549/348
See application file for complete search history.

(56) References Cited

U.S. PATENT DOCUMENTS 5,338,865 A 8/1994 Kishi et al.
5,436,238 A 7/1995 Kishi et al.
(Continued)

FOREIGN PATENT DOCUMENTS

EP 0 572 109 A1 12/1993
EP 0572109 12/1993
(Continued)

OTHER PUBLICATIONS

Duan and Kishi, "Synthetic Studies on Halichondrins: A New Practical Synthesis of the C.1-C.12 Segment," *Tetrahedron Lett.* 34(47), pp. 7541-7544 (1993).
(Continued)

*Primary Examiner* — Alan Diamond
(74) *Attorney, Agent, or Firm* — Finnegan, Henderson, Farabow, Garrett & Dunner LLP

(57) ABSTRACT

The present invention provides macrocyclic compounds, synthesis of the same and intermediates thereto. Such compounds, and compositions thereof, are useful for treating or preventing proliferative disorders Formula (F-4).

(F-4)

2 Claims, No Drawings

Related U.S. Application Data application for the reissue of Pat. No. 7,982,060, filed as application No. PCT/US2005/019669 on Jun. 3, 2005.

(60) Provisional application No. 60/576,642, filed on Jun. 3, 2004, provisional application No. 60/626,769, filed on Nov. 10, 2004, provisional application No. 60/663,300, filed on Mar. 18, 2005.

(51) Int. Cl.

| | |
|---|---|
| ***C07D 493/18*** | (2006.01) |
| ***C07D 493/22*** | (2006.01) |
| ***C07D 493/20*** | (2006.01) |
| ***C07D 317/72*** | (2006.01) |
| ***C07H 15/26*** | (2006.01) |
| ***C07C 33/42*** | (2006.01) |
| ***A61K 31/341*** | (2006.01) |
| ***C07D 493/10*** | (2006.01) |
| ***C07D 307/28*** | (2006.01) |
| ***C07D 307/33*** | (2006.01) |

(56) References Cited

U.S. PATENT DOCUMENTS

| | | | | |
|---|---|---|---|---|
| 6,214,865 | B1 | 4/2001 | Littlefield et al. | |
| 6,365,759 | B1 | 4/2002 | Littlefield et al. | |
| 6,469,182 | B1 | 10/2002 | Littlefield et al. | |
| 6,653,341 | B1 | 11/2003 | Littlefield et al. | |
| 7,470,720 | B2 | 12/2008 | Littlefield et al. | |
| 7,982,060 | B2 | 7/2011 | Austad et al. | |
| 8,093,410 | B2 | 1/2012 | Chase et al. | |
| 8,097,648 | B2 | 1/2012 | Littlefield et al. | |
| 8,148,554 | B2 | 4/2012 | Seletsky et al. | |
| 8,203,010 | B2 | 6/2012 | Endo et al. | |
| 8,350,067 | B2 | 1/2013 | Endo et al. | |
| 8,445,701 | B2 | 5/2013 | Austad et al. | |
| 8,598,373 | B2 * | 12/2013 | Hu | C07D 493/22 549/348 |
| 8,618,313 | B2 | 12/2013 | Benayoud et al. | |
| 8,884,031 | B2 | 11/2014 | Chase et al. | |
| RE45,324 | E | 1/2015 | Austad et al. | |
| 8,927,597 | B2 | 1/2015 | Endo et al. | |
| 8,975,422 | B2 | 3/2015 | Fang et al. | |
| 8,987,479 | B2 | 3/2015 | Chase et al. | |
| 9,206,194 | B2 * | 12/2015 | Hu | C07D 493/22 |
| 9,303,039 | B2 * | 4/2016 | Zhang | C07D 493/22 |
| 9,303,050 | B2 | 4/2016 | Benayoud et al. | |
| 9,382,262 | B2 | 7/2016 | Endo et al. | |
| 9,469,651 | B2 | 10/2016 | Hu | |
| 9,604,993 | B2 | 3/2017 | Chase et al. | |
| 9,695,188 | B2 | 7/2017 | Hu et al. | |
| 2004/0198806 | A1 * | 10/2004 | Littlefield et al. | 514/450 |
| 2006/0154312 | A1 | 7/2006 | Agoulnik et al. | |
| 2007/0244187 | A1 | 10/2007 | Austad et al. | |
| 2009/0104285 | A1 | 4/2009 | Littlefield et al. | |
| 2009/0198074 | A1 | 8/2009 | Chase et al. | |
| 2009/0203771 | A1 | 8/2009 | Inanaga et al. | |
| 2010/0190843 | A1 | 7/2010 | Agoulnik et al. | |
| 2011/0054194 | A1 | 3/2011 | Hu | |
| 2011/0172446 | A1 | 7/2011 | Littlefield et al. | |
| 2011/0184190 | A1 | 7/2011 | Endo et al. | |
| 2012/0029213 | A1 | 2/2012 | Austad et al. | |
| 2012/0095242 | A1 | 4/2012 | Chase et al. | |
| 2012/0309988 | A1 | 12/2012 | Austad et al. | |
| 2014/0163095 | A1 | 6/2014 | Kremer et al. | |
| 2016/0214992 | A1 | 7/2016 | Chase et al. | |
| 2016/0264594 | A1 | 9/2016 | Fang et al. | |
| 2016/0376294 | A1 | 12/2016 | Endo et al. | |
| 2017/0071903 | A1 | 3/2017 | Funahashi et al. | |
| 2017/0100367 | A1 | 4/2017 | Asano et al. | |
| 2017/0100368 | A1 | 4/2017 | Cox et al. | |
| 2017/0298078 | A1 | 10/2017 | Hu et al. | |

FOREIGN PATENT DOCUMENTS

| | | | |
|---|---|---|---|
| EP | 0572109 | A1 | 12/1993 |
| JP | 2002-518384 | | 6/2002 |
| JP | 2002-518384 | A | 6/2002 |
| WO | WO 93/17690 | | 9/1993 |
| WO | WO-93/17690 | A1 | 9/1993 |
| WO | WO 99/65894 | | 12/1999 |
| WO | WO-99/65894 | A1 | 12/1999 |
| WO | WO 2004034990 | A2 | 4/2004 |
| WO | WO 2005/118565 | | 12/2005 |
| WO | WO 2005118565 | A1 | 12/2005 |
| WO | WO 2006076100 | A2 | 7/2006 |
| WO | WO 2007061874 | A2 | 5/2007 |
| WO | WO 2009/046308 | | 4/2009 |
| WO | WO-2009/046308 | A1 | 4/2009 |
| WO | WO 2009/064029 | | 5/2009 |
| WO | WO-2009/064029 | A1 | 5/2009 |
| WO | WO 2009/124237 | | 10/2009 |
| WO | WO-2009/124237 | A1 | 10/2009 |
| WO | WO 2011/094339 | | 8/2011 |
| WO | WO-2011/094339 | A1 | 8/2011 |
| WO | WO 2012147900 | A1 | 11/2012 |
| WO | WO 2014087230 | A1 | 6/2014 |
| WO | WO 2015066729 | A1 | 5/2015 |
| WO | WO 2015085193 | A1 | 6/2015 |
| WO | WO 2015134399 | A1 | 9/2015 |
| WO | WO 2015183961 | A1 | 12/2015 |
| WO | WO 2015184145 | A1 | 12/2015 |
| WO | WO 2016141209 | A1 | 9/2016 |
| WO | WO 2016179607 | A1 | 11/2016 |

OTHER PUBLICATIONS

Stamos et al., "A Mild Preparation of Vinyliodides from Vinylsilanes," *Tetrahedron Lett.* 37(48), pp. 8647-8650 (1996).

Communication pursuant to Rule 114(2) EPC from counterpart European Application EP 05760356.5, dated Jul. 4, 2012.

Wan et al., "Asymmetric Ni(II)/Cr(II)-Mediated Coupling Reaction: Stoichiometric Process," *Organic Letters* 4(25), pp. 4431-4434 (2002).

Supporting Information for Wan et al., "Asymmetric Ni(II)/Cr(II)-Mediated Coupling Reaction: Stoichiometric Process," *Organic Letters* 4(25), pp. 4431-4434 (2002).

RN: 546141-26-8; CN: 1,2-Propaneldiol, 3-[(2R,3R,4R,5S)-tetrahydro-3-hydroxy-4-[(phenylsulfony)methyl]-5-(2-propen-1-yl)-2-furanyl]-1,2-dibenzoate, (2S)-; Entered STN: Jul. 11, 2003.

RN: 546141-39-3; CN: 1,2-Propaneldiol, 3-[(2R,3R,4R,5S)-tetrahydro-3-methoxy-4-[(phenylsulfony)methyl]-5-(2-propen-1-yl)-2-furanyl]-,1,2-dibenzoate, (2S); Entered STN: Jul. 11, 2003.

RN: 546141-40-6; CN: 1,2-Propaneldiol, 3-[(2R,3R,4R,5S)-tetrahydro-3-methoxy-4-[(phenylsulfony)methyl]-5-(2-propen-1-yl)-2-furanyl]-, (2S); Entered STN: Jul. 11, 2003.

RN: 185411-09-0; CN: L-arabino-D-allo-Dodeconic acid, 3,7:6,10-dianhydro-8,9-O-cyclohexylidene-2,4,5-trideoxy-, methyl ester; Entered STN: Jan. 28, 1997.

English translation of the Office Action from the Japanese Patent Office for the counterpart Japanese Application No. 2007-515,643, dated Apr. 24, 2012.

English translation of the Office Action from the Japanese Patent Office for the counterpart Japanese Application No. 2007-515,643, dated Aug. 16, 2012.

Takai et al., "Reactions of Alkenylchromium reagents prepared from alkenyl trifluoromethanesulfonates (triflates) with chromium (II) chloride under nickel catalysis," *J. Am. Chem. Soc.* 108, pp. 6048-6050 (1986).

Third Party Observation pursuant to Article 115 EPC relating to counterpart European Application EP 05760356.5, dated Mar. 26, 2012.

Third Party Observation pursuant to Article 115 EPC relating to counterpart European Application EP 05760356.5, dated Jan. 9, 2013.

U.S. Patent and Trademark Office, "Clarification of Criteria for Reissue Error in View of In re Tanaka " dated Aug. 1, 2011.

(56) References Cited

OTHER PUBLICATIONS

File History of U.S. Appl. No. 13/868,641, "Intermediates for the Preparation of Analogs of Halichondrin B," in the name of Farid Benayoud et al., filed Apr. 23, 2013.
Aicher, T.D., et al.; "Synthetic Studies Towards Halichondrins: Synthesis of the C.27-C.38 Segment," Tetrahedron Lett. 33(12): 1549-1552 (1992).
Austad et al,, "Process development of Halaven®: Synthesis of the C14-C35 fragment via iterative Nozaki-Hiyama-Kishi reaction—Williamson ether cyclization," Synlett. 24:327-332 (2013).
Austad et al., "Commercial manufacture of Halaven®: Chemoselective transformations en route to structurally complex macrocyclic ketones," Synlett. 24;333-337 (2013).
Austad et al., "Commercial manufacture of Halaven®: Chemoselective transformations en route to structurally complex macrocyclic ketones," Synlett. 24 (2013). Supporting Information, 13 pages.
Bai et al., "Halichondrin B and Homohalichondrin B, Marine Natural Products Binding in the Vinca Domain to Tubulin. Discovery of Tubulin-based Mechanism of Action by Analysis of Differential Cytotoxicity Data," J. Biol. Chem. 266(24): 15882-15889 (1991).
Burke, S.D., et al., "Enantioselective Synthesis of a Halichondrin B C(20) 'C(36) Precursor," Tetrahedron Lett., 36(39): 7023-7026 (1995).
Burke; S.D., et al., "Synthesis of a C(22)-C(34) Halichondrin B Precursor via Ring Opening—Double Ring Closing Metathesis." J. Org. Chem., 63: 8626-8627 (1998).
Burke, S.D., et al., "Synthesis of a C(22) ' C(34) Halichondrin Precursor via a Double Dioxanone-to-Dihydropyran Rearrangement," Tetrahedron Lett., 32(32): 3961-3964 (1991 ).
Aicher et al., "Total Synthesis of Halichondrin Band Norhalichondrin B," J. Am. Chem. Soc. 114(8): 3162-3164 (1992).
Chen C., et al., "Ni(II)/Cr(II)-Mediated Coupling Reaction: An Asymmetric Process," J. Org. Chem., 60:5386-5387 (1995).
Chase et al., "Process development of Halaven®: Synthesis of the Cl1-C13 fragment from D-(−)-Gulono-1, 4-lactone," Synlett. 24:323-326 (2013).
Choi et al., "Assymrnetric Ni(II)/Cr(II)-Mediated Coupling Reaction: Catalytic Process," Org Lett. 4(25): 4435-4438 (2002).
Cooper, A.J., et al., "Total Synthesis of Halichondrin B from Common Sugars: An F-Ring Intermediate from D-Glucose and Efficient Construction of the C1 to C21 Segment," Tetrahedron Lett., 34(51): 8193-8196 (1993).
Dong, C. et al. "New Syntheses of E7389 C14 ?C35 and Halichondrin C14 ?C38 Building Blocks: Reductive Cyclization and Oxy-Michael Cyclization Approaches" J. Am. Chem. Soc. 131: 15642-15646 (2009).
Duan and Kishi, "Synthetic studies on halichondrins: A new practical synthesis of the C.1-C.12 segment," Tetrahedron Lett. 34(47):7541-7544 (1993).
Flemming et al., "Nitrile Anion Cyclizations," Tetrahedron 58:1-23 (2002).
Hirata et al., "Halchondrins—Antitumor Polyether Macrolides from a Marine Sponge," Pure Appl. Chem. 58(5): 701-710 (1986).
Horita et al., "Synthetic Studies of Halichondrin B, an Antitumor Polyether Macrolide Isolated from a Marine Sponge. 8. Synthesis of the Lactone Part (C1-C36) via Horner-Emmons Coupling Between C1-C15 and C16-C36 Fragments and Yamaguchi Lactonization," Tetrahedron Lett, 38(52): 8965-8968 ( 1997).
Horita, K., et al., "Research on Anti-Tumor Active Site of Marine Source Natural Product, Halichondrin B.," International Congress Series, 1157 (Towards Natural Medicine Research in the 21st Century), 327-336 (1998).
Horita, K., et al., "Synthetic Studies of Halichondrin B, an Antitumor Polyether Macrolide Isolated From a Marine Sponge, 2. Efficient Synthesis of C 16-C26 Fragments via Construction of the D Ring by a Highly Stereocontrolled Iodoetherification," Synlett, 40-43 ( 1994 ).
Horita, K., et al., "Synthetic Studies of Halichondrin B, an Antitumor Polyether Macrolide Isolated from a Marine Sponge, 3. Synthesis of C27-C36 Subunit via Completely Stereoselective C-Glycosylation to the F ring," Synlett, 43-45 (1994).
Horita, K., et al., "Synthetic Studies of Halichondrin B. an Antitumor Polyether Macrolide Isolated from a Marine Sponge. 7. Synthesis of Two C27-C36 Units via Construction of the F ring and Completely Stereoselective C-Glycosylation Using Mixed Lewis Acids," Chem. Pharm. Bull., 45(10): 1558-1572 (1997).
Horita, K., et al., "Synthetic Study of a Highly Antitumorigenic Marine Phytochemical, Halichondrin B," Phytochemicals and Phytopharmaceuticals, Shahihi, F. and Ho, C.-T., Eds., AOCS Press, Champaign, IL, 2000. 386-397.
Jackson et al.. "A Total Synthesis of Norhalichondrin B" Angew. Chem. Int. Ed. 48: 2346-2350 (2009).
Jiang, L., et al., "A Novel Route to the F-Ring of Halichondrin B. Diastereoselection in Pd(O)-Mediated meso and C2 Diol Desymmetrization," Org. Lett., 4(20): 3411-3414 (2002).
Jiang, L., et al., "A Practical Synthesis of the F-Ring of Halichondrin B via Ozonolytic Desymmetrization of a C2-Symmetric Dihydroxycyclohexene," J. Org. Chem., 68: 1150-1153 (2003).
Kim, D. et al. "New Syntheses of E7389 C14?C35 and Halichondrin C14?C38 Building Blocks: Double-Inversion Approach" J. Am. Chem. Soc. 131: 15636-15641 (2009).
Mattocks, "Novel Reactions of Some ?-Acyloxy Acid Chlorides," J. Chem. Soc. 371: 1918-1930 (1964).
Mattocks, "Novel Reactions of Some ?-Acyloxy-acid Halides," J. Chem. Soc. 932: 4840-4845 (1964).
Newman, "Drug Evaluation: Eribulin, a Simplified Ketone Analog of the Tubulin Inhibitor Halichondrin B, for the Potential Treatment of Cancer," Curr. Opin. Invest. Drugs, 8:1057-1066 (2007).
Sakamoto et al., "Stereoselective Ring Expansion via Bicyclooxonium ion. A Novel Approach to Oxocanes," Org. Lett. 4(5):676-678 (2002).
Schreiber, "Hydrogen Transfer from Tertiary Amines to Trifluorcacetic Anhydride." Tetrahedron Lett. 21:1027-1030 (1980).
Stamos et al., "A mild preparation of vinyliodides from vinylsilanes," Tetrahedron Lett. 37(48): 8647-8650 (1996).
Stamos et al., "New Synthetic Route to the C.14-C.38 Segment of Halichondrins," J. Org. Chem. 62:7552-7553(1997).
Stamos et al., "Synthetic Studies on Halichondrins: A Practical Synthesis of the C.1-C.13 Segment" Tetrahedron Lett. 37(48): 8643-8646 (1996).
Stamos, D.P., et al., "Ni(II)/Cr(II)-Mediated Coupling Reaction: Beneficial Effects of 4-Tert-Butylpyridine as an Additive and Development of New and Improved Workup Procedures," Tetrahedron Lett., 38(36): 6355-6358 (1997).
Towle et al. "Halichondrin B Macrocyclic Ketone Analog E7389: Medicinal Chemistry Repair of Lactone Ester Instability Generated During Structural Simplification to Clinical Candidate" Annual Meeting of the American Association for Cancer Research, Apr. 6-1 0. 2002, 5721.
Vahdat et al., "Phase II Study of Eribulin Mesylate, a Halichondrin B Analog, in Patients with Metastatic Breast Cancer Previously Treated with an Anthracycline and a Taxane," J. Clin. Oncol. 27(18): 2964-2961 (2009).
Wan et al., "Asymmetric Ni(II)/Cr(II)-Mediated Coupling Reaction: Stoichiometric Process," Org. Lett. 4(25): 4431-4434 (2002).
Xie, C., et al., "Synthesis of the C20-C26 Building Block of Halichondrins via a Regiospecific and Stereoselective SN2' Reaction," Org. Lett., 4(25):4427-4429 (2002).
Yang et al., "Second Generation Synthesis of C27-C35 Building Block of E7389, a Synthetic Halichondrin Analogue," Org. Lett. 11 (20): 4516-4519 (2009).
Yu et al., New Synthetic Route to the C.14-C.21 Fragment of Halichondrin B, Book of Abstracts, 219th ACS National Meeting, San Francisco, CA, Mar. 26-30, 2000 (2000).
RN 1 85411-09-0 CN L-arabino-D-allo-Dodeconic acid, 3,7:6, 1 0-dianhydro-8,9-0-cyclohaxylidene-2,4,5-trideoxy-, methyl ester Entry Date: Entered STN: Jan. 28, 1997.
RN 546141-26-8 CN 1 ,2 Propanediol, 3-[(2R,3R,4R,5S)-tetrahydro-3-hydroxy-4-[(phenylsulfonyl)methyl]-5-(2-propen-1-yl)-2-furanyl]-, 1,2-dibenzoate, (2S)—Entry Date: Entered STN: Jul. 11, 2003.

(56) References Cited

OTHER PUBLICATIONS

RN 546141-39-3 CN 1 ,2-Propanediol, 3-[(2R,3R,4S,5S)-tetrahydro-3-methoxy-4-[(phenylsulfonyl)methyl]-5-(2-propen-1-yl)-2-furanyl]-, 1,2-dibenzoate, (2S)—Entry Date: Entered STN: Jul. 11, 2003.
RN 546141-40-6 CN 1 ,2-propanediol, 3-[(2R,3R,4S,5S)-tetrahydro-3-methoxy-4-f(phenylsulfonyl)methyl]-5-(2-propen-14)-2-furanvll-, (2S)—ED Entered STN: Jul. 11, 2003.
Wan et al., "Asymmetric Ni(II)/Cr(II)-Mediated Coupling Reaction: Stoichiometric Process," Org. Lett. 4(25): 4431-4434 (2002) Supporting Information, 8 pages.
Written Opinion from International Application No. PCT/US2005/019669, dated Sep. 7, 2005.
Takai et at "Reactions of Alkenylchromium Reagents Prepared from Alkenyl Trifluoromethanesulfonates (Triflates) with Chromium(11) Chloride under Nickel Catalysis" J. Am. Chem. Soc. 1966, 108:6048.
Communication pursuant to Rule 114(2) EPC from counterpart European Application EP 05760356.5, dated Apr. 3, 2012.
Office Action from the Canadian Intellectual Property Office for the counterpart Canadian Application No. 2,567,984, dated Oct. 7, 2011.
English translation of the Office Action from the Japanese Patent Office for the counterpart Japanese Application No. 2007-515,643, dated Sep. 13, 2011.
English translation of the Office Action from the Chinese Patent Office for the counterpart Chinese Application No. 201010236637.2, dated Sep. 16, 2011.
Jerry March, "Advanced Organic Chemistry," 4th Ed., pp. 348-357, John Wiley and Sons, N.Y. (1992).
English translation of the Office Action from the Chinese Patent Office for the counterpart Chinese Application No. 201010236637.2, dated Jul. 4. 2012.
Communication enclosing the Extended European Search Report for European Patent Application No. 12178696,6, dated Oct. 16. 2012.
Sutherland et al., "The Synthesis of 6α- and 6β-Fluoroshikimic Acids," *J. Chem. Soc., Chem. Commun.* 18:1386-1387, 1989.
Greene et al., "Protective Groups in Organic Synthesis," John Wiley & Sons, Inc., New York, Third Edition, pp. 24, 127, 128, 134, 142, 170,207,209,215, and 216 (1999).
March, "Advanced Organic Chemistry," John Wiley & Sons, New York, Fourth Edition, pp. 386-388 (1992).
Carruthers et al., "Modern Methods of Organic Synthesis," Cambridge University Press, Cambridge, Fourth Edition, p. 65 (2004).
Ritter, "Synthetic Transformations of Vinyl and Aryl Triflates," *Synthesis* 8:735-762, 1993.
Nicolaou et al., "Total Synthesis of the CP Moiecules CP-263, 114 and CP-225,917—Part 1. Synthesis of Key Intermediates and Intelligence Gathering," *Angew. Chem. Int. Ed.* 38:1669-1675, 1999.
Nicolaou et al., "Total Synthesis of Brevetoxin A: Part 3: Construction of GHIJ and BCDE Ring Systems," *Chem. Eur. J.* 5:628-645, 1999.
The AkzoNobel Technical Bulletin. "Diisobutylaluminum hydride (DIBAL-H) and Other Isobutyl Aluminum Alkyls (DIBAL-BOT, TIBAL) as Specialty Organic Synthesis Reagents," 14 pages (2006).
Wang et al., "Facile preparation of peracetates and per-3-bromobenzoates of alpha-mono- and disaccharides," *Molecules* 1 0:1325-1334, 2005.
Youssefyeh, "Acylatrons of Ketals and Errol Ethers,"*J. Am. Chem. Soc.,* 85:3901-3902, 1963.
Ph.D. Thesis of Thomas Daniel Aicher, "Synthetic Studies towards Halichondrin B," Chapter 4, pp. 35-54, 1990.
First Examination Report from the India Patent Office for the counterpart India Application No. 4812/CHENP/2006 dated Oct. 12, 2012.
Written Amendment and Written Argument filed in the Japanese Patent Office for the counterpart Japanese Application No. 2007-515,643dated Feb. 4, 2013.
Communication pursuant to Article 94(3)PEC from the European Patent Office for the counterpart EP Application No. 12178696.6 dated Aug. 8, 2013.
Notification of Grounds for Rejection from the South Korea Patent Office for the counterpart South Korean Application No. 10-2007-7000085 dated Jun. 30, 2013.
Response to Office Action filed in the European Patent Office for the counterpart EP Application No. 05760356.5 dated Sep. 12, 2013,
Result of Consultation from the European Patent Office for the counterpart EP Application No. 05760356.5 dated Oct. 16, 2013.
Written Submissions filed in the from the European Patent Office for the counterpart EP Application No. 05760356.5 dated Oct. 21, 2013.
Notice of Oral Proceedings from the European Patent Office scheduling Oral Proceedings on Nov. 21, 2013, for the counterpart EP Application No. 05760356.5 dated Oct. 29, 2013.
Supporting Information for Choi, Hyeong-Wook, et al., Asymmetric Ni(II)/Cr(II)-Mediated Coupling Reaction: CaLatytic Process, Organic Letters, vol. 4, No. 25, pp. 1-8 (2002).
Namba, K., et al., "New Catalytic Cycle for Couplings of Aldehydes with Organochromium Reagents", Organic Letters., vol. 6, No. 26, pp. 5031-5033 (2004).
Supporting information for Kurosu, M., et al., "Fe/Cr- and Co/Cr-Mediated Catalytic Asymmetric 2-Haloallylations of Aldehydes", Journal of the American Chemical Society, vol. 126, No. 39, pp. S-1-5-9, (2004).
Communication enclosing the extended European search report for European Patent Application No. 15159875.2, dated Oct. 12, 2015 (7 pages).
Choi et al., "Synthetic Studies on the Marine Natural Product Halichondrins," Pure Appl. Chem. 75:1-17, 2003.
International Preliminary Report on Patentability from International Application No. PCT/US2005/019669, issued Dec. 4, 2006.
International Search Report from International Application No. PCT/US2005/019669 dated Aug. 29, 2005 (date of completion of search) and Sep. 7, 2005 (date of mailing of report).
Written Opinion from International Application No. PCT/US2005/019669, mailed Sep. 7, 2005.
Anderson, "Developing Processes for Crystallization-Induced Asymmetric Transformation," *Org. Process. Res. Dev. 9*: 800-813 (2005).
Bernet et al., "Carbocyclische Verbindungen aus Monosacchariden. Umsetzungen in der Glucosereihe," *Helv. Chim. Acta.* 62: 1990-2016 (1979).
Blanchette et al., "Horner-Wadsworth-Emmons Reaction: Use of Lithium Chloride and an Amine for Base-Sensitive Compounds," *Tetrahedron Lett.* 25(21): 2183-2186 (1984).
Burke, S.D., et al., "Synthetic Studies Toward Complex Polyether Macrolides of Marine Origin," *Spec. Publ. R. Soc. Chem.,* 198: (Anti-Infectives), 73-85 (1997).
Choi et al., "Synthetic Studies on the Marine Natural Product Halichondrins," *Pure Appl. Chem.* 75(1): 1-17 (2003).
Hirata et al., "Halichondrins—Antitumor Polyether Macrolides from a Marine Sponge," *Pure Appl. Chem.* 58(5): 701-710 (1986).
Hori et al., "Efficient Synthesis of 2,3-*trans*-Tetrahydropyrans and Oxepanes: Rearrangement-Ring Expansion of Cyclic Ethers Having a Chloromethanesulfonate," *Tetrahedron Lett.* 40: 2145-2148 (1999).
Horita et al., "Synthetic Studies of Halichondrin B, an Antitumor Polymer Macrolide Isolated from a Marine Sponge. 8. Synthesis of the Lactone Part (C1-C36) via Horner-Emmons Coupling Between C1-C15 and C16-C36 Fragments and Yamaguchi Lactonization," *Tetrahedron Lett.* 38(52): 8965-8968 (1997).
Horita, K., et al., "Synthetic Studies on Halichondrin B, an Antitumor Polyether Macrolide Isolated from a Marine Sponge. 9. Synthesis of the C16-C36 unit via Stereoselective Construction of the D and E Rings," *Chem. Pharm. Bull.,* 46(8): 1199-1216 (1998).
Jackson et al., "The Halichondrins and E7389," *Chem. Rev.* 109: 3044-3079 (2009).

(56) References Cited

OTHER PUBLICATIONS

Kurosu et al., "Fe/Cr- and Co/Cr-Mediated Catalytic Asymmetric 2-Haloallylations of Aldehydes," *J. Am. Chem. Soc.* 126: 12248-12249 (2004).
Mitsunobu, "The Use of Diethyl Azodicarboxylate and Triphenylphosphine in Synthesis and Transformation of Natural Products," *Synthesis.* 1-28 (1981).
Tokunaga et al., "Asymmetric Catalysis with Water: Efficient Kinetic Resolution of Terminal Epoxides by Means of Catalytic Hydrolysis," *Science* 277: 936-938 (1997).
Uemura et al., "Norhalichondrin A: An Antitumor Polyether Macrolide from a Marine Sponge," *J. Am. Chem. Soc.* 107: 4796-4798 (1985).
Yu et al., *Anticancer Agents from Natural Products;* CRC Press: Boca Raton, FL, 241-265. (2005).
Zheng et al., "Macrocyclic Ketone Analogues of Halichondrin B," *Bioorg. Med. Chem. Lett.* 14: 5551-5554 (2004).
Zheng, W. et al. "Synthetic macrocyclic ketone analogs of halichondrin B: structure-activity relationships" American Association for Cancer Research, San Francisco, CA Apr. 1-5, 2000, 1915.
Alley et al. "Comparison of the Relative Efficacies and Toxicities of Halichondrin B Analogues" *Proceedings of the AACR-NCI-EORTC Conference on Molecular Targets and Cancer Therapeutics,* Nov. 14-18, 2005, C230, p. 257.
Dabybeen et al. "Comparison of the Activities of the Truncated Halichondrin B Analog NSC 707389 (E7389) with Those of the Parent Compound and a Proposed Binding Site on Tubulin" *Molecular Pharmacology* 2006, 70:1866.
Seletsky et al. "Structurally simplified macrolactone analogues of halichondrin B" *Bioorg. Med. Chem. Lett.* 14:5547 (2004).
Towle et al. "In Vitro and In Vivo Anticancer Activities of Synthetic Macrocyclic Ketone Analogues of Halichondrin B" *Cancer Research* 2001, 61:1013.
Wang et al. "Structure-Activity Relationships of Halichondrin B Analogues: Modifications at C.30-C.38" *Bioorg. Med. Chem. Lett.* 2000, 10:1029.

* cited by examiner

INTERMEDIATES FOR THE PREPARATION OF ANALOGS OF HALICHONDRIN B

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

[This application claims priority under 35 U.S.C. §371 from international application PCT/US05/019669, filed Jun. 3, 2005, which claims priority to U.S. Provisional Patent Applications 60/576,642, filed Jun. 3, 2004, 60/626,769, filed Nov. 10, 2004, and 60/663,300, filed Mar. 18, 2005, the entire contents of each of which are hereby incorporated herein by reference.] *Notice: More than one reissue application has been filed for the reissue of U.S. Pat. No. 7,982,060. The reissue applications are Reissue application. Ser. No. 13/495,909, and the present application filed herewith. This application is a divisional reissue application of U.S. patent application Ser. No. 13/495,909, filed Jun. 13, 2012, which is a broadening reissue of U.S. Pat. No. 7,982,960, issued on Jul. 19, 2011, from U.S. patent application Ser. No. 11/628,396, which is the National Stage Entry of International Application No. PCT/US2005/019669, filed Jun. 3, 2005, which claims the benefit of priority of U.S. Provisional Application No. 60/576,642, filed on Jun. 3, 2004, U.S. Provisional Application No. 60/626,769, filed on Nov. 10, 2004, and U.S. Provisional Application No. 60/663,300, filed on Mar. 18, 2005, all of which are incorporated herein by reference in their entirety.*

TECHNICAL FIELD OF INVENTION

The present invention relates to compounds useful as intermediates in the synthesis of pharmaceutically active macrolide compounds.

BACKGROUND OF THE INVENTION

The invention relates to pharmaceutically active macrolides, synthesis thereof and intermediates thereto. Halichondrin B is a potent anticancer agent originally isolated from the marine sponge Halichondria okadai, and subsequently found in Axinella sp., Phakellia carteri, and Lissondendryx sp. A total synthesis of Halichondrin B was published in 1992 (Aicher, T. D. et al., J. Am. Chem. Soc. 114: 3162-3164). Halichondrin B has demonstrated in vitro inhibition of tubulin polymerization, microtubule assembly, beta$^{s}$-tubulin crosslinking, GTP and vinblastine binding to tubulin, and tubulin-dependent GTP hydrolysis and has shown in vitro and in vivo anti-cancer properties. Accordingly, there is a need to develop synthetic methods for preparing analogs of Halichondrin B useful as anti-cancer agents.

SUMMARY OF THE INVENTION

As described herein, the present invention provides methods for preparing analogs of Halichondrin B having pharmaceutical activity, such as anticancer or antimitotic (mitosis-blocking) activity. These compounds include a compound of formula B-1939:

B-1939

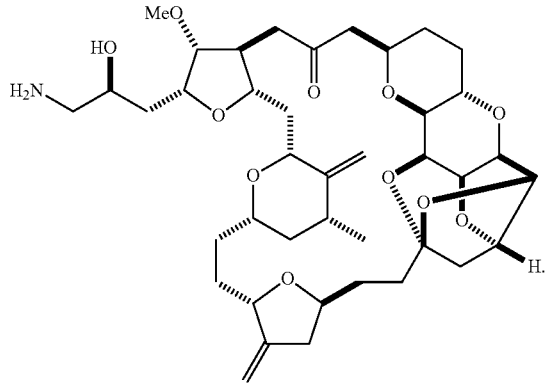

These compounds are useful for treating cancer and other proliferative disorders including, but not limited to, melanoma, fibrosarcoma, leukemia, colon carcinoma, ovarian carcinoma, breast carcinoma, osteosarcoma, prostate carcinoma, and lung carcinoma. The present invention also provides synthetic intermediates useful for preparing said analogs of Halichondrin B.

DETAILED DESCRIPTION OF CERTAIN EMBODIMENTS OF THE INVENTION

The methods and intermediates of the present invention are useful for preparing various analogs of Halichondrin B as described in, e.g. U.S. Pat. No. 6,365,759 and U.S. Pat. No. 6,469,182 the entirety of which are incorporated herein by reference. These Halichondrin B analogs are prepared generally by the assembly of three fragments F-1, F-2, and F-3, as shown by Scheme I below:

Scheme I

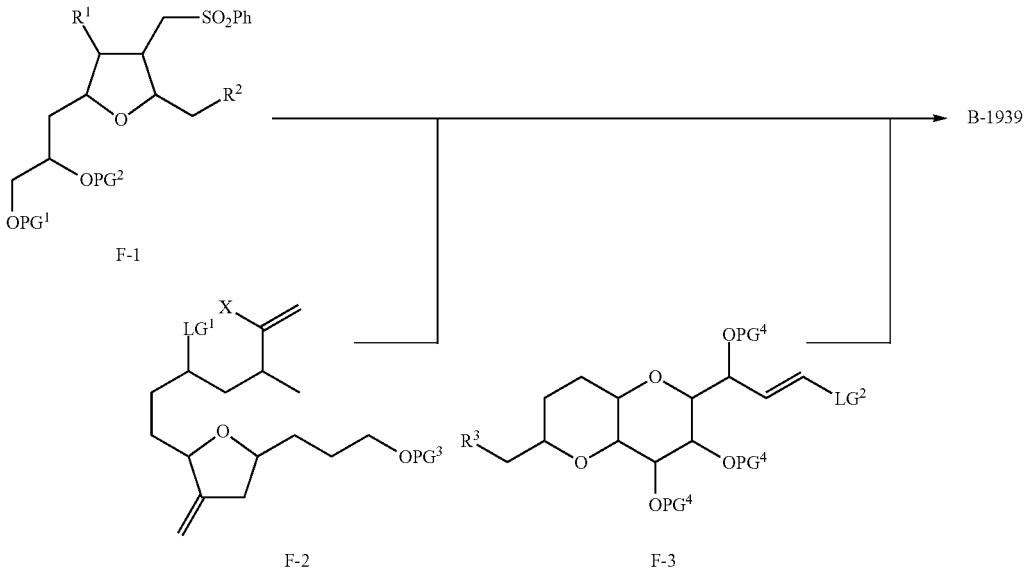

1. Fragment F-1

According to one embodiment, the present invention provides a compound F-1:

F-1

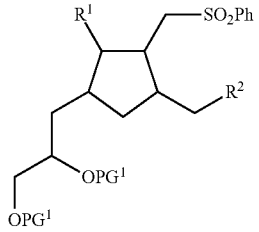

wherein:

each of $PG^1$ and $PG^2$ is independently hydrogen or a suitable hydroxyl protecting group;

$R^1$ is R or OR;

$R^2$ is CHO or —CH═$CH_2$; and each R is independently hydrogen, $C_{1-4}$ haloaliphatic, benzyl, or $C_{1-4}$ aliphatic, provided that when $R^1$ is OMe then $PG^1$ and $PG^2$ do not form an acetonide group.

In certain embodiments, $R^1$ is OR. In other embodiments, $R^1$ is OR wherein R is hydrogen, methyl, or benzyl.

In certain embodiments, $PG^1$ and $PG^2$ are hydrogen. In other embodiments, one of $PG^1$ and $PG^2$ is hydrogen.

Suitable hydroxyl protecting groups are well known in the art and include those described in detail in Protecting Groups in Organic Synthesis, T. W. Greene and P. G. M. Wuts, 3rd edition, John Wiley & Sons, 1999, the entirety of which is incorporated herein by reference. In certain embodiments, each of $PG^1$ and $PG^2$, taken with the oxygen atom to which it is bound, is independently selected from esters, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetyl), crotonate, 4-methoxy-crotonate, benzoate, p-benzylbenzoate, 2,4,6-trimethylbenzoate, or carbonates such as methyl, 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyranyl ethers. Examples of arylalkyl ethers include benzyl, p-methoxybenzyl (MPM), 3,4-dimethoxybenzyl, o-nitrobenzyl, p-nitrobenzyl, p-halobenzyl, 2,6-dichlorobenzyl, p-cyanobenzyl, 2- and 4-picolyl.

In certain embodiments, one or both of the $PG^1$ and $PG^2$ moieties of F-1 are silyl ethers or arylalkyl ethers. In yet other embodiments, one or both of the $PG^1$ and $PG^2$ moieties of F-1 are t-butyldimethylsilyl or benzoyl. In still other embodiments, both of the $PG^1$ and $PG^2$ moieties of F-1 are t-butyldimethylsilyl.

According to an alternate embodiment, $PG^1$ and $PG^2$ are taken together, with the oxygen atoms to which they are bound, to form a diol protecting group, such as a cyclic acetal or ketal. Such groups include methylene, ethylidene, benzylidene, isopropylidene, cyclohexylidene, and cyclopentylidene, a silylene derivative such as di-t-butylsilylene and a 1,1,3,3-tetraisopropyldisiloxanylidene derivative, a cyclic carbonate, and a cyclic boronate. Methods of adding and removing such hydroxyl protecting groups, and additional protecting groups, are well-known in the art and available, for example, in P. J. Kocienski, Protecting Groups, Thieme, 1994, and in T. W. Greene and P. G. M. Wuts, Protective Groups in Organic Synthesis, 3rd edition, John Wiley & Sons, 1999. According to another embodiment, $PG^1$ and $PG^2$ are taken together to form an acetonide group.

According to one embodiment, $R^2$ is CHO.

According to another embodiment, $R^2$ is —CH═$CH_2$.

In certain embodiments, the present invention provides a compound of formula F-1 having the stereochemistry depicted in compound F-1':

F-1'

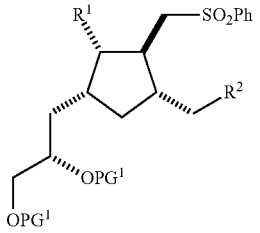

wherein each variable is as defined above and described in classes and subclasses above and herein.

In certain embodiments, the following compounds F-1a and F-1b are provided:

F-1a

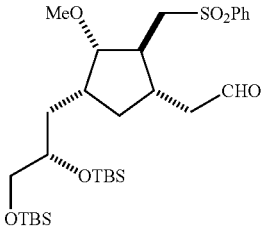

F-1b

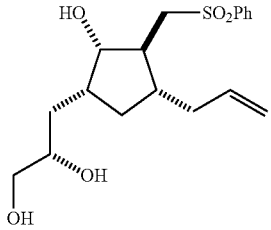

wherein "TBS" refers to t-butyldimethylsilyl.

Details of the syntheses of F-1a and F-1b are set forth in the Examples infra.

2. Fragment F-2

According to another embodiment, the present invention provides a compound F-2:

F-2

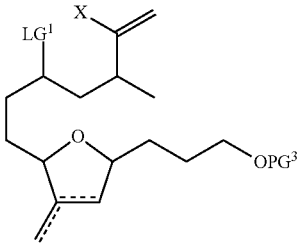

wherein:

each ═ is independently a single or double bond, provided that both ═ groups are not simultaneously a double bond;

$LG^1$ is a suitable leaving group;

X is halogen or —$OSO_2(R^y)$;

$R^y$ is $C_{1-6}$ aliphatic or a 5-7 membered saturated, partially unsaturated, or fully unsaturated ring, wherein $R^y$ is optionally substituted with up to 3 groups selected from halogen, R, $NO_2$, CN, OR, SR, or $N(R)_2$;

each R is independently hydrogen, $C_{1-4}$ haloaliphatic, or $C_{1-4}$ aliphatic; and $PG^3$ is a suitable hydroxyl protecting group.

As used herein, a suitable leaving group is a chemical moiety that is readily displaced by a desired incoming chemical moiety. Suitable leaving groups are well known in the art, e.g., see, "Advanced Organic Chemistry," Jerry March, $4^{th}$ Ed., pp. 351-357, John Wiley and Sons, N.Y. (1992). Such leaving groups include, but are not limited to, halogen, alkoxy, sulphonyloxy, optionally substituted alkylsulphonyloxy, optionally substituted alkenylsulfonyloxy, optionally substituted arylsulfonyloxy, and diazonium moieties. Examples of suitable leaving groups include chloro, iodo, bromo, fluoro, methanesulfonyloxy (mesyloxy), tosyloxy, triflate, nitro-phenylsulfonyloxy (nosyloxy), and bromo-phenylsulfonyloxy (brosyloxy). In certain embodiments, the $LG^1$ moiety of F-2 is sulphonyloxy, optionally substituted alkylsulphonyloxy, optionally substituted alkenylsulfonyloxy, or optionally substituted arylsulfonyloxy. In other embodiments, the $LG^1$ moiety of F-2 is optionally substituted alkylsulphonyloxy. In yet other embodiments, the $LG^1$ moiety of F-2 is mesyloxy or tosyloxy.

In certain embodiments, the X moiety of F-2 is halogen. In other embodiments, the X moiety of F-2 is sulphonyloxy, optionally substituted alkylsulphonyloxy, optionally substituted alkenylsulfonyloxy, or optionally substituted arylsulfonyloxy. In still other embodiments, the X moiety of F-2 is triflate.

In certain embodiments, the $PG^3$ moiety of F-2, taken with the oxygen atom to which it is bound, is a silyl ether. In other embodiments, the $PG^3$ moiety of F-2, taken with the oxygen atom to which it is bound, is an ester group. According to one aspect of the present invention, the $PG^3$ moiety of F-2 is t-butyldimethylsilyl. According to another aspect of the present invention, the $PG^3$ moiety of F-2 is pivaloyl or benzoyl.

In certain embodiments, the present invention provides a compound of formula F-2 having the stereochemistry depicted in formula F-2':

F-2'

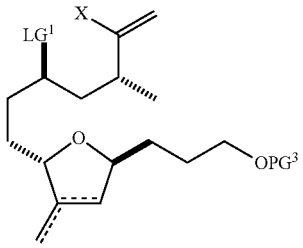

wherein each variable is as defined above and described in classes and subclasses above and herein.

In certain embodiments, a compound F-2a or F-2b is provided:

F-2a

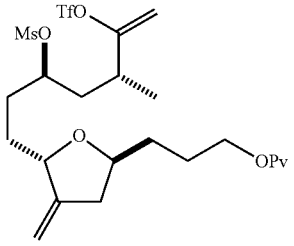

F-2b

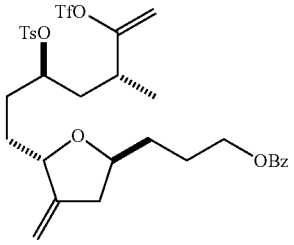

wherein "MsO" refers to mesylate, "TfO" refers to triflate, "OPv" refers to pivaloate, "OBz" refers to benzoate, and "TSO" refers to tosylate.

In other embodiments, the present invention provides a compound of formula F-2b wherein said compound is crystalline. According to another embodiment, a compound of formula F-2b is provided wherein said compound is crystallized from an alkane solvent. In certain embodiments, crystalline F-2b is provided wherein said compound is crystallized from pentane or heptane. In other embodiments, crystalline F-2b is provided wherein said compound is crystallized at about 0° C.

Compounds of formula F-2 are prepared generally from intermediates F-2d and F-2e as shown in Scheme A below.

Scheme A

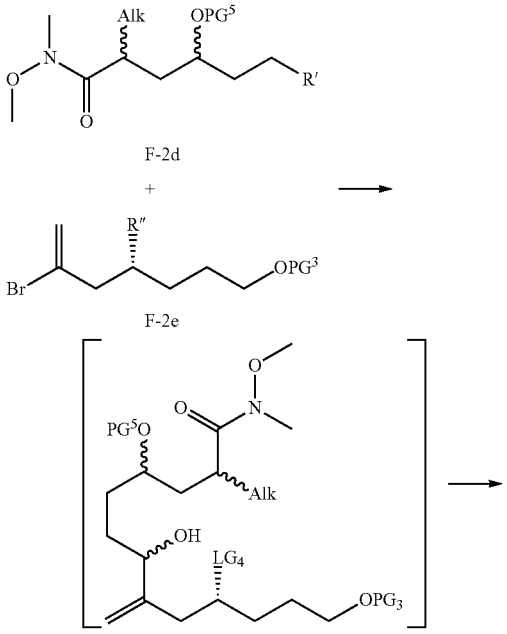

-continued

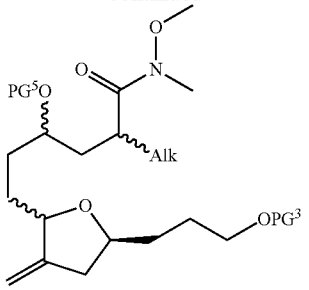

F-2

Accordingly, another aspect of the present invention provides a compound of formula F-2d:

F-2d

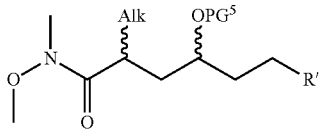

wherein:

R' is —CH═$CH_2$ or —C(O)H;

Alk is a $C_{1-4}$ straight or branched aliphatic group; and $PG^5$ is a suitable hydroxyl protecting group.

Suitable hydroxyl protecting group $PG^5$ is as described and defined for the $PG^3$ moiety of compound F-2, supra. In certain embodiments, $PG^5$, taken with the oxygen atom to which it is bound, is a silyl ether. In other embodiments, $PG^5$ is t-butyldimethylsilyl.

According to one embodiment, the Alk moiety of compound F-2d is methyl.

In certain embodiments, a compound of formula F-2d' is provided:

F-2d'

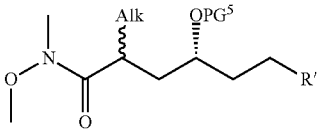

Yet another aspect of the present invention provides a compound of formula F-2e:

F-2e

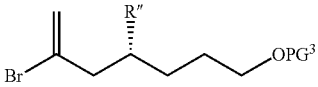

wherein:

R" is OH, $OPG^3$, or $LG^4$;

$LG^4$ is a suitable leaving group; and each $PG^3$ is independently a suitable hydroxyl protecting group, provided that R" is other than OMs when $PG^3$ is t-butyldiphenylsilyl.

One of ordinary skill in the art would recognize that the R" moiety of compound F-2e may be transformed from OH to a protected hydroxyl group, $OPG^3$, or, alternatively, directly to $LG^4$. Such transformations are known to one skilled in the art and include, among others, those described herein. In certain embodiments, R" is OH or $LG^4$. The $LG^4$ leaving group of formula F-2e is as described and defined for the $LG^1$ moiety of compound F-2, supra. In certain embodiments, $LG^4$ is tosyloxy or mesyloxy.

The $PG^3$ moiety of compound F-2e is as defined and described for the $PG^3$ moiety of compound F-2, supra. In certain embodiments, $PG^3$, taken with the oxygen atom to which it is bound, is a silyl ether. In other embodiments, $PG^3$ is t-butyldiphenylsilyl.

Still another aspect of the present invention provides a compound F-2f:

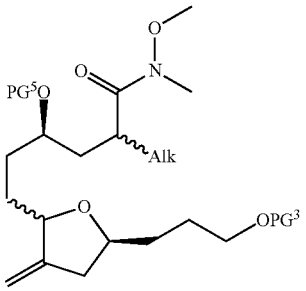

F-2f wherein Alk, $PG^3$ and $PG^5$ are as defined generally and in classes and subclasses described above and herein. Compounds of formula F-2f are used to prepare compounds of formula F-2 by methods described herein and those known in the art.

Details of the synthesis of F-2a are set forth in the Examples infra.

Alternatively, compounds of formula F-2 are prepared from D-quinic acid as shown by Scheme II below. Details of the preparation of compounds of formula F-2 are set forth in the Examples infra.

Scheme II

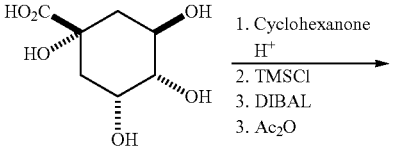

1. D-quinic acid

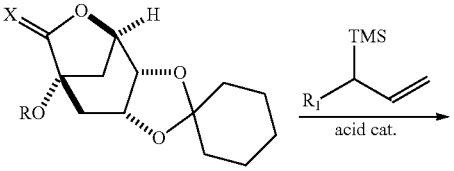

2. X = O, R = H
3. X = O, R = TMS
4. X = H, OH, R = TMS
5. X = H, OAc, R = Ac

-continued

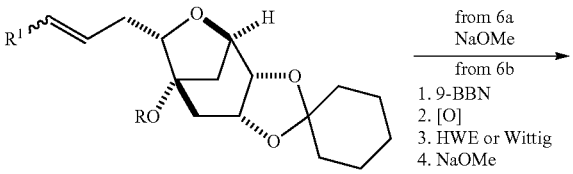

6a. R = Ac, $R^1 = CH_2CO_2R^2$
$R^2$ = alkyl
6b. R = Ac, $R^1$ = H

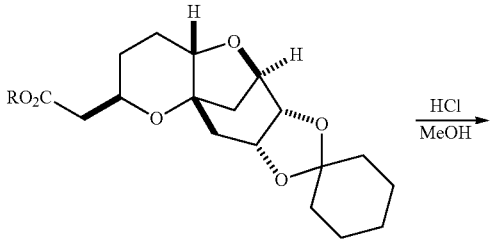

7. R = alkyl

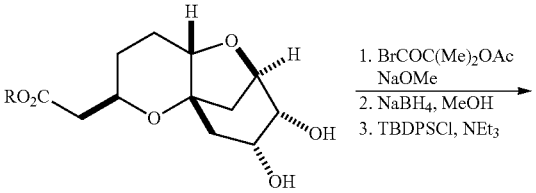

8. R = alkyl

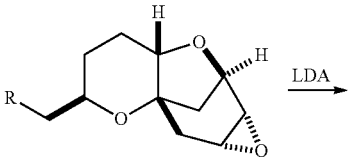

9. R = $CO_2R^1$
$R^1$ = alkyl or H
10. R = $CH_2OH$
11. R = $CH_2OTBDPS$

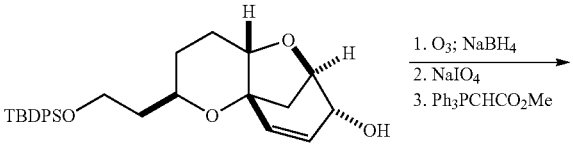

12

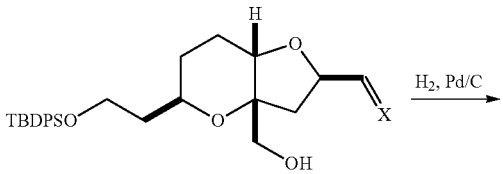

13. X = OH, $CH_2OH$
14. X = O
15. X = $CHCO_2Me$

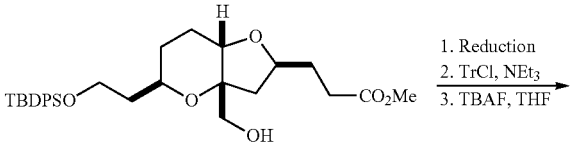

16

-continued

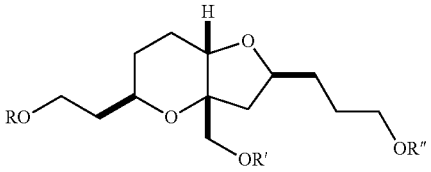

1. NIS, $PPh_3$
2. KCN, $EtOH/H_2O$

17. R = TBDPS, R′ = R″ = H
18. R = TBDPS, R′ = H, R″ = Tr
19. R = R′ = H, R″ = Tr

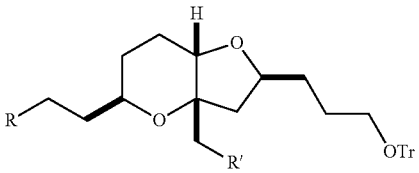

1. Zn, EtOH
2. LDA; MeI

20. R = R′ = I
21. R = CN, R′ = I

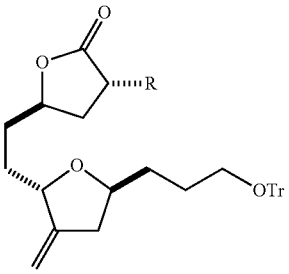

1. HN(OMe)Me
$AlMe_3$
2. TBSCl

22. R = H
23. R = Me

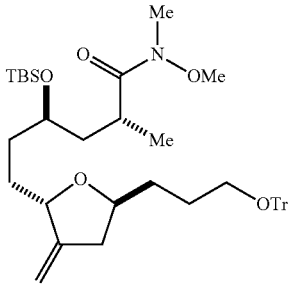

1. MeMgBr
2. LDA, NPTf
3. HCl, IPA

24

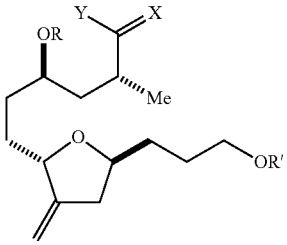

25. X = O, Y = Me, R = TBS, R′ = Tr
26. X = $CH_2$, Y = OTf, R = TBS, R′ = Tr
27. X = $CH_2$, Y = OTf, R = R′ = H

Yet another method for preparing compounds of formula F-2 from D-quinic acid provides an alternative route from intermediate 12 to intermediate 17 as shown in Scheme III below.

Scheme III

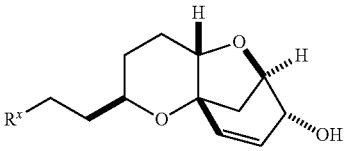

epoxide formation

12

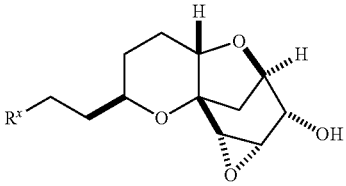

oxidation

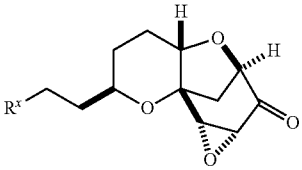

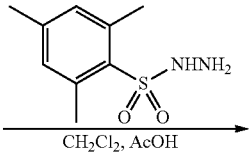

$CH_2Cl_2$, AcOH

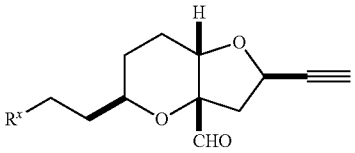

$NaBH_4$
EtOH

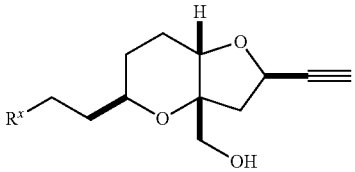

EtMgBr or BuLi
$CH_2O$

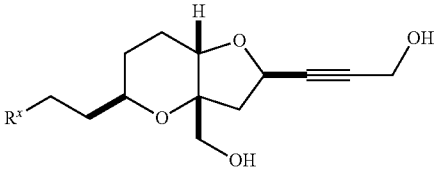

$H_2$, Pd/C
EtOH

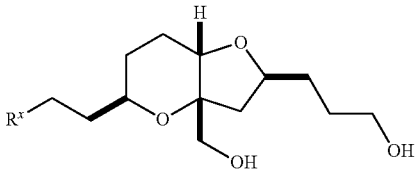

17

Scheme III above shows an alternate method for preparing intermediate 17 from intermediate 12 via Eschenmoser-Tanabe Fragmentation, wherein each [Rx] $R^x$ is independently $OPG^x$ or CN wherein $PG^x$ is a suitable hydroxyl protecting group as described herein. Intermediate 17 is then used to prepare compounds of formula F-2 according to Scheme II above.

Still another method for preparing compounds of formula F-2 from D-quinic acid provides an alternative route from intermediate 9 to intermediate 17 as shown in Scheme IV below.

Scheme IV

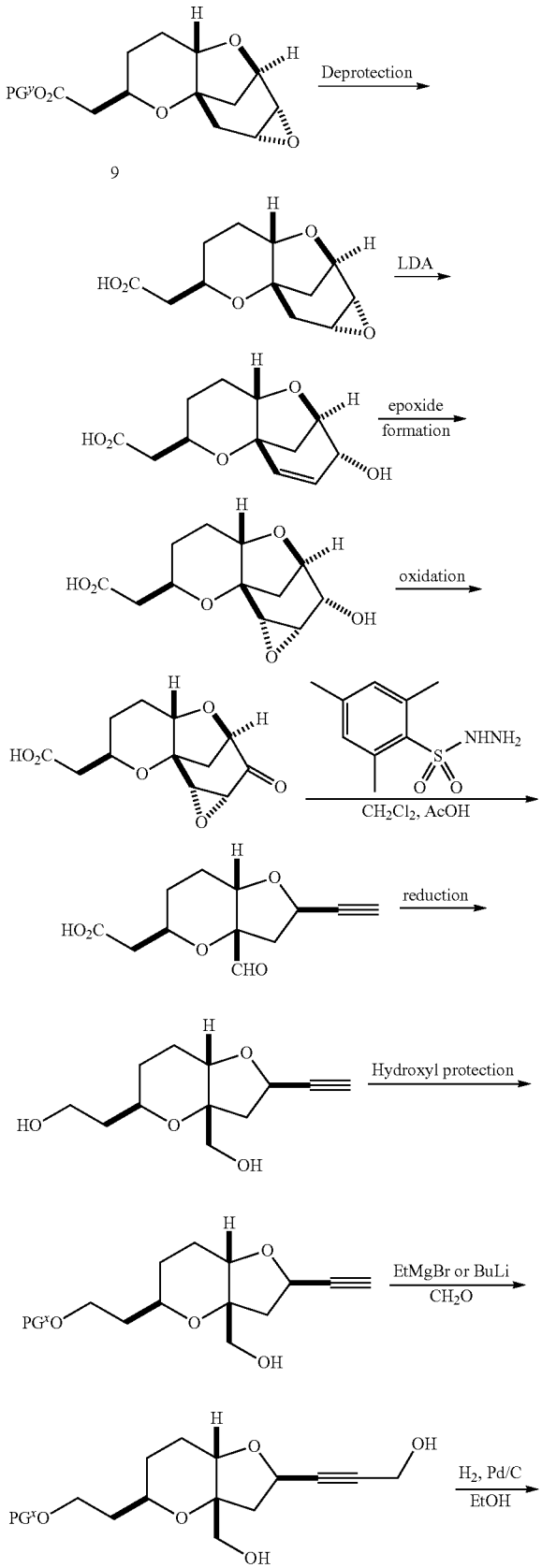

-continued

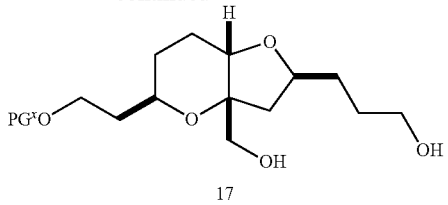

17 wherein $PG^y$ is a suitable carboxyl protecting group, as described herein, and each $PG^x$ is independently a suitable hydroxyl protecting group as described herein.

Yet another method for preparing intermediates useful for preparing compounds of formula F-2 from D-quinic acid is shown in Scheme V below.

Scheme V

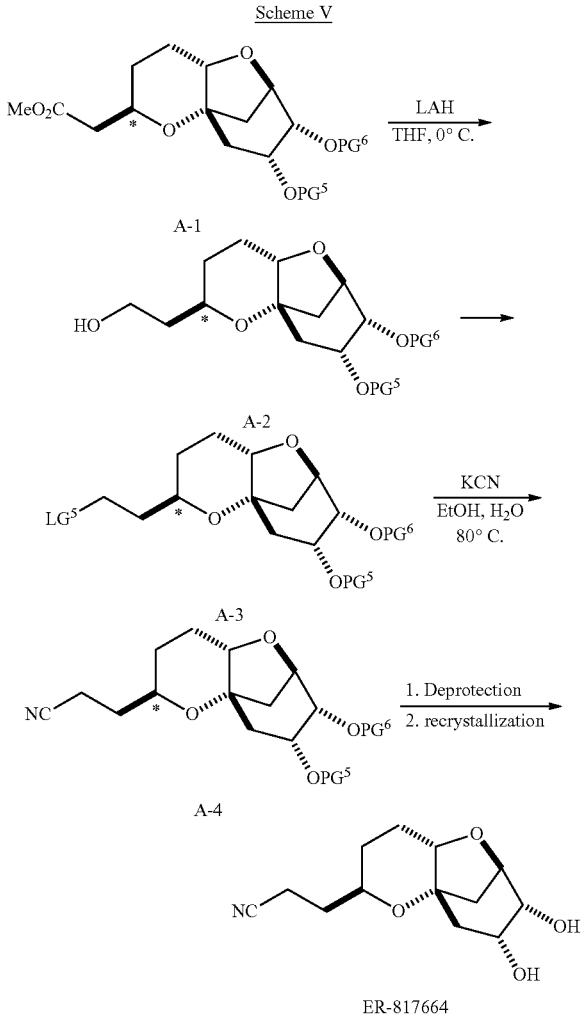

In Scheme V above, intermediate 7 (from Scheme II), wherein R is a methyl ester, is used to prepare ER-817664 as a crystalline intermediate. As depicted in Scheme V above, each $PG^5$ and $PG^6$ is independently a suitable hydroxyl protecting group. In certain embodiments, $PG^5$ and $PG^6$ are taken together to form a cyclic diol protecting group. In other embodiments, $PG^5$ and $PG^6$ are taken together to form a cyclohexylidene protecting group. As depicted in Scheme V above, $LG^5$ is a suitable leaving group. Such suitable leaving groups are well known in the art and include those described herein. In certain embodiments, $LG^5$ is mesyloxy or tosyloxy.

According to another embodiment, the present invention provides a compound of formula A:

A

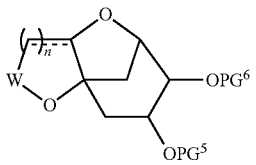

wherein:

═══ designates a single or double bond;

n is 1, 2, or 3;

each of $PG^5$ and $PG^6$ is independently a suitable hydroxyl protecting group;

W is CH-A or C(O);

A is a $C_{1-6}$ aliphatic group, wherein A is optionally substituted with one or more $Q^1$ groups;

each $Q^1$ is independently selected from cyano, halo, azido, oxo, OR, SR, $SO_2R$, $OSO_2R$, $N(R)_2$, NR(CO)R, NR(CO)(CO)R, $NR(CO)N(R)_2$, NR(CO)OR, (CO)OR, O(CO)R, $(CO)N(R)_2$, $O(CO)N(R)_2$, or $OPG^1$, wherein $PG^1$ is a suitable hydroxyl protecting group, and wherein:

two $Q^1$ on A are optionally taken together to form a 3-8 membered saturated, partially unsaturated, or aryl ring having 0-4 heteroatoms independently selected from nitrogen, oxygen, or sulfur; and each R is independently selected from hydrogen or an optionally substituted group selected from $C_{1-6}$ aliphatic, a 5-10 membered saturated, partially unsaturated or aryl carbocyclic ring, or a 4-10 membered saturated, partially unsaturated or aryl ring having 0-4 heteroatoms independently selected from nitrogen, oxygen, or sulfur, wherein:

two R groups on the same nitrogen atom are optionally taken together with said nitrogen atom to form a 3-8 membered saturated, partially unsaturated, or aryl ring having 1-4 heteroatoms independently selected from nitrogen, oxygen, or sulfur.

In certain embodiments, the present invention provides a compound of formula A having the stereochemistry as depicted in formula A':

A'

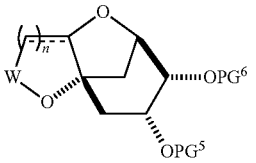

wherein each variable is as defined above and described in classes and subclasses above and herein.

In certain embodiments, the present invention provides a compound of formula A' wherein W is C(O) and said compound is of formula A'-1:

A'-1

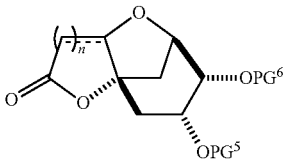

wherein each variable is as defined above and described in classes and subclasses above and herein.

As defined generally above, the A group of formulae A and A' is a $C_{1-6}$ aliphatic group, wherein A is optionally substituted with $Q^1$. In certain embodiments, the A group of formulae A and A' is a $C_{2-5}$ aliphatic group, wherein A is substituted with one or more $Q^1$ groups.

As defined generally above, each $Q^1$ group of formulae A and A' is independently selected from cyano, halo, azido, oxo, OR, SR, $SO_2R$, $OSO_2R$, $N(R)_2$, NR(CO)R, NR(CO)(CO)R, $NR(CO)N(R)_2$, NR(CO)OR, (CO)OR, O(CO)R, $(CO)N(R)_2$, $O(CO)N(R)_2$, or $OPG^1$, wherein $PG^1$ is a suitable hydroxyl protecting group. In certain embodiments, each $Q^1$ group of formulae A and A' is independently selected from cyano, halo, azido, oxo, $N(R)_2$, OR, SR, $SO_2R$, or $OSO_2R$. In other embodiments, each $Q^1$ group of formulae A and A' is independently selected from cyano, halo, azido, oxo, OR, SR, $SO_2R$, $OSO_2R$, $N(R)_2$, NR(CO)R, NR(CO)R, and $O(CO)N(R)_2$. In still other embodiments, exemplary $Q^1$ groups include NH(CO) (CO)-(heterocyclic radical or heteroaryl), $OSO_2$-(aryl or substituted aryl), O(CO)NH-(aryl or substituted aryl), aminoalkyl, hydroxyalkyl, NH(CO) (CO)-(aryl or substituted aryl), NH(CO) (alkyl) (heteroaryl or heterocyclic radical), O(substituted or unsubstituted alkyl) (substituted or unsubstituted aryl), and NH(CO) (alkyl) (aryl or substituted aryl).

In certain embodiments, the A group of formulae A and A' has one of the following characteristics:

(1) A has at least one substituent selected from hydroxyl, amino, azido, halo, and oxo;

(2) A is a $C_{1-6}$ alkyl group having at least one substituent selected from hydroxyl, amino, and azido;

(3) A has at least two substituents independently selected from hydroxyl, amino, and azido;

(4) A has at least two substituents independently selected from hydroxyl and amino;

(5) A has at least one hydroxyl substituent and at least one amino substituent;

(6) A has at least two hydroxyl substituents;

(7) A is a $C_{2-4}$ aliphatic group that is substituted;

(8) A is a $C_3$ aliphatic group that is substituted;

(9) A has an (S)-hydroxyl alpha to the carbon atom linking A to the ring containing G or an (R)-hydroxyl; and

(10) A is a $C_{1-6}$ saturated aliphatic group having at least one substituent selected from hydroxyl and cyano.

The term "(S)-hydroxyl" means that the configuration of the carbon atom having the hydroxyl group is (S). Embodiments of the invention also include compounds wherein A is substituted at least once on each carbon atom: (1) alpha and gamma, (2) beta and gamma, or (3) alpha and beta to the carbon atom to which A is attached. Each of the alpha, beta, and gamma carbon atoms are independently in the (R) or (S) configuration. In certain embodiments, the invention provides said compound wherein A is substituted at least once on each carbon atom alpha and beta to the carbon atom to which A is attached.

Exemplary A groups of formulae A and A' include 2,3-dihydroxypropyl, 2-hydroxyethyl, 3-hydroxy-4-perfluorobutyl, 2,4,5-trihydroxypentyl, 3-amino-2-hydroxypropyl, 1,2-dihydroxyethyl, [2,3-dihyroxy-4-perflurobutyl] *2,3-dihydroxy-4-perfluorobutyl*, 3-cyano-2-hydroxypropyl, 2-amino-1-hydroxy ethyl, 3-azido-2-hydroxypropyl, 3,3-difluoro-2,4-dihydroxybutyl, 2,4-dihydroxybutyl, 2-hydroxy-2-(p-fluorophenyl)-ethyl, —$CH_2$(CO) (substituted or unsubstituted aryl), —$CH_2$(CO) (alkyl or substituted alkyl, such as haloalkyl or hydroxyalkyl) and 3,3-difluoro-2-hydroxypent-4-enyl.

In certain embodiments, the A group of either of formulae A and A' is 3-amino-2-hydroxypropyl.

According to one aspect, the present invention provides a compound of either of formulae A and A', wherein $Q^1$ is $OPG^1$, wherein $PG^1$ is a suitable hydroxyl protecting group. Suitable hydroxyl protecting groups are well known in the art and include those described in detail in Protecting Groups in Organic Synthesis, T. W. Greene and P. G. M. Wuts, 3rd edition, John Wiley & Sons, 1999, the entirety of which is incorporated herein by reference. In certain embodiments, the $PG^1$ moiety of either of formulae A and A', taken with the oxygen atom to which it is bound, is selected from esters, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetyl), crotonate, 4-methoxy-crotonate, benzoate, p-benzylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl) ethoxymethyl, and tetrahydropyranyl ethers. Examples of arylalkyl ethers include benzyl, p-methoxybenzyl (MPM), 3,4-dimethoxybenzyl, o-nitrobenzyl, p-nitrobenzyl, p-halobenzyl, 2,6-dichlorobenzyl, p-cyanobenzyl, 2- and 4-picolyl.

In certain embodiments, the $PG^1$ moiety of either of formulae A and A', taken with the oxygen atom to which it is bound, is a silyl ether or arylalkyl ether. In yet other embodiments, the $PG^1$ moiety of either of formulae A and A' is t-butyldimethylsilyl or benzoyl. In still other embodiments, the $PG^1$ moiety of either of formulae A and A' is t-butyldimethylsilyl ("TBS").

As defined generally above, two $Q^1$ on A are optionally taken together to form a 3-8 membered saturated, partially unsaturated, or aryl ring having 0-4 heteroatoms independently selected from nitrogen, oxygen, or sulfur. In certain embodiments, two $Q^1$ on A are taken together to form an epoxide ring.

In certain embodiments, the $PG^5$ and $PG^6$ groups of formula A and A' are independently selected from those suitable protecting groups described above for the $PG^1$ group of formula A and A'. In other embodiments, the $PG^5$ and $PG^6$ groups of formula A and A' are taken together to form a cyclic diol protecting group. Such diol protecting groups are well known in the art and include those described by Greene and include cyclohexylidene and benzylidene diol protecting groups.

In certain embodiments, the present invention provides a method for preparing compounds of formula F-2 according to Schemes V-a, V-b, and V-c below:

Scheme V-a

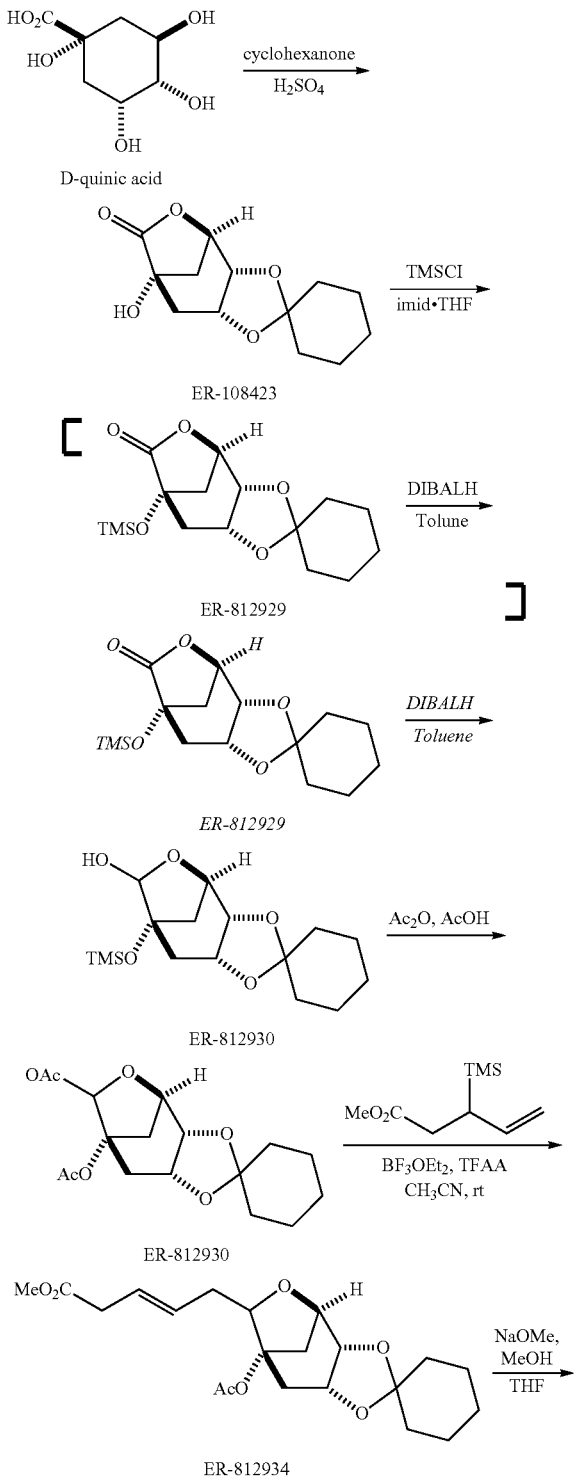

-continued
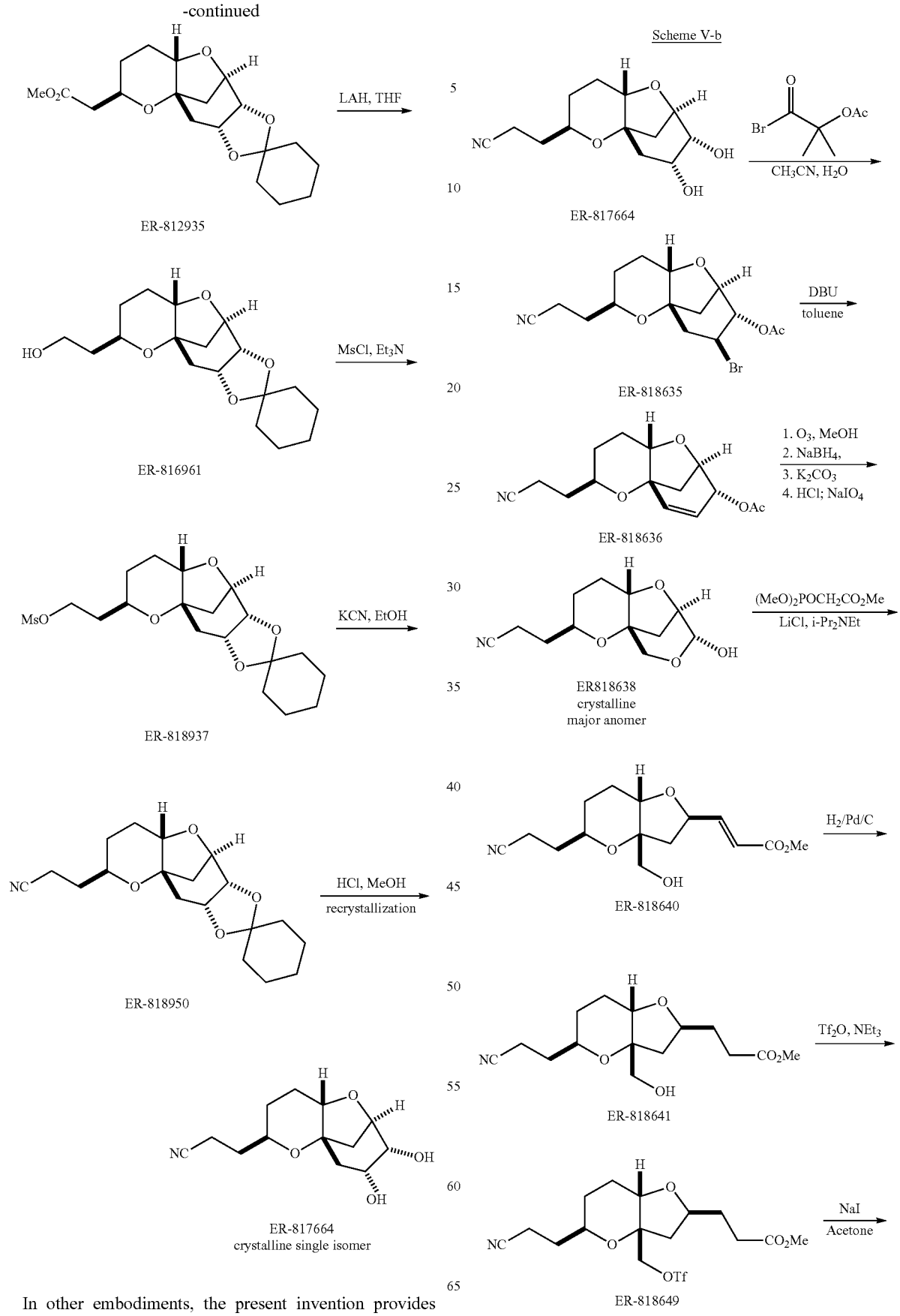
In other embodiments, the present invention provides crystalline ER-817664.

-continued
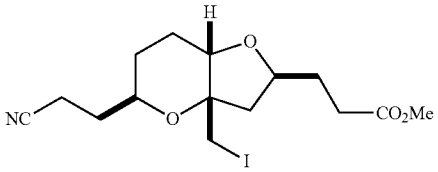
ER-818642
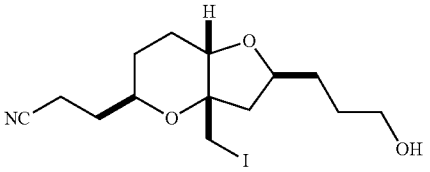
ER-818643
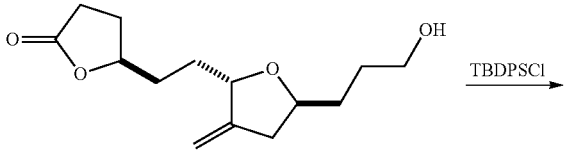
ER-818644
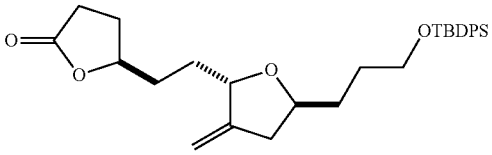
ER-813012
Scheme V-c
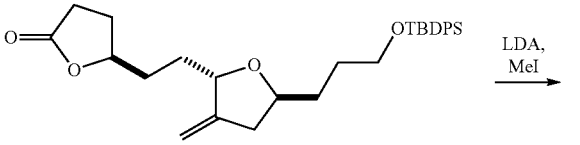
ER-813012
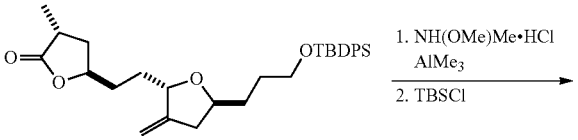
ER-817704
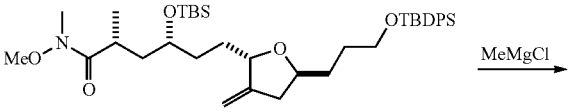
ER-806728
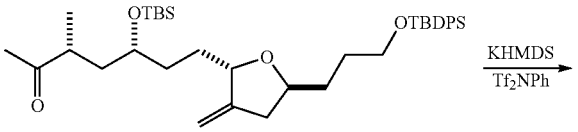
ER-806727
-continued
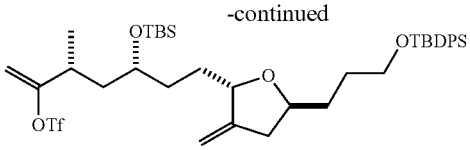
ER-806729
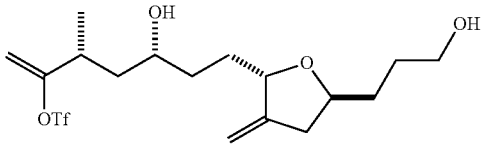
ER-806730
Using ER-817664 as a crystalline intermediate, Scheme VI-a shows a general method for using this compound in the preparation of intermediates useful for preparing compounds of formula F-2.
Scheme VI-a
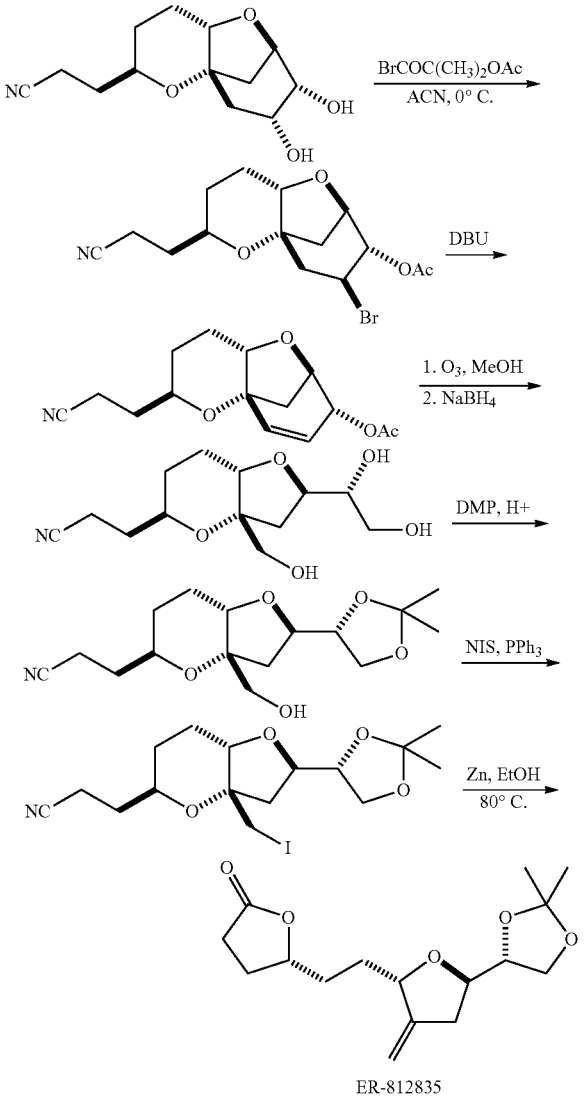
ER-812835

The triol intermediate depicted in Scheme VI-a above is used in an alternate method for preparing intermediates useful for preparing compounds of formula F-2, as shown in Scheme VI-b below.

Scheme VI-b

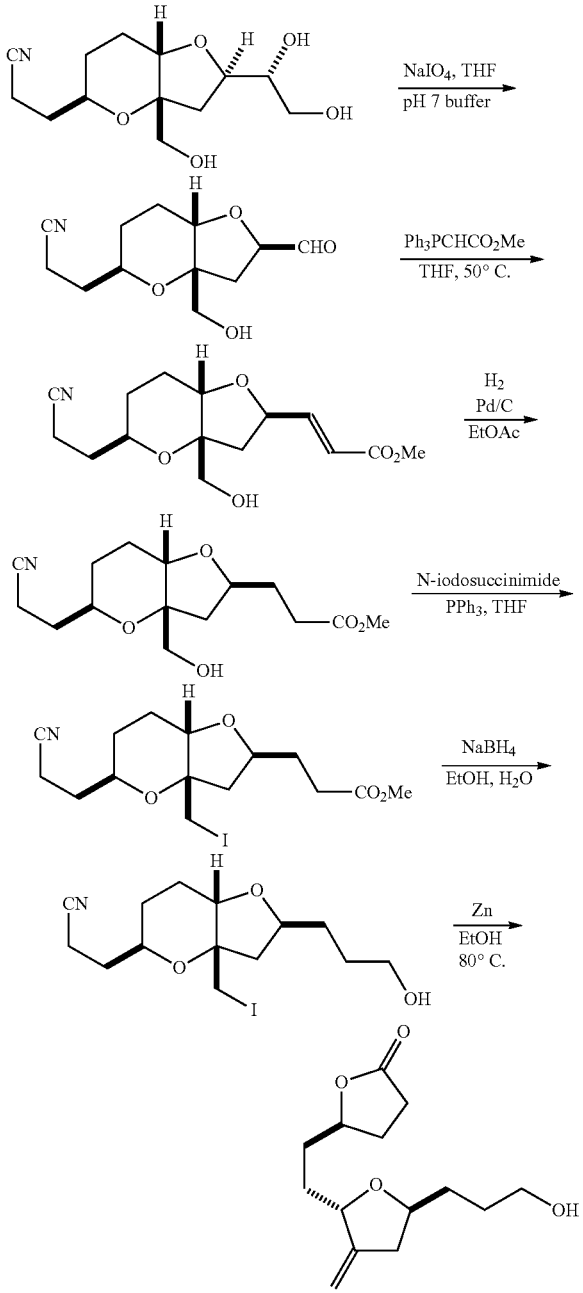

In Scheme VI-b, shown above, the triol intermediate is treated with periodate to form the aldehyde. This compound is homologated with methyl Wittig reagent, and the resulting olefin reduced, to form the ester compound. The remaining free hydroxyl group is treated with N-iodosuccinimide to form the iodo intermediate and the ester reduced with sodium borohydride to form the hydroxyl compound depicted above. One of ordinary skill in the art will recognize that the resulting iodo compound corresponds to compound 21 depicted in Scheme II, supra, wherein compound 21 has a protecting group at the hydroxyl position. The final treatment with zinc affords the lactone depicted above. One of ordinary skill in the art will recognize that the resulting lactone compound corresponds to compound 22 depicted in Scheme II, supra, wherein compound 22 has a protecting group at the hydroxyl position.

Yet another alternate method for preparing intermediates useful for preparing compounds of formula F-2 from D-quinic acid provides an alternative route from intermediate 2, of Scheme II as shown in Scheme VII below.

Scheme VII

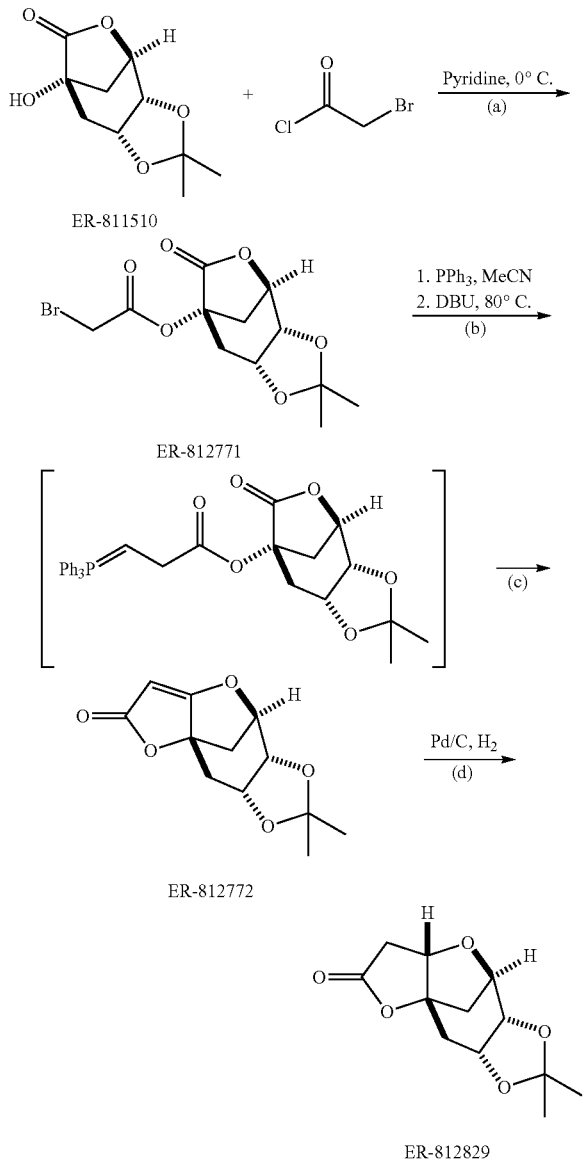

In Scheme VII above, intermediate 2 (from Scheme II) is used to prepare ER-812829 in a stereoselective manner. It will be appreciated that other protecting groups are useful for protecting the diol of ER-812829. Such groups are known to one of ordinary skill in the art and include cyclohexylidene and benzylidene diol protecting groups.

First, at step (a), the hydroxyl group of ER-811510 is treated with 2-bromo acetylchloride to form ER-812771. The bromo intermediate is treated with triphenylphosphine to form a Wittig reagent in situ in a manner substantially similar to that described by Murphy, et al, Tetrahedron Letters, 40, (1999) 3455-3456. This Wittig reagent then forms the lactone ER-812772. At step (d), stereoselective hydrogenation of the double bond affords ER-812829.

The present invention also provides a method for preparing intermediates useful for preparing compounds of formula F-2 from D-quinic acid, from intermediate ER-812829 depicted in Scheme VII above, as shown in Scheme VII-a below.

Scheme VII-a

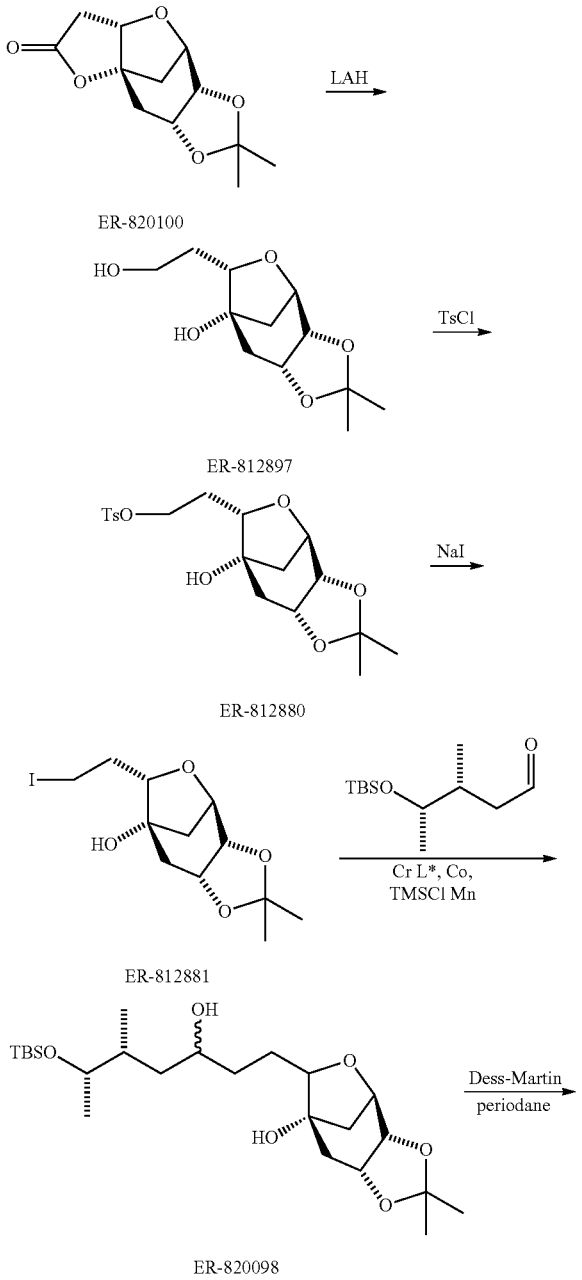

-continued

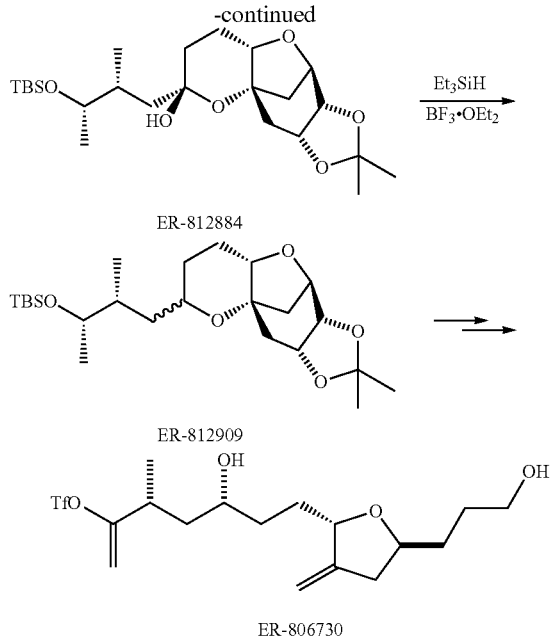

3. Fragment F-3

According to yet another embodiment, the present invention provides a compound F-3:

F-3

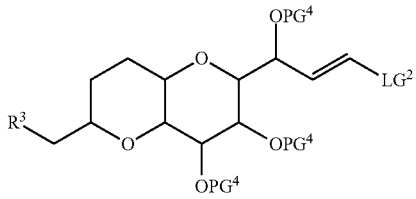

wherein:

each $PG^4$ is an independently selected suitable hydroxyl protecting group;

$R^3$ is CHO or $C(O)OR^4$;

$R^4$ is a suitable carboxyl protecting group; and $LG^2$ is a suitable leaving group.

Suitable carboxylate protecting groups are well known in the art and are described in detail in Protecting Groups in Organic Synthesis, T. W. Greene and P. G. M. Wuts, 3rd edition, John Wiley & Sons, 1999. In certain embodiments, the $R^4$ group of F-3 is an optionally substituted $C_{1-6}$ aliphatic group or an optionally substituted aryl group. Examples of suitable $R^4$ groups include methyl, ethyl, propyl, isopropyl, butyl, isobutyl, benzyl, and phenyl wherein each group is optionally substituted.

As described above, suitable leaving groups are well known in the art, e.g., see "Advanced Organic Chemistry," Jerry March, 4th Ed., pp. 351-357, John Wiley and Sons, N.Y. (1992). Such leaving groups include, but are not limited to, halogen, alkoxy, sulphonyloxy, optionally substituted alkylsulphonyloxy, optionally substituted alkenylsulfonyloxy, optionally substituted arylsulfonyloxy, silyl, and diazonium moieties. Examples of suitable leaving groups include chloro, iodo, bromo, fluoro, methanesulfonyloxy (mesyloxy), tosyloxy, triflate, nitro-phenylsulfonyloxy (nosyloxy), and bromo-phenylsulfonyloxy (brosyloxy). In certain embodiments, the $LG^2$ moiety of F-3 is iodo.

According to an alternate embodiment, the suitable leaving group may be generated in situ within the reaction medium. For example, $LG^2$ in a compound of formula F-3 may be generated in situ from a precursor of that compound of formula F-3 wherein said precursor contains a group readily replaced by $LG^2$ in situ. In a specific illustration of such a replacement, said precursor of a compound of formula F-3 contains a group (for example, a trimethylsilyl group) which is replaced in situ by $LG^2$, such as an iodo group. The source of the iodo group may be, e.g., N-iodosuccinimide. Such an in situ generation of a suitable leaving group is well known in the art, e.g., see Id.

As described above, suitable hydroxyl protecting groups are well known in the art and include those described in detail in Protecting Groups in Organic Synthesis, T. W. Greene and P. G. M. Wuts, 3rd edition, John Wiley & Sons, 1999 the entirety of which is incorporated herein by reference. In certain embodiments, each $PG^4$, taken with the oxygen atom to which it is bound, is independently selected from esters, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetyl), crotonate, 4-methoxy-crotonate, benzoate, p-benzylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl) ethoxymethyl, and tetrahydropyranyl ethers. Examples of arylalkyl ethers include benzyl, p-methoxybenzyl (MPM), 3,4-dimethoxybenzyl, o-nitrobenzyl, p-nitrobenzyl, p-halobenzyl, 2,6-dichlorobenzyl, p-cyanobenzyl, 2- and 4-picolyl.

In certain embodiments, one, two, or three of the $PG^4$ moieties of F-3, taken with the oxygen atom(s) to which they are bound, are silyl ethers or arylalkyl ethers. In yet other embodiments, one, two, or three of the $PG^4$ moieties of F-3 are t-butyldimethylsilyl or benzyl. In still other embodiments, all three of the $PG^4$ moieties of F-3 are t-butyldimethylsilyl.

According to another embodiment, a compound of formula F-3 is provided wherein said compound has the stereochemistry as depicted in formula F-3':

F-3'

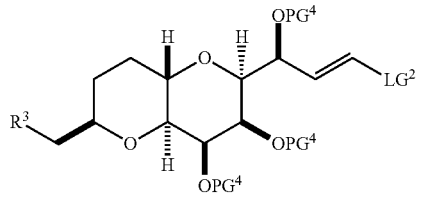

wherein each variable is as defined above and described in classes and subclasses above and herein.

In certain embodiments, a compound F-3a is provided:

F-3a

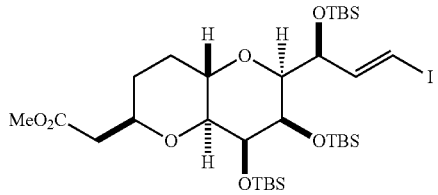

wherein "TBS" refers to t-butyldimethylsilyl.

Details of the synthesis of F-3a are set forth in the Examples infra.

4. Assembly of F-1, F-2, and F-3 to Prepare Compound I

Coupling of the fragments F-1 and F-2 is accomplished, in general, as set forth in Scheme VIII below.

Scheme VIII

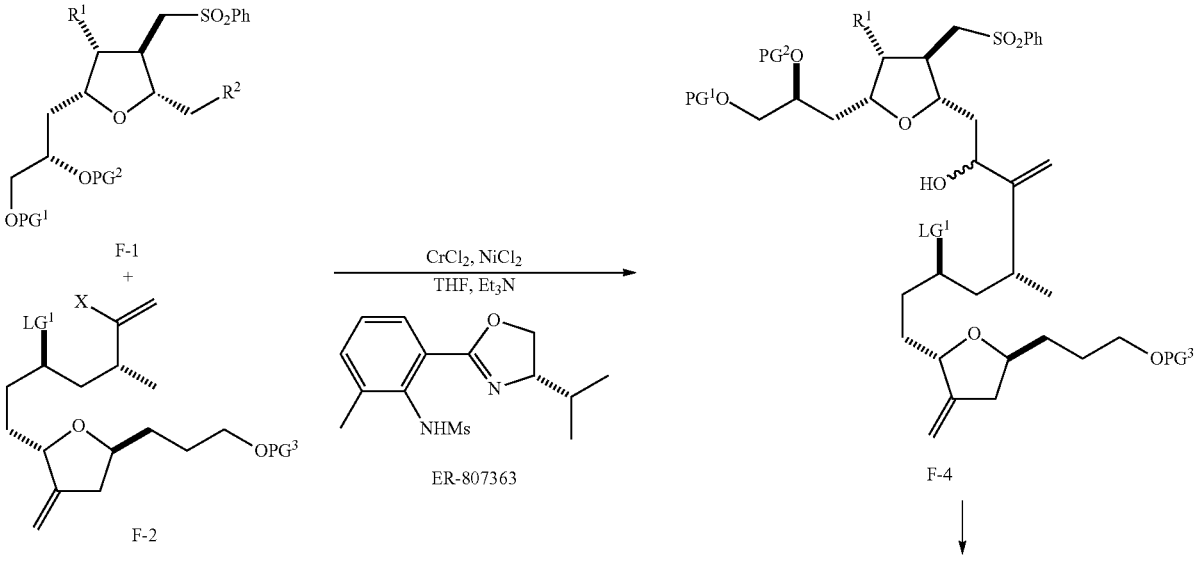

-continued

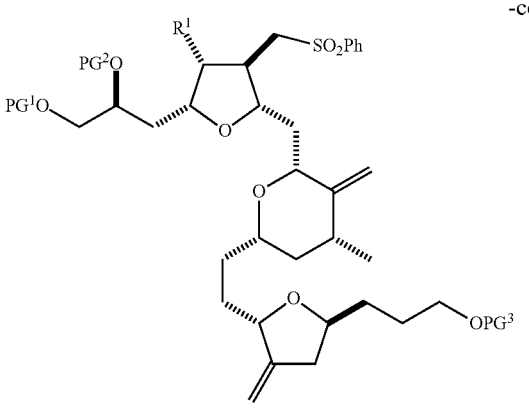

F-5a

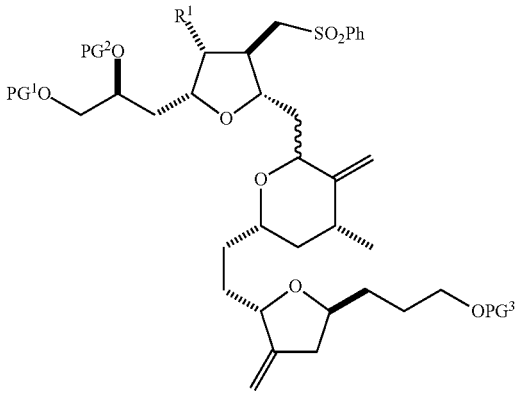

F-5

Scheme VIII above shows a general method for preparing intermediate F-5a from fragments F-1 and F-2. First, fragments F-1 and F-2 are coupled using methods substantially similar to that described by Kishi, et al., Org Lett 4:25 p 4431 (2002) to afford intermediate F-4. This coupling is performed in the presence of the chiral oxazole (ER-807363) or, alternatively, in the absence of ER-807363. However, the coupling reaction of F-1 and F-2 proceeds with higher selectivity when performed in the presence of ER-807363. Intramolecular Williamson ether formation of F-4, by treating F-4 with potassium hexamethyldisilazide, then furnishes tetrahydropyran F-5 as a mixture of stereoisomers. The stereoisomers are then separated to afford F-5a. The details of these steps are set forth in the Examples infra.

According to another embodiment, the present invention provides a compound F-4:

F-4

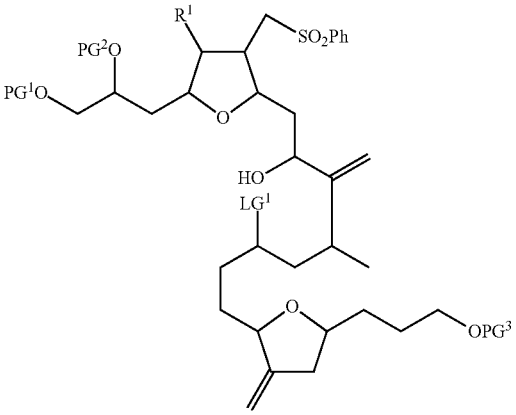

wherein $PG^1$, $PG^2$, $PG^3$, $LG^1$, and $R^1$ are as defined in general and in subclasses above and herein. *$PG^3$ is hydrogen or a suitable hydroxyl protecting group.*

In certain embodiments, the present invention provides a compound of formula F-4 wherein said compound has the stereochemistry depicted in formula F-4':

F-4'

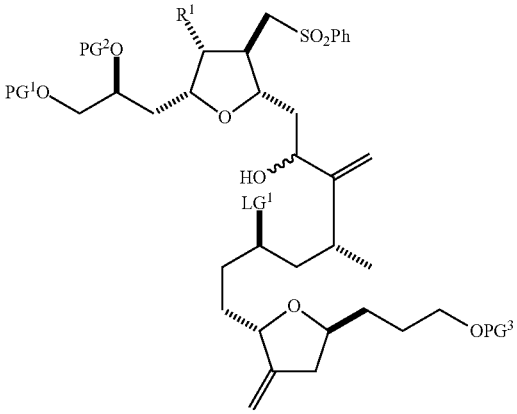

wherein $PG^1$, $PG^2$, $PG^3$, $LG^1$, and $R^1$ are as defined in general and in subclasses above and herein.

The present invention also provides a compound F-4a:

F-4a

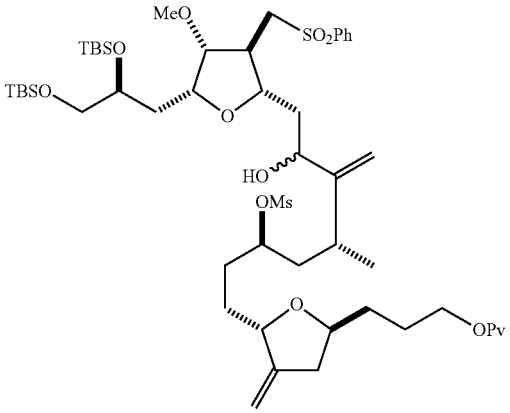

wherein "MsO" refers to mesylate, "TBS" refers to t-butyldimethylsilyl, and "OPv" refers to pivaloate.

Details of the synthesis of F-4a are set forth in the Examples infra.

According to yet another embodiment, the present invention provides a compound F-5:

F-5

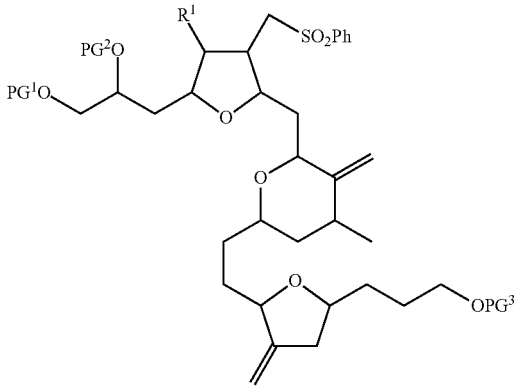

wherein each $PG^1$, $PG^2$, $PG^3$, and $R^1$ is as defined in general and in subclasses above and herein.

In certain embodiments, the present invention provides a compound of formula F-5 having the stereochemistry as depicted in formula F-5' or F-5a:

F-5'

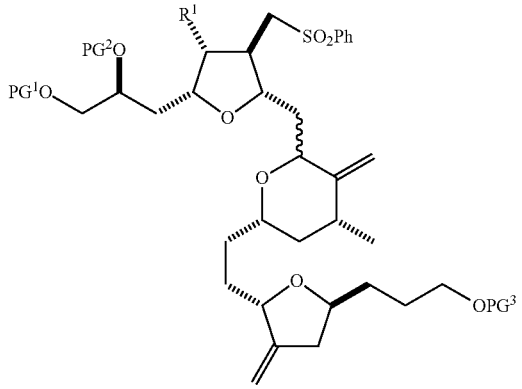

-continued

F-5a

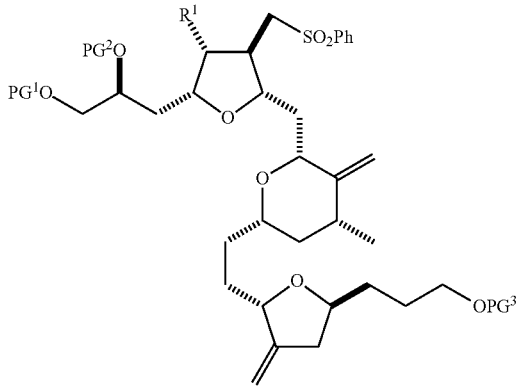

wherein each $PG^1$, $PG^2$, $PG^3$, and $R^1$ is as defined in general and in subclasses above and herein.

The $PG^3$ group of intermediate F-5a is removed and the resulting hydroxyl compound F-6 is then coupled with a compound F-3', wherein $R^3$ is CHO, to form F-7 as depicted in Scheme IX below.

Scheme IX

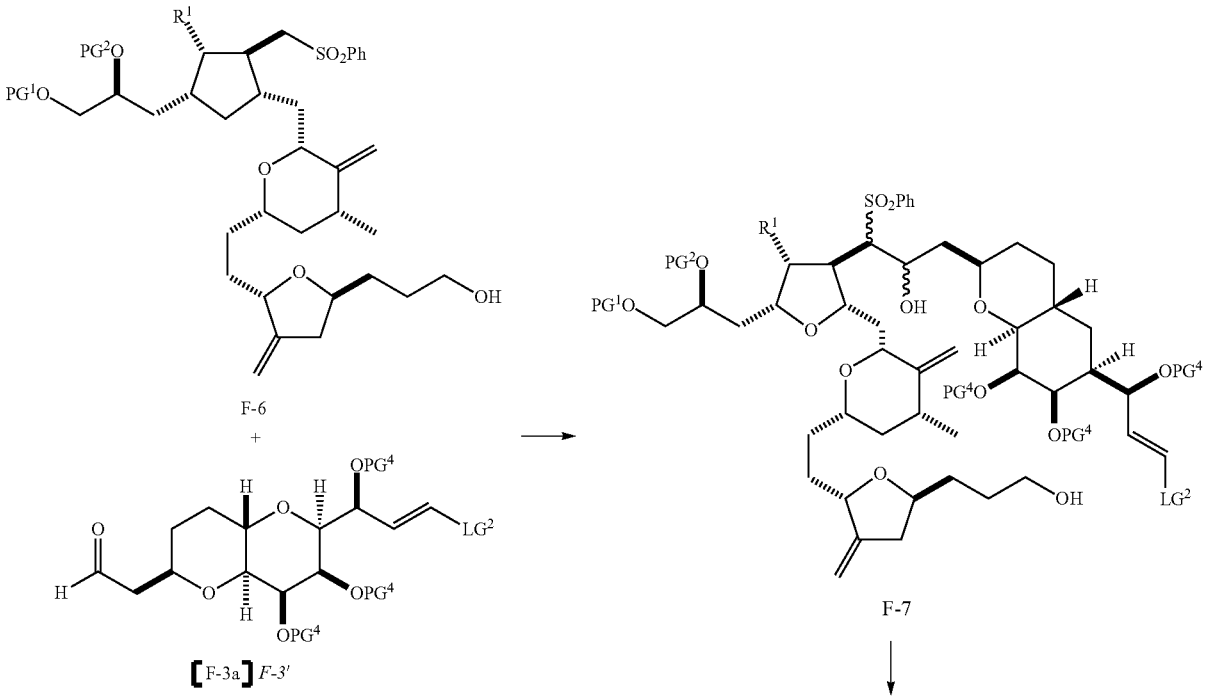

-continued

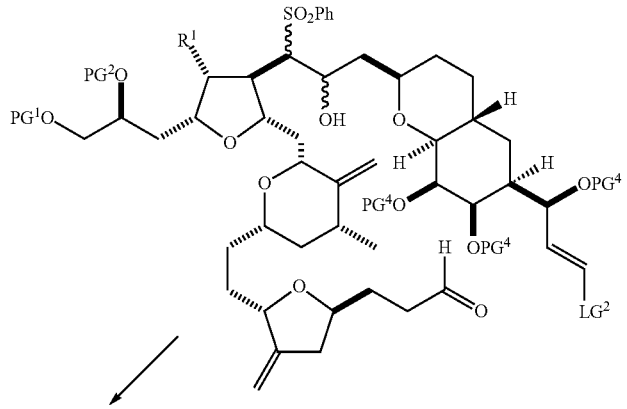

F-8

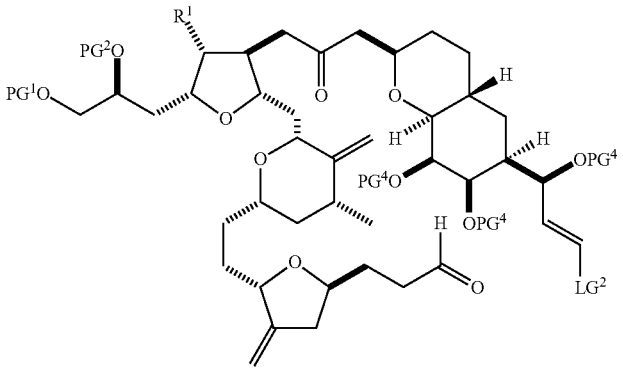

F-9

Scheme IX above shows a general method for preparing an intermediate-F-9 from F-3'and F-6. First, the sulfone intermediate F-6 is treated with n-butyl lithium then with the aldehyde F-3'. The resulting diol intermediate F-7 is then oxidized with Dess-Martin reagent to form the ketone-aldehyde intermediate F-8 which is then treated with $SmI_2$ to afford intermediate F-9. The details of these steps are set forth in the Examples infra.

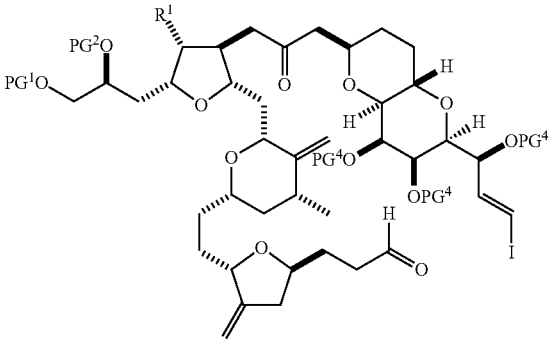

F-9a

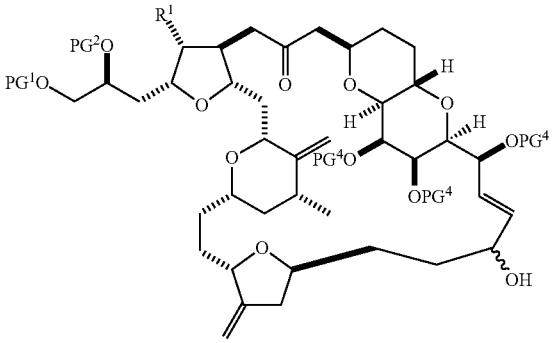

F-10

-continued

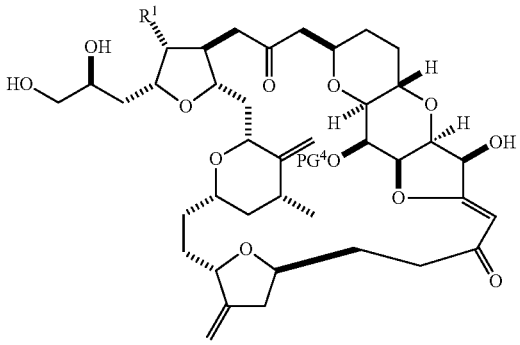

F-12

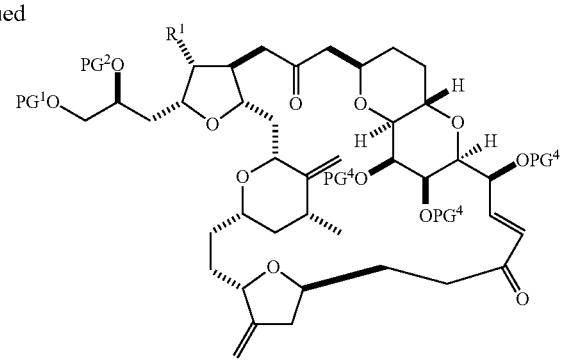

F-11

Scheme X above sets forth a general method for preparing the Halichondrin B analogs of the present invention from F-9a ($LG^2$ is iodo). First, an intramolecular coupling is achieved, by conditions substantially similar to those described at Scheme V above, to form hydroxyl compound F-10. In an alternate method, the intramolecular coupling is performed in the presence of the chiral oxazole ligand, described herein. The addition of the chiral oxazole ligand imparts a higher yield and greater efficiency for the reaction. The details of this reaction are set forth in the Examples below. Compound F-10 is then oxidized to form F-11. The hydroxyl protecting groups of F-11 are removed by appropriate means to afford F-12. One of ordinary skill in the art would recognize that the methods appropriate to achieve removal of the protecting groups of compound F-11 depend upon the actual protecting groups used and include those described by Greene. For example, when each of the hydroxyl protecting groups of F-11 is a TBS group, such removal may be achieved by treatment with optionally buffered tetrabutylammonium fluoride. The details of these steps are set forth in the Examples infra.

Intermediate F-12 is useful for preparing various analogs of Halichondrin B as described in, e.g. U.S. Pat. Nos. 6,365,759 and 6,469,182 the entirety of which are incorporated herein by reference.

EXAMPLES

Using the preparation of Halichondrin B analog B-1939 to exemplify, the following Examples describe the synthesis of Halichondrin B analogs using the methods and compounds of the present invention.

B-1939

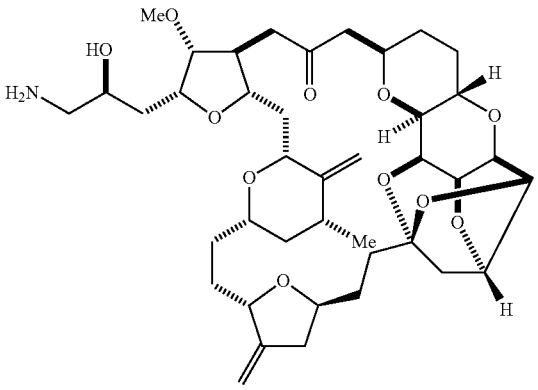

One of ordinary skill in the art would recognize that many analogs of Halichondrin B are prepared by the methods and from the compounds of the present invention including, but not limited to, those analogs of Halichondrin B described in U.S. Pat. Nos. 6,214,865 and 6,365,759, the entirety of which are herein incorporated by reference. Accordingly, it will be appreciated that the synthetic methods described below, by way of example, do not limit the scope of the invention which is defined by the appended claims.

Example 1

Preparation of F-1a

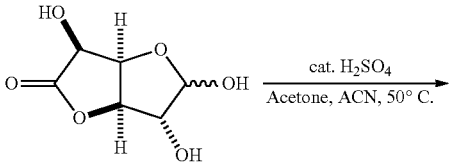

ER-806044

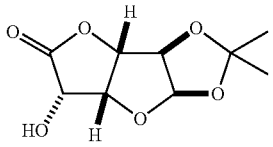

ER-806045

In an appropriately sized vessel, D-glucurono-6,3-lactone (1 wt., 1 eq.) was combined with ACN (3 vol.) and acetone (9 vol.). Catalytic conc. sulfuric acid was added and the system held at reflux for 3 hours. The system was checked for dissolution of D-glucurono-6,3-lactone. The reaction was cooled to 25° C. and stirred for 15 hours. Solid sodium bicarbonate (0.5 wts) was added and the reaction stirred for 3 additional hours. Solids were removed by filtration and the organics were partially concentrated and azeotroped with additional ACN (2 wts). ER-806045 was taken into the next reaction without isolation.

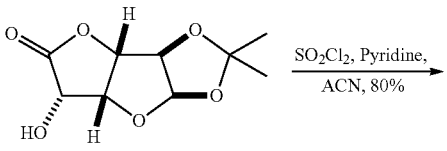

ER-806045

-continued

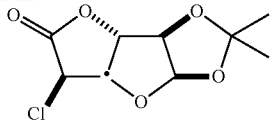

ER-806410

Crude ER-806045 (1 wt, 1 eq.) was dissolved in ACN (6.5 vol.) at −20° C. Pyridine (1.5 vol., 4.0 eq.) was added and $SO_2Cl_2$ (0.38 vol., 1.02 eq.) was added slowly, while keeping the internal temperature below 5° C. The reaction was quenched by inverse addition into cool water (28 vol.) with an ACN rinse (0.5 vol.), keeping the internal temperature below 10° C. The white solid, ER-806410 (0.87 wt., 79% of theoretical) was isolated by filtration with a heptane rinse (2 vol.) and drying.

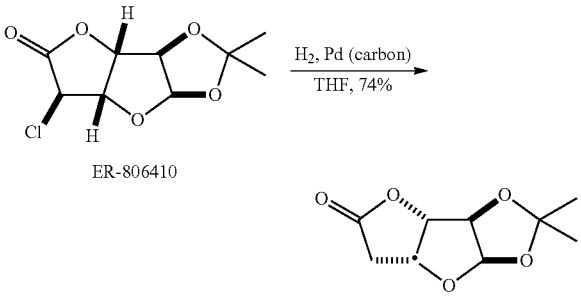

ER-806410

ER-806047

An appropriately sized vessel was charged with ER-806410 (1 wt, 1 eq.) and THF (10 vol.) and then cooled to 10° C. Wet palladium on carbon (5%, 0.5 wts) was added and the heterogeneous solution stirred for ten minutes. The reaction was buffered with pyridine (0.44 wts, 1.3 eq.) and placed under a hydrogen atmosphere for 3 hours. The reaction was filtered and the solids rinsed with water (2 vol.) and EtOAc (10 vol.). The resulting solution was acidified with 1N HCl (2.1 vol.), mixed well and the resulting layers were separated. The organic layer was sequentially washed with aqueous sodium bicarbonate (5 vol.) and water (5 vol.). The organics were concentrated under reduced pressure and the resulting product recrystallized from IPA (3.4 vol.) and further cropped by the addition of heptane (3.4 vol.) at 15° C. ER-806047 was isolated as a white solid (67% yield).

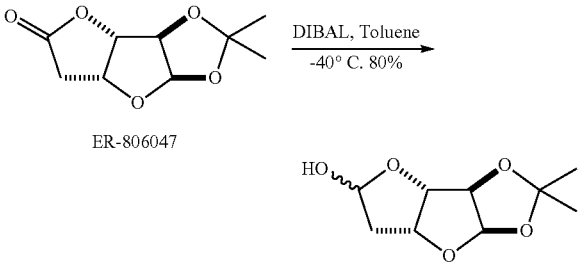

ER-806047

ER-806048

An appropriately sized vessel was charged with ER-806047 (1 wt, 1 eq.) and toluene (8 vol.) and then cooled to −40° C. A 17 wt % solution of DIBAL in toluene (4.6 wts, 1.1 eq.) was added, keeping the internal temperature below −35° C. After assaying the reaction, excess reagent was quenched by the addition of acetone (0.15 wts, 0.5 eq.), keeping the temperature below 10° C. The reaction was diluted with EtOAc (7 vol.) and 15% aqueous citric acid (8 wts) below 10° C.; and stirred at 20° C. until a clear solution was obtained. The layers were separated and the aqueous layer back extracted twice with EtOAc (2×10 vol.). The combined organics were washed sequentially with aqueous sodium bicarbonate (5 vol.) and brine (5 vol.) and then dried with magnesium sulfate (0.2 wts). After filtration, the organic layers were partially concentrated at reduced pressure, and azeotroped with toluene (4 vol.). The products were stored as a THF solution for use in the next reaction.

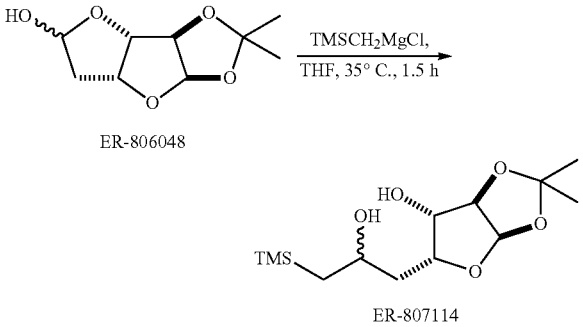

ER-806048

ER-807114

An appropriately sized vessel was charged with a 20 wt % ether solution of $TMSCH_2MgCl$ (2.04 wts, 3.0 eq.) and chilled below 5° C. A THF (7 vol.) solution of ER-806048 (1 wt, 1 eq.) was added to the reaction vessel keeping the internal temperature below 15° C. The reaction was warmed to 35° C. for 1.5 hours. The reaction was cooled, diluted with toluene (7 vol.) and quenched with AcOH (3 vol.) below 20° C. The reaction was further diluted with 10% aqueous ammonium chloride (6 wts), mixed well, and the layers were separated. The organic layer was washed sequentially with aqueous sodium bicarbonate (5 vol.) and brine (5 vol.). After drying over magnesium sulfate (0.2 wts) and filtration, the solution was concentrated under reduced pressure and ER-807114 isolated as a concentrated solution in toluene (90% yield).

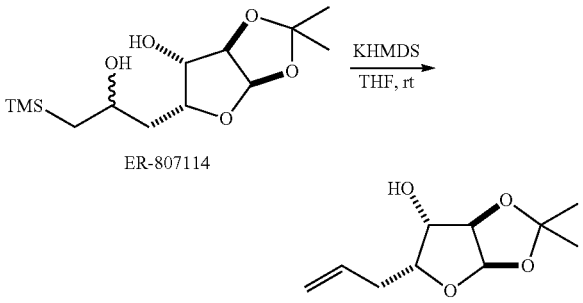

ER-807114

ER-806049

An appropriately sized vessel was charged sequentially with ER-807114 (1 wt, 1 eq.) and THF (20 vol.), and the solution was cooled below 5° C. A 15 wt % solution of KHMDS in toluene (9.16 wts, 2.0 eq.) was added. The reaction was quenched with 10% aqueous ammonium chloride (5 vol.). The layers were separated and the organic layer washed sequentially with ammonium chloride (5 vol.), 2N HCl (8.5 vol.), aqueous sodium bicarbonate (5 vol.), and water (5 vol.). The organics were transferred to concentration vessels using EtOAc, and concentrated to a viscous oil (90% yield). The material was recrystallized from toluene (4 vol.) and heptane (4 vol.) at 35° C. with additional cropping at lower temperatures and heptane (2×4 vol.) at 15 and 10° C. (94% yield).

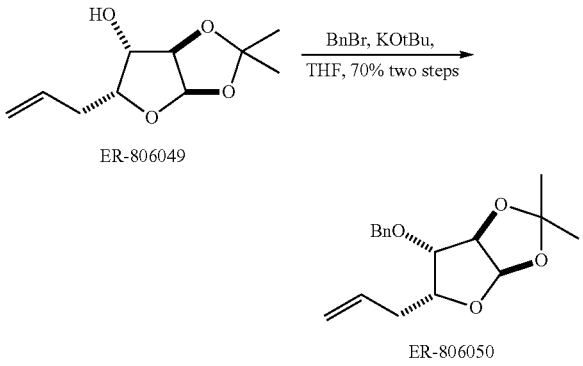

An appropriately sized vessel was charged with KOtBu (0.67 wts, 1.2 eq.) and THF (7.7 vol.), and cooled to an internal temperature of −20° C. A solution of ER-806049 (1 wt, 1 eq.) in THF (2.3 vol.) was added keeping the internal temperature below −7° C. Neat BnBr was added, maintaining −7° C. as the maximum temperature. The reaction was stirred at −20° C. for 2 hours and 10 hours at 10° C. The reaction was quenched with 10% aqueous $NH_4Cl$ (4 wts), diluted with toluene (4 vol.), and mixed well. The layers were separated and the organic layer washed with 10% brine (4 wts) and dried over $MgSO_4$ (0.15 wts). ER-806050 was isolated as a tBuOH solution (2.5 vol.) after concentration at reduced pressure (95% yield).

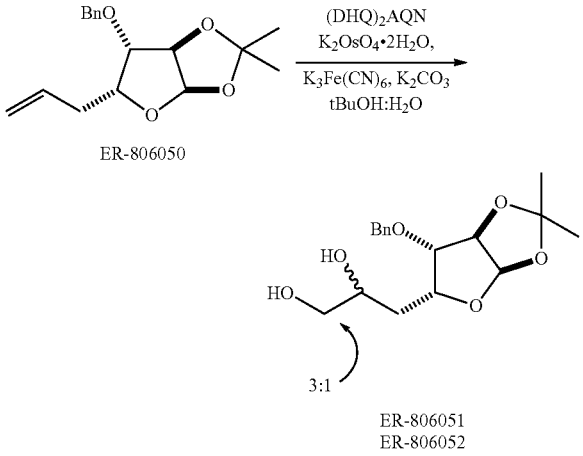

An appropriately sized vessel was charged sequentially with $K_3Fe(CN)_6$ (3.5 wt., 3.4 eq.), $K_2CO_3$ (1.5 wt., 3.4 eq.), $(DHQ)_2AQN$ (0.0134 wt., 0.005 eq.), water (18 vol.), t-BuOH (13 vol.), and ER-806050 in tBuOH (1 wt, 1 eq. in 5 vol.). The heterogeneous mixture was cooled to an internal temperature of 0° C., and $K_2OsO_4.2H_2O$ (0.0029 wt., 0.22 mole %) was added. After 36 hours at 0° C., the reaction was quenched with $Na_2S_2O_3$ (3.5 eq., 1.7 wt.) and the flask allowed to warm to ambient temperature overnight. After 15 hours, the mixture was transferred to a workup vessel and diluted with toluene (15 vol.) and water (4 vol.). The biphasic mixture was vigorously stirred and separated. The organic layer was washed with brine (10 vol.), and concentrated and solvent exchanged to afford a crude mixture of diols ER-806051 and ER-806052 as a 10% toluene solution (92% yield).

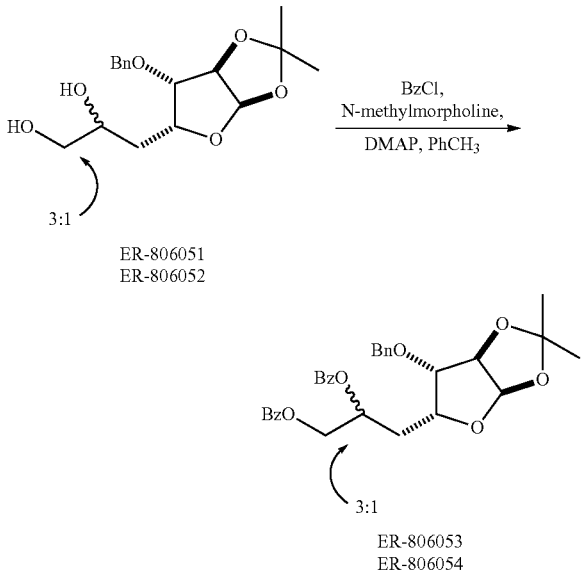

The toluene solution (10.1 wt %, 9.9 wts) of ER-806051/52 (1 wt, 1 eq.) was further diluted with additional toluene (3 wts). N-Methylmorpholine (0.94 wts, 3.0 eq.) and DMAP (0.075 wts, 0.2 eq.) were added to the toluene solution and the resulting mixture was cooled below 15° C. Benzoyl chloride was added keeping the internal temperature below 25° C. The reaction was then stirred for 12 hours at 75° C. The reaction was cooled to 15° C. and the temperature kept below 25° C. during the 1N HCl (5 vol.) quench. Layers were mixed well and separated. The organic layer was sequentially washed with brine (3 wts), aqueous sodium bicarbonate (3 wts), and brine (3 wts). The organic layer was dried ($MgSO_4$, 0.25 wts), treated with activated carbon (0.1 wts), and filtered (Celite®, 0.3 wts) with a toluene (1 wt). The products were partially concentrated under reduced pressure, azeotroped with toluene (3 wts). Bisbenzoate ER-806053/54 was isolated in 95% yield as a toluene solution (5 vol.).

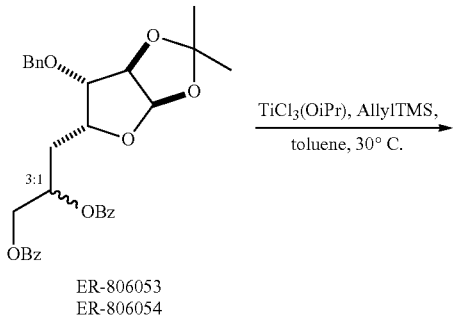

-continued

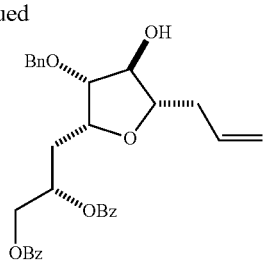

ER-806055

Under an inert atmosphere, a 20 wt % solution of $TiCl_4$ (6.42 wts, 3.6 eq.) in toluene was cooled to 15° C. Keeping the internal temperature below 30° C., $Ti(OiPr)_4$ (0.64 wts, 1.2 eq.) was added, and the resulting solution stirred for 15 minutes. AllylTMS (1.03 wts, 4.8 eq.) was premixed with ER-806053/54 (1 wt, 1 eq.), available as a 22 wt % solution in toluene from the previous step (4.55 wts, 1 eq.), and added to the freshly generated $Ti(OiPr)Cl_3$. The internal temperature during the addition was kept below 30° C. The reaction was stirred between 20-30° C. for 2 hours. The reaction was cooled to −5° C. and quenched with 1N HCl (6 vol.), keeping the internal temperature below 30° C. After mixing well, the layers were separated and the organic layer sequentially washed with 1N HCl (3 vol.) and brine (2×3 vol.). The organic layer was stirred with $MgSO_4$ (0.3 wts) and activated carbon (0.15 wts) and filtered through a Celite® plug (0.2 wts), rinsing with toluene (1 vol.). The product, as a 3:1 mixture at C-34 was isolated after concentration in 83% yield. Recrystallization from IPA/n-heptane afforded ER-806055 with [99.5%] >99.5% d.e. at C-34 (71% yield).

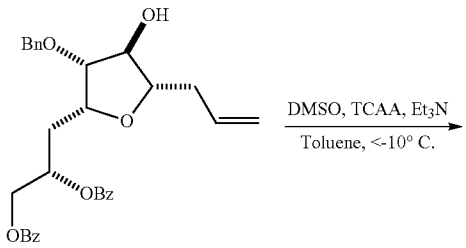

ER-806055

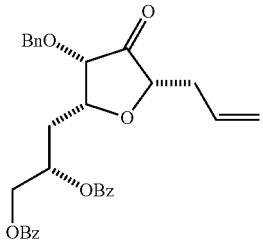

ER-806058

At room temperature, an appropriately sized vessel was charged with alcohol ER-806055 (1 wt., 1.0 eq.), toluene (7 vol.), DMSO (0.31 wt., 2.0 eq.) and $Et_3N$ (0.78 wt., 4.0 eq.). The resulting solution was cooled to −19° C. TCAA (0.84 wt., 1.4 eq.) was added drop-wise, keeping the internal temperature below −10° C. The reaction was stirred for an additional 10 minutes. The reaction was diluted with IPA (0.5 vol.) and quenched with 1N HCl (5 vol.), keeping the internal temperature below 10° C. The layers were separated and the organic layer sequentially washed with aqueous $NaHCO_3$ (5 wt.) and water (3 vol.). The organic layer was partially concentrated at reduced pressure (100% crude yield) and further azeotroped with additional toluene (4 vol.). The resulting ketone (ER-806058) was dissolved in a final 4 vol. of toluene, checked for water content and used as is in the next reaction.

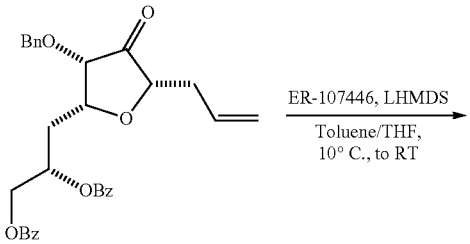

ER-806058

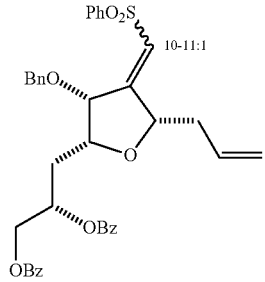

ER-806059

A solution of ER-107446 (1 wt, 1.5 eq.) in THF (2.7 vol.) was cooled to 10° C. and treated with 25.5 wt % LHMDS in THF (5.2 wt., 1.4 eq.), keeping the internal temperature below 15° C. In a second vessel, the toluene solution of crude ER-806058 (21.9 wt %, 5.4 vol.) was cooled to 10° C. The contents of vessel one were transferred into the substrate containing solution, keeping the internal temperature below 20° C. The reaction was stirred for 30 minutes then quenched by adding 1M HCl (6.5 vol.), keeping the internal temperature below 20° C. The layers were separated and the organic layer washed four times with 1:1 MeOH/water (4×5 vol.) and then with aqueous bicarbonate (5 vol.), and brine solutions (2×5 vol.). The product was dried over $MgSO_4$ (0.52 wt.), filtered (rinsing with 0.7 vol. of toluene), and concentrated to a heavy oil at reduced pressure.

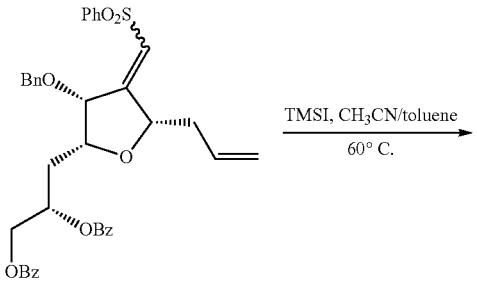

ER-806059

-continued

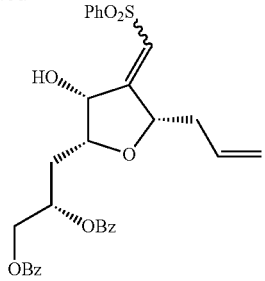

ER-806060

ER-806059 was dissolved in 1:1 toluene/$CH_3CN$ (5 vol.) at room temperature. Filtered TMSI (1.23 wt., 4 eq.) was added, keeping the initial temperature below 40° C. The reaction was heated to 60° C. for 2 hours. The reaction was cooled to −15° and quenched with 25% aqueous ammonium hydroxide below 30° C. The reaction contents were stirred overnight and the layers separated. The organic layer was charged with additional toluene (5 vol.) and water (2 vol.). The layers were mixed well and separated. The organic layer was then washed sequentially with 10% aqueous sodium sulfite (5 vol.), 1N HCl (5 vol.), 5% aqueous sodium bicarbonate (5 vol.), and brine (5 vol.). The organic layer was dried over $MgSO_4$ (0.2 wt.), filtered, partially concentrated and used in the next reaction as a 50% solution in toluene.

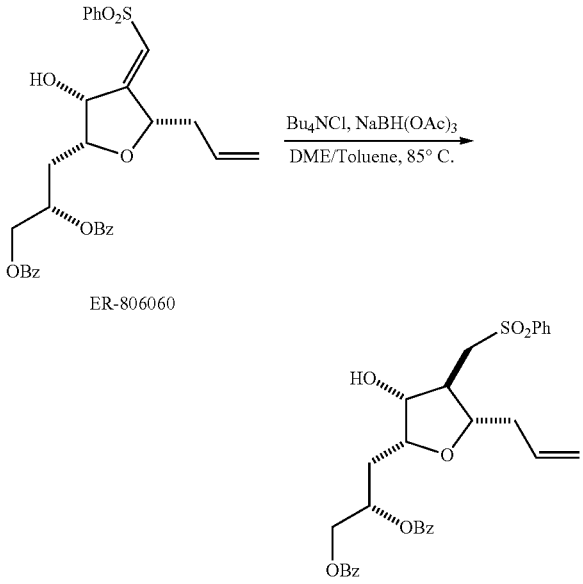

ER-806060

ER-806061

In an appropriately sized vessel, $NaBH(OAc)_3$ (1.19 wt, 3.15 eq.), $Bu_4NCl$ (1.04. wt, 2.1 eq.), DME (8.2 vol.), and toluene (4 vol.) at 65° C., were combined and stirred at room temperature. The mixture was heated to 75° C. for one hour. ER-806060 (1 wt., 1 eq.) as a 50% wt solution in toluene was added at 75° C. and rinsed in with additional toluene (0.3 vol.). The reaction temperature was raised to 85° C. and the reaction stirred for 2-4 hours. The reaction was cooled to <10° C. and quenched with water (3.2 vol.) keeping the internal temperature below 20° C. The layers were mixed well and separated. The organic layer was sequentially washed with aqueous sodium bicarbonate (2×5 vol.) and water (2×5 vol.). The organic layer was concentrated and solvent exchanged to afford a 40 wt % solution of ER-806061 in MeOH.

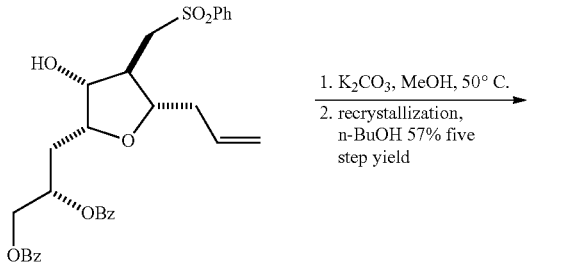

ER-806061

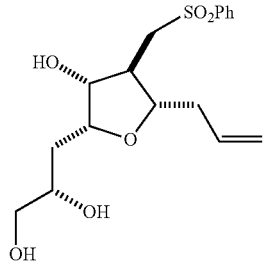

ER-806064

A 40 wt % solution of ER-806061 (1 wt., 1.0 eq.) in MeOH was dissolved in additional methanol (1.6 vol.). Potassium carbonate (0.24 wts, 1.0 eq.) was added and the reaction temperature was raised to 50° C. for one hour. The reaction was cooled to 15° C., and quenched with 1N HCl (3.5 vol., 2 eq.) with the internal temperature below 30° C. The reaction was diluted with water (3.9 vol.) and toluene (3 vol.). The layers were separated and the aqueous layer back extracted with toluene (1.5 vol.). The aqueous phase was charged with sodium bicarbonate (0.3 wts) and sodium chloride (0.6 wts), and back extracted with nBuOH (3 vol.). The three organic phases were combined and concentrated to dryness to afford crude triol ER-806064 and inorganic salts. The product was dissolved in 7:1 toluene/nBuOH at 80° C., hot filtered, and recrystallized by cooling and stirring overnight. ER-806064 (F-1b) was isolated in a 57%, five step overall yield after filtration and a toluene rinse. FAB (+)-MS m/z 357 (M+H). Melting point 96.2° C.

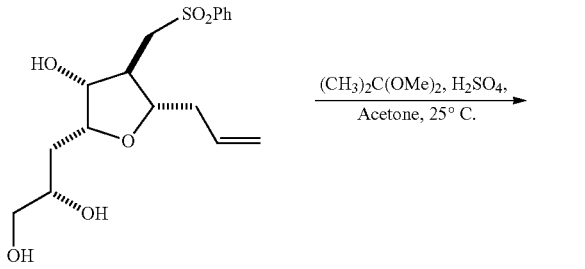

ER-806064

-continued

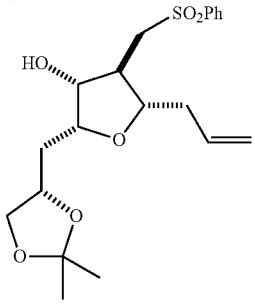

ER-806126

Purified triol ER-806064 (1 wt., 1 eq.) was dispersed in acetone (2 vol.), diluted with 2,2-dimethoxypropane (1 vol.), and treated with conc. sulfuric acid (0.0086 wts, 0.03 eq.) at 25° C. The reaction was stirred until homogenous. The reaction was diluted with toluene (5 vol.) and quenched by the addition to 5% $K_2CO_3$ (2 vol.). The layers were mixed well and separated. The organic layer was washed with 10% brine, dried with $Na_2SO_4$ (0.5 wt.). The solution was filtered (toluene rinse) and concentrated at reduced pressure to afford ER-806126 as a yellow oil. The material was used as is in the next stage.

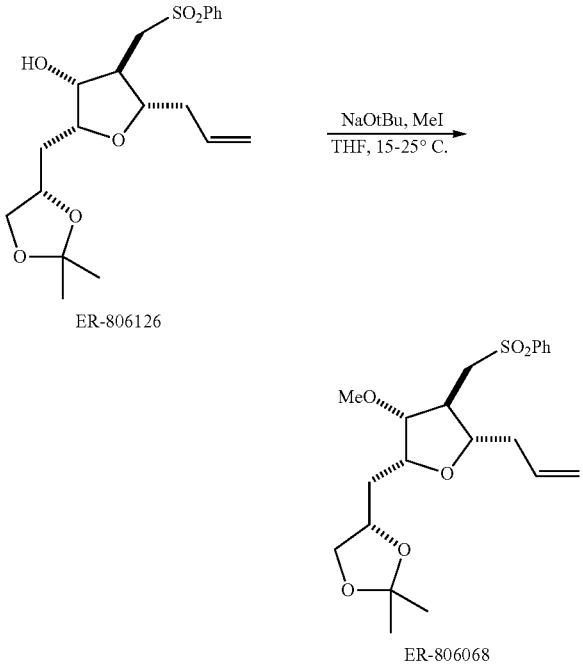

ER-806126

ER-806068

Solid NaOtBu (0.34 wt., 1.4 eq.) was dissolved in THF (2.7 vol.) and DMF (0.3 vol.), and then cooled below 10° C. A solution of ER-806126 (1 wt., 1 eq.) in THF (2.5 vol.) was added to the NaOtBu solution with a THF rinse (0.5 vol.), keeping the internal temperature below 15° C. After a 30 minute stir, methyl iodide (0.204 vol., 1.3 eq.) was added keeping the temperature below 15° C. (exothermic). The reaction was warmed to 25° C. and the reaction quenched with water (5 vol.) and diluted with toluene (7 vol.). The layers were mixed well and separated. The organic layer was washed twice with brine (2×5 vol.), dried over $Na_2SO_4$ (0.5 wt.), filtered, and concentrated under reduced pressure.

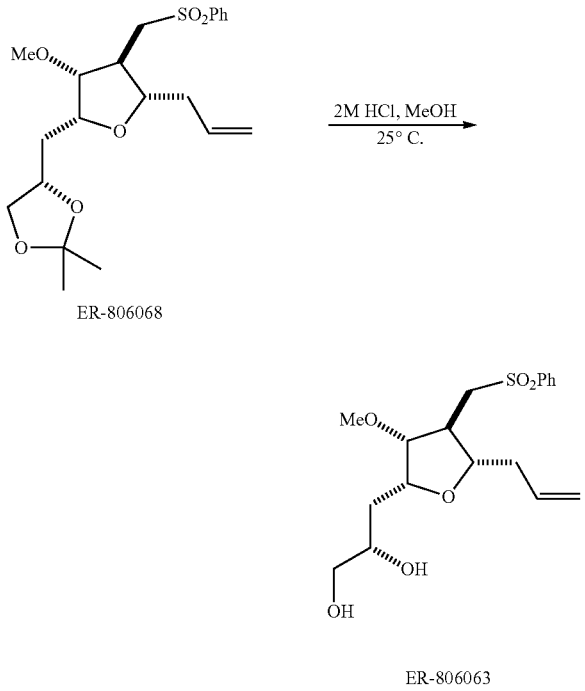

ER-806068

ER-806063

ER-806068 (1 wt., 1 eq.) was dissolved in 1 vol. of MeOH. Water (1.5 vol.) and 2 N HCl (1.25 vol., 1 eq.) were added and the reaction stirred at 25° C. The reaction was quenched by inverse addition to 2M NaOH (1.34 vol.) at 10° C. The reaction was diluted with isopropyl acetate (5 vol.), the layers were mixed well and separated. The aqueous layer was back extracted with 5 vol. of isopropyl acetate and the combined organic layers were dried over $MgSO_4$ (0.5 wt.), filtered, and concentrated at reduced pressure to afford crude diol ER-806063.

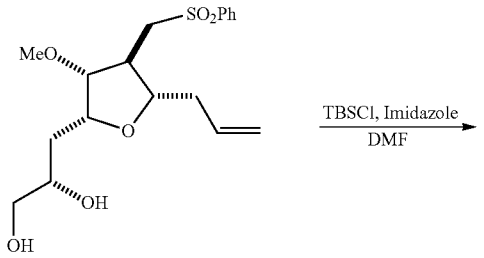

ER806063
$C_{18}H_{26}O_6S$
Mol. Wt.: 370.46

-continued

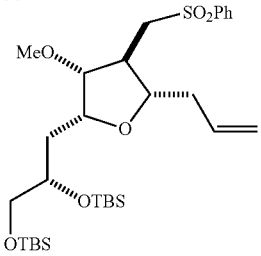

ER806065
$C_{30}H_{54}O_6SSi_2$
Mol. Wt.: 598.98

To a 25° C. solution of crude ER-806063 (1 wt., 1.0 eq.) in DMF (4 vol.), was charged imidazole (0.62 wt., 3.4 eq.), followed by TBSCl (1.02 wt., 2.53 eq.) with the internal temperature below 30° C. The reaction was stirred at 25° C. The reaction was diluted with MTBE (10 vol.) and washed with $H_2O$ (4 vol.). The organic layer was washed sequentially with 1M HCl (3 vol.), water (3 vol.), aqueous sodium bicarbonate (3 vol.), and brine (3 vol.). The organic layer was dried over $MgSO_4$ (0.5 wt.), filtered with one volume MTBE rinse, and concentrated at reduced pressure and solvent exchanged for heptane (4 vol.).

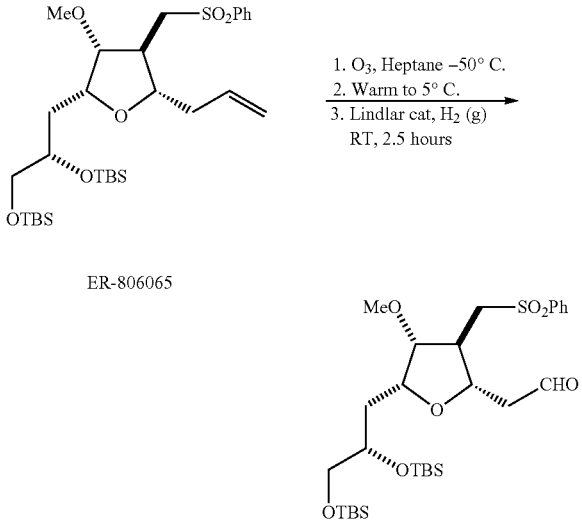

ER-806065 (1 wt., 1 eq.) was dissolved in heptane, isooctane, or IPA (10 vol.) The solution was cooled below −60° C. (±10° C.). Ozone was bubbled through the solution at low temperature until the solution retained a blue color. Nitrogen was purged through the solution for 15-30 minutes, and the reaction warmed to 5° C. while the nitrogen flush was continued. 7-15 wt. % Lindlar Catalyst (5% Pd on $CaCO_3$ poisoned with Pb, 0.1 wt.) was added. The reactor head was purged several times with nitrogen, evacuated, and placed under 1 atmosphere $H_2$ (g). The reaction was then warmed to room temperature (20-25° C.). The reaction was stirred for 2.5 hours. The resulting heterogeneous solution was filtered through Celite® (1.0 wt.) with an MTBE (2 vol.) rinse. The solution was concentrated to dryness, isolating 1.0 wt. of crude ER-806067. The crude isolate was recrystallized from heptane or isooctane to afford ER-806067 (F-1a) as a white crystalline solid in a 68% five step yield. FAB(+)-MS m/z 601 (M+H). Melting point 64.5° C.

Example 2

Preparation of F-2a

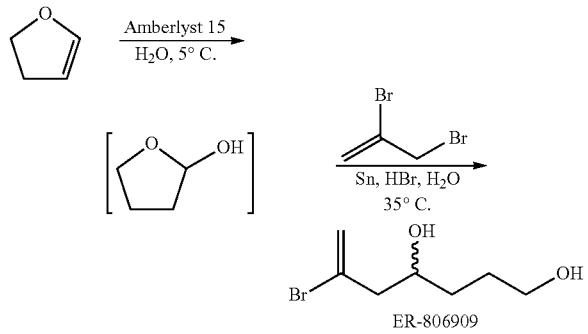

A reactor was charged with pre-rinsed Amberlyst 15 (0.05 wt.) and water (4.63 vol.) and cooled to an internal temperature of 0-5° C. The reactor was charged with 2,3-dihydrofuran (1 wt., 1 eq.) and stirred for 1.5 hours maintaining internal temperature around 5° C. A second reactor was charged with water (4.63 vol.) and heated to an internal temperature of 35° C. The same reactor was charged with tin powder (2.2 wt., 1.3 eq.), distilled 2,3-dibromopropene (3.71 wt., 1.3 eq.), and 48% hydrobromic acid (0.002 vol.), respectively. After observation of reaction initiation indicated by a temperature spike to 36-38° C., the second reactor was charged with 2,3-dibromopropene portion-wise (9×0.37 wt.) while maintaining the internal temperature below 45° C. After complete addition, the contents of the second reactor were stirred at an internal temperature of 35° C. for an additional 60 minutes. The filtered contents of the first reactor were charged into the second reactor at a rate such that internal temperature did not exceed 45° C. After complete addition, the heat source was removed and the second reactor was charged with Celite® 545 (2.0 wt.) and the resulting mixture stirred for 30 minutes. The heterogeneous mixture was filtered through a Celite® 545 pad (2.0 wt.) and the cake washed with additional water (5 vol.). All filtrates were combined into a reactor and charged with concentrated hydrochloric acid (1.5 vol.) until the cloudy solution becomes clear. With vigorous stirring, the reactor was charged with sodium chloride (3.6 wt.) and the layers allowed to partition. The organic layer was separated and set aside. The aqueous layer was extracted with n-butanol (20 vol.). The aqueous layer was drained and the reactor charged with the organics from the first separation. The organics were washed with concentrated sodium bicarbonate (24 vol.), followed by a back extraction of the aqueous layer with n-butanol (20 vol.). All organics were combined and concentrated in vacuo. The concentrate was dissolved in MTBE (10 vol.), filtered and the filtrate was concentrated to two vol. With stirring, the concentrate was cooled to an internal temperature of 0° C. and then n-heptane (4 vol.) was added. The heterogenous mixture was stirred for 2 hours at an internal temperature of 0° C. and the desired product was isolated via filtration and dried under vacuum to yield ER-806909 (1.34 wt., 0.45 eq.) as a white powder.

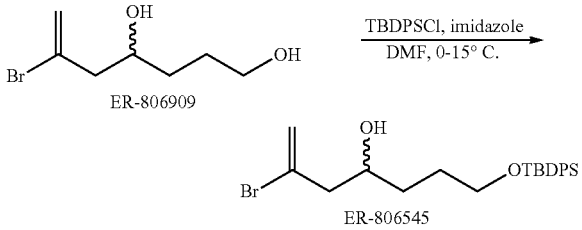

A reactor was charged with imidazole (0.65 wt., 2 eq.), ER-806909 (1 wt., 1 eq.), and anhydrous DMF (4.04 vol.). With stirring, the reactor was cooled to an internal temperature of 0° C. and then with tert-butylchlorodiphenylsilane (1.25 wt., 0.95 eq.) at a rate such that internal temperature did not exceed 15° C. While maintaining the internal temperature <15° C., the reaction was stirred for an additional 1 hour. The reactor was charged with water (3.2 vol.) and n-heptane (6.4 vol.). The mixture was stirred for 5-15 minutes and the layers allowed to separate. The organic layer was separated and set aside. The aqueous layer was extracted with n-heptane (3.2 vol.). All organics were combined and washed with brine (3.2 vol.) and concentrated in vacuo to a constant weight to yield ER-806545 (2.13 wt., 0.95 eq.) as a yellow oil. The product was utilized in the next stage without further purification.

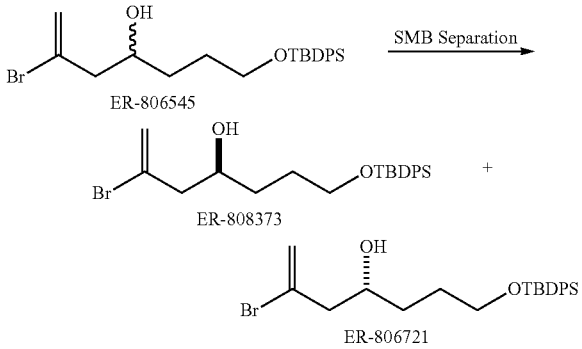

The enantiomers of ER-806545 were separated via Simulated Moving Bed (SMB) chromatography to yield ER-808373 (0.55 wt., 0.55 eq.) and ER-806721 (0.45 wt., 0.45 eq.) as yellow oils. The SMB chromatography protocol used to separate the enantiomers of ER-806545 is as follows.

| | |
|---|---|
| Columns and media: | Chiracel OD 20 μm 30 mm × 150 mm (12 columns) |
| Solvent system: | 96:4 (vol/vol) heptane:tert-butanol (mobile phase) |
| Simulated Moving Bed Chromatography apparatus: | Knauer SMB System CSEP C912 |
| Isotherms (Langmurian, determined by frontal analysis): | |
| Undesired isomer: | Qi* = 2.8768 × Ci/(1 + 0.02327 × Ci) |
| Desired isomer: | Qi = 4.5320 × Ci/(1 + 0.0034595 × Ci) |
| *Where Qi = solid phase concentration (in g/L) and Ci = liquid phase concentration (g/L). | |
| Column porosity: | 0.658 |
| Temperature: | 27° C. |

Flow rates, etc. calculated by simulation on EuroChrom 2000 for Windows, SMB Guide ver.1.2, Wissenschaftliche Geratebau Dr.-Ing. Herbert Knauer GmbH, D-14163 Berlin; authors, H. Kniep and A. Seidel-Morgenstern:

| | |
|---|---|
| Feed concentration: | 36 g/L (ER-806545) |
| Feed flow rate (Pump 1): | 15 mL/min |
| Eluent flow rate (Pump 2): | 76.4 mL/min |
| Zone IV (Pump 3) flow rate: | 107 mL/min |
| Zone II (Pump 4) flow rate: | 134.3 mL/min (actual flow rate = 143.5 mL/min) |
| Zone I flow rate: | 183.4 mL/min |
| Zone III flow rate: | 149.3 mL/min |
| Raffinate* flow rate: | 42.3 mL/min *Raffinate = weakly bound isomer |
| Extract flow rate: | 49.1 mL.min *Extract = strongly bound isomer |
| Tact time (port switching time): | 0.8864 min (53.18 sec, actual tact time = 54 sec) |

The enantiomers of ER-806545 were separated using the above protocol in the following manner. For an 11 hour run, 10 L of 36 g/L ER-806545 in mobile phase was pumped (Silog model Chemtech) through a 142 mm diameter 0.45 μm pore size nylon filter (Cole-Parmer # 2916-48) and into the Feed tank. The Eluant tank was filled with 36L mobile phase that has been filtered through an in-line 45 mm diameter 1 μm glass fiber filter (Whatman GFC), additional vol. were added throughout the run. The internal temperature of the SMB apparatus was adjusted to 27° C.

For initial startup, the Feed and Eluant inlets were both connected to the Eluant tank. The Feed and Eluant pumps were primed and purged with mobile phase solvent. The SMB apparatus column switching was initiated, the pumps were turned on and the flow rates were gradually increased to full speed while maintaining absolute flow rate differences between each pump. Once fall speed was achieved the Raffinate and Extract flow rates were measured and adjustments to pump flow rates were made to correct for deviations in pump specifications. The Feed pump (Pump 1) was reduced to 0 mL/min, the inlet reconnected to the Feed tank, the pump primed with Feed solution and then the flow rate gradually increased back to full operating speed. The Raffinate and Extract outlets were collected into separate tanks and samples of each of each were acquired every 2 hours. The samples were monitored for chiral purity by analytical HPLC using the HPLC method set forth below. Adjustments to the flow rates of Pumps 2, 3 and 4 as well as to the tact time were made to afford the desired outlet purities.

At the end of the run, the Feed pump was once again reduced to zero flow rate and connected to the Eluant tank. The Feed pump was brought back to full speed and the system was allowed to wash for 20 minutes. The Raffinate and Extract outlets were maintained for 10 minutes (10 tacts) during the wash period and, for the remainder of the wash, the outlets were collected into a separate tank. The column wash was eventually concentrated and added to the Feed on subsequent runs.

The collected Extract (ER-806721) at the end of each run was pooled with material collected from the same starting material lot and the final pooled lot was analyzed again for chiral purity by the analytical HPLC method described in Table 1 below. The same procedure was applied to the collected Raffinate (ER-808373).

TABLE 1

| HPLC Analysis of ER-806721 chiral purity: | |
|---|---|
| Column: | Chiracel OD 10 um 250 × 4.6 mm, DAICEL Chemical Industries, Ltd., cat. no. 14025 |
| Flow rate: | 0.8 mL/min |
| Temp. (° C.): | 27 preferred over 35 |
| Inj. Vol.: | 10 uL usually, sample in Solvent A, 5 mg/mL |
| Instrument: | Waters Alliance W2690 with UV W2487 (also with Advanced Laser Polarimeter) |

| Mobile Phase Constituents: | | (PDR-Chiral, Inc.) |
|---|---|---|
| A | 99:1 Heptane:2-Propanol | |
| B | | |
| C | | |
| D | | |

| Gradient Table: | (%) | | | | Gradient |
|---|---|---|---|---|---|
| Time (min) | A | B | C | D | |
| 0 | 100 | 0 | 0 | 0 | isocratic |
| Run time | 30 min | | | | |

Detection: Absorbance at 254 nm UV

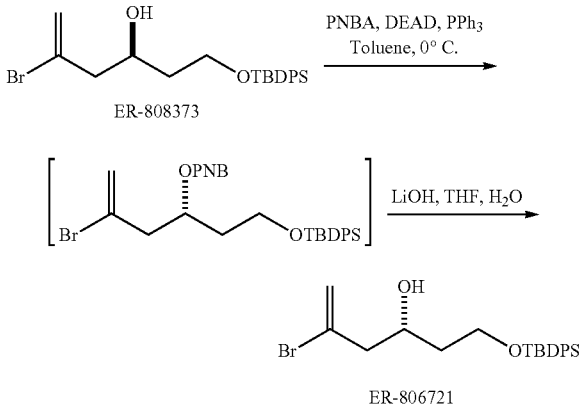

A reactor was charged with triphenylphosphine (0.7 wt., 1.2 eq.), p-nitrobenzoic acid (0.45 wt., 1.2 eq.), ER-808373 (1 wt., 1 eq.), and anhydrous toluene (8 vol.). The reaction was cooled to internal temperature of 0° C. and DEAD (1.17 wt., 1.2 eq.) was slowly added at a rate such that the internal temperature did not exceed 7° C. n-Heptane (3.3 vol.) was added and the mixture cooled to an internal temperature 10° C. then stirred for 30-40 minutes. The resulting precipitate was removed by filtration. The filter-cake was washed with n-heptane (3.3 vol.), TBME (0.55 vol.), n-heptane (1.1 vol.), and MTBE (0.55 vol.), respectively. All filtrates were combined and concentrated in vacuo. The crude concentrate was dissolved in THF (8 vol.) then water (0.8 vol.) and lithium hydroxide dihydrate (0.18 wt., 2 eq.) were added. The mixture was stirred at ambient temperature then n-heptane (3.3 vol.) was added and stirred for 5 minutes. Water (2.2 vol.) and n-heptane (3.3 vol.) were added, the biphasic mixture was stirred for 5 minutes, and the layers were allowed to partition. The aqueous layer was separated and back extracted with n-heptane as necessary. The organic layers were combined and concentrated in vacuo. The crude product was purified via $SiO_2$ column chromatography to yield ER-806721 (0.74-0.85 wt., 0.74-0.85 eq.) as a light yellow oil.

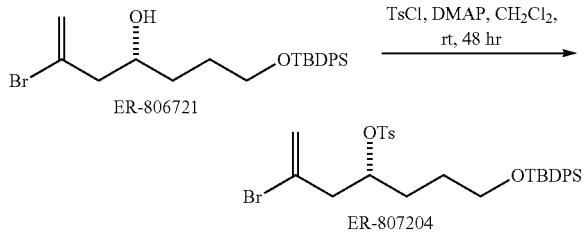

A reactor was charged with ER-806721 (1 wt., 1 eq.) and anhydrous dichloromethane (4.2 vol.). The reaction was cooled to an internal temperature of 0-5° C., then triethylamine (0.34 wt., 1.5 eq.), p-toluenesulfonyl chloride (0.51 wt., 1.2 eq.), and 4-(dimethylamino)-pyridine (0.001 wt., 0.25 eq.) were added. The resulting mixture was stirred at ambient temperature for 48 hours then water (1.8 vol.) and dichloromethane (1.8 vol.) were added. After sufficient mixing, the organics were separated and concentrated. The concentrate was dissolved in MTBE (1.8 vol.) and washed with brine (1.8 vol.). The organic layer was separated and set aside. The aqueous layer was back extracted with MTBE (1.8 vol.) then all organics were combined and concentrated in vacuo. The crude oil was filtered through a plug of $SiO_2$ (70-230 mesh, 1 wt.) eluting with MTBE (7 vol.) and the filtrates were concentrated in vacuo. The concentrate was dissolved in IPA (5 vol.) and water (0.25 vol.) was added. The resulting mixture was cooled to an internal temperature of 15° C. and then seeded with ER-807204. After seeding, the mixture was cooled to an internal temperature of 0° C. and stirred for 4-5 hours. The suspension filtered, the filter cake was washed with cold IPA (1 vol.), and the cake dried in vacuo to a constant weight to yield ER-807204 (1.05 wt., 0.78 eq.) as a white powder. IR (thin film, cm-1) λ 2597, 1633, 1363, 1177, 907, 729. LRMS m/z 602 (M+H).

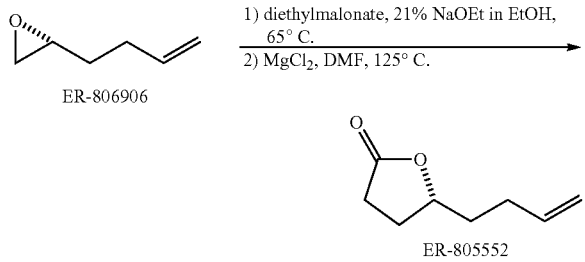

A reactor was charged with 21% sodium ethoxide in ethanol (2.97 wt., 0.9 eq.). The solution was heated to an internal temperature of 65° C. then diethyl malonate (3.24 wt., 2 eq.) was added at a rate such that the internal temperature did not exceed 70° C. The mixture was stirred for 30 minutes and then ER-806906 (1 wt., 1 eq.) was added over 3-5 hours. Upon complete addition, the reaction was stirred for 60 minutes and then cooled to an internal temperature of 50° C. Concentrated hydrochloric acid (0.84 wt., 1.05 eq.) was added at a rate such that internal temperature did not exceed 65° C. The DMF (3 vol.) and ethanol were removed via distillation then a solution of magnesium chloride hexahydrate (0.21 wt., 0.1 eq.) in distilled water (0.25 vol., 1.4 eq.) was added. The resulting mixture was heated to an internal temperature of 135° C. while removing the distillate. The mixture was heated at reflux then cooled to room temperature and brine (12 vol.) and TBME (16 vol.)

were added. The organic layer was separated and washed with water (1.3 vol.) and brine (1.2 vol.) then concentrated in vacuo. The product was purified via distillation to yield ER-805552 (0.95-1.09 wt., 0.71 eq.).

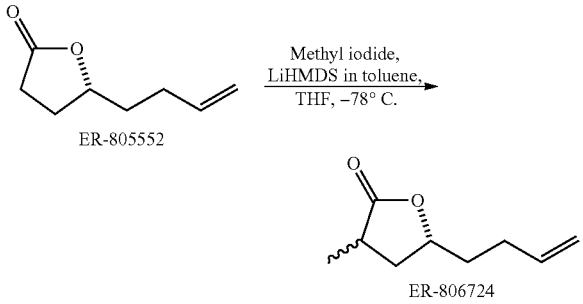

A reactor was charged with LHMDS 1.0 M in toluene (6.61 wt., 1.04 eq.) and cooled to an internal temperature of −75° C. ER-805552 (1 wt., 1 eq.) was dissolved in anhydrous THF and added to the reactor at a rate such that internal temperature did not exceed −70° C. Upon complete addition, the resulting mixture was stirred for 30 minutes. A second reactor was charged with anhydrous THF (2.5 vol.) and methyl iodide (1.27 wt., 1.25 eq.) and cooled to an internal temperature of −75° C. The solution of ER-805552 in THF was added into the methyl iodide solution at a rate such that internal temperature did not exceed −65° C. Upon complete addition, the reaction was stirred at an internal temperature of −78° C. for 30 minutes. The reaction was inverse quenched a solution of 1 N hydrochloric acid (10 vol.) and MTBE (8 vol.) with vigorous stirring. After complete addition, the aqueous layer was separated and discarded. The organic layer was washed with brine solution (3 vol.) and concentrated in vacuo and the product purified via distillation to afford ER-806724 (0.75 wt.) as a ~6/1 mixture of diastereomers.

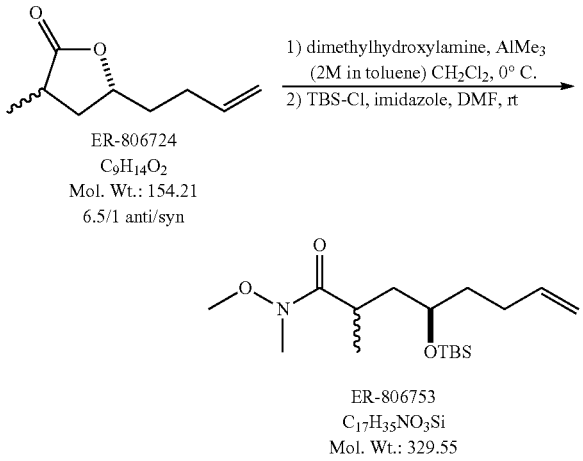

A reactor was charged with N,O-dimethylhydroxylamine HCl (1.05 wt., 1.5 eq.) and anhydrous $CH_2Cl_2$ (8.1 vol.) and cooled to an internal temperature of 0° C. 2 M trimethylaluminum in toluene (3.93 wt., 1.5 eq.) was added at a rate such that internal temperature did not exceed 5° C. The reaction was stirred for an additional 10 minutes and ER-806724 was added at a rate such that internal temperature did not exceed 5° C. The reaction was diluted with $CH_2Cl_2$ (15 vol.) then inverse quenched into 1.3 M sodium tartrate (20 vol.) at an internal temperature of 0° C. at a rate such that the internal temperature did not exceed 10° C. After complete addition, the layers were partitioned and the aqueous layer was separated and set aside. The organics were washed with water (1 vol.), dried over sodium sulfate (1 wt.), filtered and concentrated in vacuo until minimal methylene chloride was being removed. To the concentrate was added anhydrous DMF (6.3 vol.), imidazole (0.64 wt., 1.5 eq.) and t-butyldimethylsilyl chloride (0.94 wt., 0.97 eq.), respectively. Water (5 vol.) and MTBE (10 vol.) were added and the resulting mixture stirred then the layers were allowed to partition. The aqueous layer was separated and discarded. The organic layer was washed with water (5 vol.) and the layers separated. 1 N sodium hydroxide (2.5 vol.) and methanol (2.5 vol.) were added and the resulting mixture stirred. The aqueous layer was separated and the organic layer washed with brine (2.5 vol.) then concentrated in vacuo to afford ER-806753 (1.94 wt., 0.91 eq.) as a brown oil.

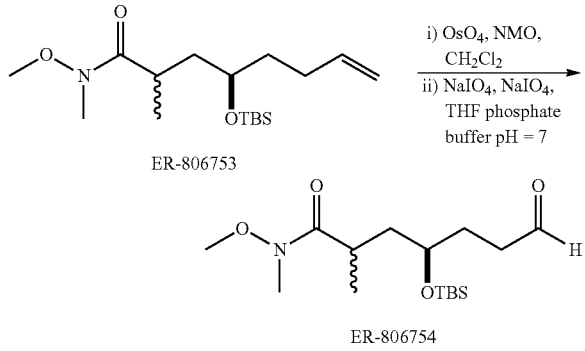

A reactor was charged with ER-806753 (1 wt., 1 eq.), $CH_2Cl_2$ (5 vol.) and NMO-50% in water (0.8 wt., 1.1 eq.). The mixture was cooled to an internal temperature of 10° C. and then 0.197 M $OsO_4$ in toluene (0.06 vol., 0.004 eq.) was added. Sodium sulfite (0.1 wt., 0.25 eq.) and water (0.85 vol.) were added and the reaction stirred for 1 hour. The mixture was diluted with brine (0.85 vol.) and the organics were concentrated in vacuo to approximately ⅓ vol. A second reactor was charged with sodium periodate (1.3 wt., 2 eq.) followed by THF (2.5 vol.). The mixture was diluted with pH=7 phosphate buffer (3.0 vol.) and cooled to an internal temperature of 20° C. The concentrated diol was added at a rate such that the internal temperature did not exceed 30° C. After complete addition, the resulting mixture was stirred at room temperature. Water (1.25 vol.), MTBE (7 vol.) and brine solution (1.25 vol.) were added and the layers separated. The organics were washed a second time with a mixture of brine solution (1 vol.) and saturated sodium bicarbonate (1 vol.). Finally, the organics were stirred over a mixture of brine (1 vol.) and 10% (w/v) sodium thiosulfate solution (1 vol.) for 1 hour then concentrated in vacuo. The crude material was purified via $SiO_2$ column chromatography to yield ER-806754 (0.93 wt., 0.93 eq.) as a yellow oil. IR (thin film, cm-1) λ 2953, 2856, 1725, 1664, 1463, 1254, 1092, 833. LRMS m/z 332 (M+H).

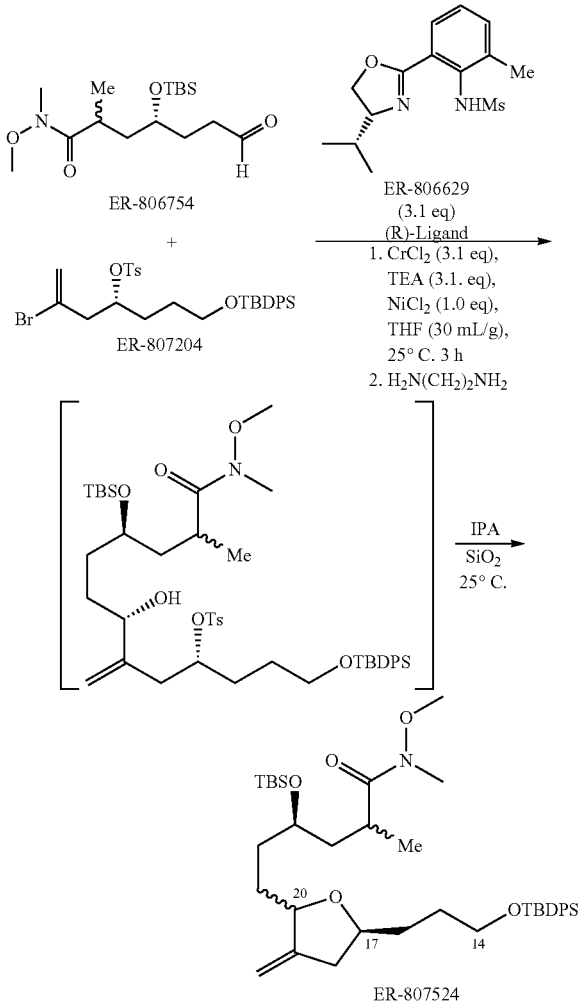

A reactor was charged with ER-806629 (1.53 wt., 3.1 eq.) and THF (10.5 vol.) and the solution was degassed with nitrogen sparge for 60 minutes. A second inserted reactor was charged with ER-807204 (1 wt., 1.0 eq.), ER-806754 (0.66 wt., 1.2 eq.) and THF (2.7 vol.) and this solution was degassed with argon sparge for 45 minutes. The reactor containing ER-806629 was charged with $CrCl_2$ (0.63 wt., 3.1 eq.) and followed by $Et_3N$ (0.52 wt., 3.1 eq.). The dark green suspension was stirred at an internal temperature of 30 to 35° C. for 1 hour, cooled to 0 to 5° C. and then $NiCl_2$ (0.1 eq.) was added. The first reactor was charged with the contents of the second reactor slowly over 0.5 hours and the reaction allowed to warm to rt. The reaction was cooled to an internal temperature of 0° C. then ethylenediamine (1.0 wt., 10 eq.) was added over 30 minutes and the reaction stirred at an internal temperature of 25° C. for at least 30 minutes. To the reaction was added water (4 vol.), TBME (10 vol.) and n-heptane (1 vol.) and the resulting mixture stirred for 15 minutes and the phases allowed to separate (~30 min). The aqueous phase was separated and back extracted with TBME (~7.5 vol.). The organic layers were combined and washed with water (5 vol.), brine (3 vol.), and concentrated in vacuo to minimum volume. To the crude mixture was added IPA (10 vol.) and $SiO_2$ (1 wt.) and the resulting mixture stirred at an internal temperature of 25° C. for up to 4 days. The slurry was filtered and the filter cake washed with IPA (2×1 volume). To the filtrate was added n-heptane (6.6 vol.) and the mixture was concentrated in vacuo until a suspension formed. The mixture was filtered and the cake washed with n-heptane then the mixture was concentrated in vacuo. The crude product was purified via $SiO_2$ column chromatography to yield ER-807524 (0.54 wt., 0.48 eq.), as a clear yellow oil. IR (thin film, cm-1) λ 2934, 1668, 1471, 1108, 833. LRMS m/z 704 (M+Na).

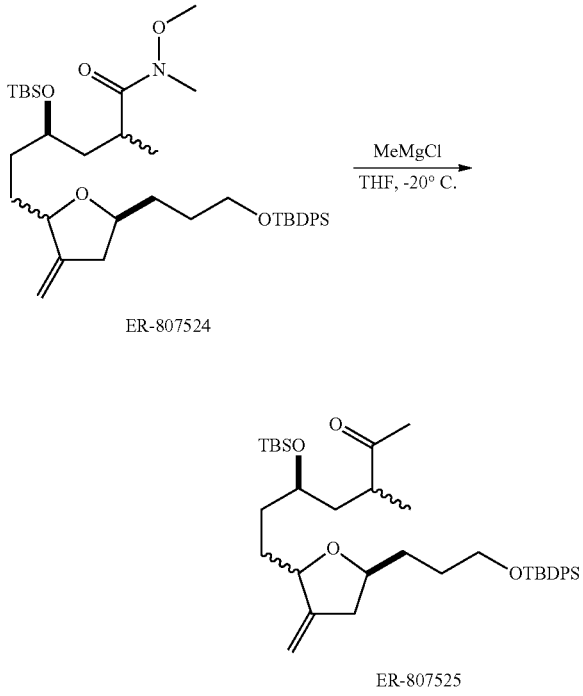

A reactor was charged with ER-807524 (1 wt., 1 eq.) and anhydrous THF (1.25 vol.). The mixture was cooled to an internal temperature of −20° C. and 3 M methyl magnesium chloride (0.59 vol., 1.2 eq.) was added at a rate such that the internal temperature did not exceed 0° C. Upon complete addition, the mixture was warmed to an internal temperature of 0° C. over 2 hours. The reaction mixture was inverse quenched into semi-saturated ammonium chloride (2.62 vol.) and the resulting mixture diluted with TBME (2 vol.) with vigorous mixing. The aqueous layer was discarded and the organics washed with brine (2 vol.) then concentrated in vacuo. The crude product was purified via $SiO_2$ column chromatography to yield ER-807525 (0.79-0.82 wt., 0.85-0.88 eq.) as yellow oil.

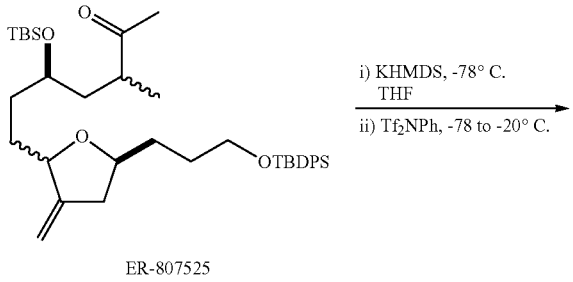

-continued

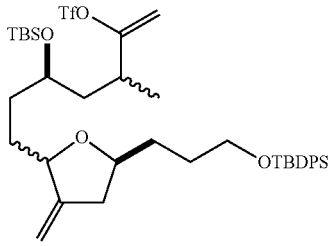

ER-807526

A reactor was charged with ER-807525 (1 wt., 1 eq.), N-phenylbistrifluoromethanesulfonamide (0.59 wt., 1.1 eq.), and anhydrous THF (4.1 vol.) and the mixture cooled to an internal temperature of −75° C. 0.5 M KHMDS in toluene (2.75 wt., 1 eq.) was added at a rate such that internal temperature did not exceed −60° C. then the reaction was warmed to −20° C. over 2 hours. The reaction was quenched with semi-saturated $NH_4Cl$ (2.4 vol.) at a rate such that internal temperature did not exceed 0° C. The mixture was warmed to an internal temperature of 20° C. and n-heptane (2.4 vol.) was added. The mixture was stirred and the aqueous layer was separated and discarded. The organic layer was washed three times with saturated sodium bicarbonate (2.3 vol. each) then concentrated in vacuo to yield ER-807526 (1.2-1.4 wt., 1.0-1.2 eq.). The material was utilized in the next stage without further purification.

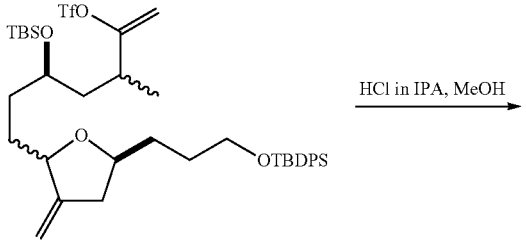

ER-807526

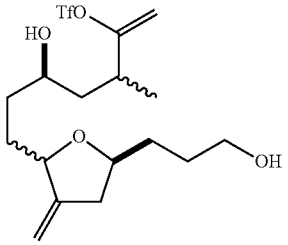

ER-807527

A reactor was charged with ER-807526 (1 wt., 1 eq.) and anhydrous methanol (3 vol.) at 20° C. 1.25M HCl in IPA (4 vol., 5 eq.) was added and the mixture stirred for 3 hours. Solid $NaHCO_3$ (0.42 wt., 5 eq.) was added portion-wise with stirring until the pH of the reaction mixture reached 6-7. The reaction mixture was filtered with methanol (3×2 vol.) washes. All filtrates were concentrated in vacuo and then purified via $SiO_2$ column chromatography to yield ER-807527 (0.43 wt., 0.79-0.85 eq.).

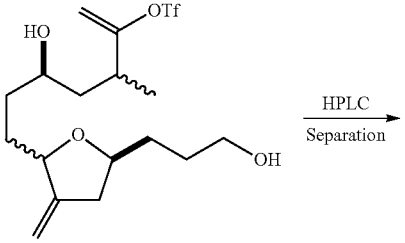

ER-807527

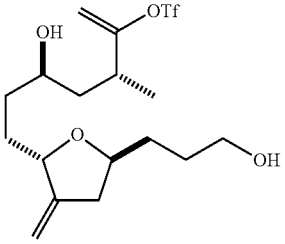

ER-806730

The diastereomeric mixture of ER-807527 was separated by preparative HPLC chromatography and the desired fractions concentrated to yield ER-806730 (0.56 wt., 0.56 eq.) as a clear yellow oil. The preparative HPLC chromatography protocol used to isolate ER-806730 is as follows.

| | |
|---|---|
| Column and Media: | Kromasil spherical silica 60 Å, 10 μm particle size packed to 7.7 cm (diam.) × 30 cm (length) in a 7.7 cm × 60 cm Varian Dynamax Rampak column. |
| HPLC Packing Station: | Varian (Rainin) Dynamax Rampak 41/77 mm Column Packing Station |
| HPLC Pumps: | Varian (Rainin) SD-1 Titanium Pump Heads |
| Primary HPLC Detector: | Waters R403 Refractive Index detector |
| Secondary HPLC Detector: | Varian (Rainin) UV-1 detector with preparative flow cell |
| Chromatography Control and Acquisition Software: | Varian (Rainin) Dynamax DA version 1.4.6 |
| Chromatography Data Processing Software: | Varian (Rainin) Dynamax R version 1.4.3 |
| Mobile Phase: | 28.5:63.7:7.85 (vol/vol) n-heptane: methyl tert-butyl ether:2-propanol |
| Flow Rate: | 140 mL/min |
| Column Temperature: | Ambient (25° C.) |
| Detection: | Refractive Index, negative polarity at 16 X affenuation and UV at 215 nm. |
| Mobile Phase Gradient: | Isocratic |
| Run Time: | 40 minutes |
| Injection Volume: | 10 ml of 0.8 g/mL of ER-807527 |

The above protocol was used to separate the diastereomers of ER-807527 in the following manner. Each lot of ER-807527 was first diluted to 0.1 g/ml in the mobile phase and filtered under vacuum through a 47 mm, 1 μm pore size, glass fiber filter (Whatman GFC). The filtrate was then concentrated under vacuum on a rotary evaporator. Flow on the SD-1 HPLC pump A (primed and purged with mobile phase) was initiated and the flow rate gradually increased to 140 mL/minute. The system was washed until the UV and RI detectors achieved a stable baseline. The RI detector reference flow cell was flushed with fresh mobile phase.

Chromatography of 8 g injections of ER-807527 was accomplished by diluting the current lot of ER-807527 to a concentration of 0.8 g/mL in the mobile phase. Injecting 10 mL aliquots of the dissolved material and collecting the eluant corresponding to the ER-806730 peak approximately beginning at the peak apex approximately 24 minutes and continuing to 35 minutes. Subsequent injections and fraction collection were continued until the starting material is exhausted.

The fractions corresponding to ER-806730 were pooled and concentrated under vacuum on a rotary evaporator. The diastereomeric purity and area-% purity area were assessed using the HPLC analytical method described in Table 2.

TABLE 2

| HPLC Analysis of Diastereomeric Purity of ER-806730: | |
|---|---|
| Column: | Kromasil [Slica] *Silica* 250 × 4.6 mm, 5 μm, MetaChem cat. no. 0475-250X046 |
| Flow rate: | 1 mL/min |
| Temp. (° C.): | 27 |
| Inj. Vol.: | 10 μL, sample in Solvent A, 2.5 mg/mL |
| Instrument: | Waters Alliance W2690 with UV W2487 |

| Mobile Phase Constituents: | |
|---|---|
| A | 30:67:3 n-Heptane:Methyl tert-Butyl Ether:2-Propanol |
| B | 2-Propanol |
| C | |
| D | |

| Gradient Table: | (%) | | | | Gradient |
|---|---|---|---|---|---|
| Time (min) | A | B | C | D | |
| 0 | 100 | 0 | 0 | 0 | isocratic |
| 22 | 100 | 0 | 0 | 0 | isocratic |
| 26 | 90 | 10 | 0 | 0 | linear |
| 32 | 90 | 10 | 0 | 0 | isocratic |
| Run time | 32 min with 18 min re-equilibration time at initial conditions | | | | |

Detection: Absorbance at 205 nm UV

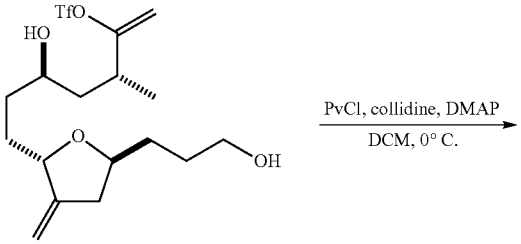

ER-806730

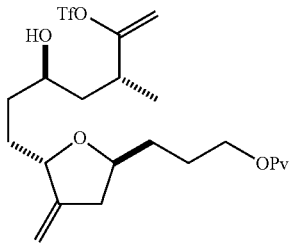

ER-806732

A reactor was charged with ER-806730 (1 wt., 1 eq.) and anhydrous dichloromethane (4.8 vol.) and cooled to an internal temperature of 0° C. 2,4,6-Collidine (1.16 wt., 4 eq.) and DMAP (0.03 wt., 0.1 eq.) were added and the resulting mixture stirred for 15 minutes and then trimethylacetyl chloride (0.3 wt., 1.05 eq.) was added at a rate such that internal temperature did not exceed 10° C. Water (3 vol.) was added and the mixture stirred for 15 minutes. TBME (10 vol.) was added and the mixture stirred for an additional 10 minutes. The organic layer was washed with 1N HCl (10 vol.) washing until a negative result for 2,4,6-collidine is obtained then with water (5 vol.), saturated sodium bicarbonate (5 vol.), and saturated brine (5 vol.), respectively. The organic layer was concentrated in vacuo and the concentrate purified via $SiO_2$ column chromatography to yield ER-806732 (1.02 wt., 0.85 eq.) as a yellow oil.

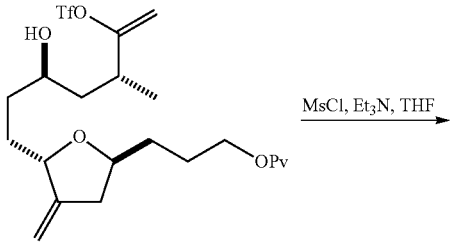

ER-806732

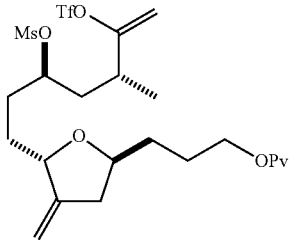

ER-805973

A reactor was charged with ER-806732 (1 wt., 1 eq.) and anhydrous THF (2.35 vol.) and cooled to an internal temperature of 0° C. Triethylamine (0.22 wt., 1.1 eq.) was added followed by methanesulfonyl chloride (0.24 wt., 1.05 eq.) at a rate such that internal temperature did not exceed 10° C. The reaction was stirred at an internal temperature of 0° C. then n-heptane (3.4 vol.) was added with vigorous stirring and the layers were allowed to partition. The organics were washed with saturated brine (3.4 vol.), dried over saturated sodium sulfate (2 wt.), filtered and the cake washed with n-heptane until a negative result for ER-805973 (F-2a) was obtained. The filtrates were concentrated in vacuo to obtain ER-805973 (1.12 wt., 0.97 eq.). The crude ER-805973 (F-2a) was used in the next stage without further purification. IR (thin film, cm-1) λ 2961, 1725, 1413, 1208, 926. LRMS m/z 579 (M+H).

Example 3

Alternate Preparation of ER-806730

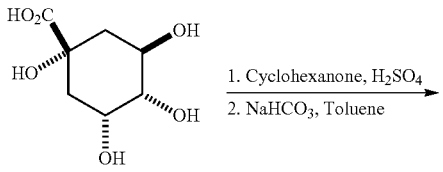

quinic acid

-continued

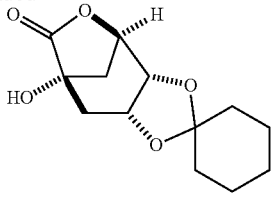

1

Quinic acid (1 wt), cyclohexanone (2.11 eq, 1.08 wt), and conc. sulfuric acid (0.011 eq, 0.0056 wt) were added to a reactor. The reaction mixture was heated to 160° C. and water was removed by azeotropic distillation (azeotrope begins at 100° C.). The reaction was cooled to 90° C. to 100° C. and sodium bicarbonate (0.0096 wt) and toluene (3.6 wt) were added. The reaction was cooled to ambient temperature over 4-6 hours and the resulting precipitate was filtered, washed with toluene (2×0.9 wt), and dried to provide 1 (0.97 wt) as a white powder.

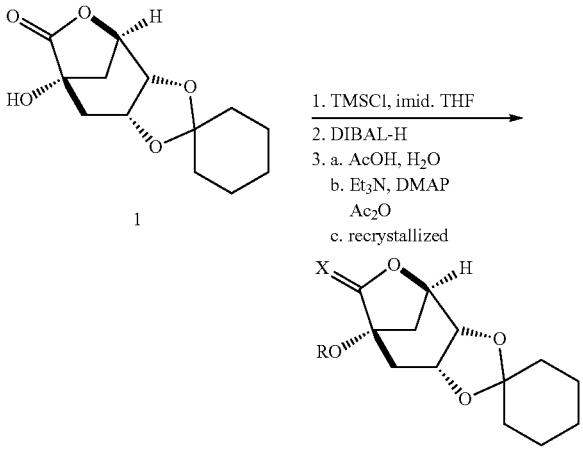

1

2a, X = O;
2b, X = H, OH;
2c, X = H, OAc;
R = TMS
R = TMS
R = Ac

Compound 1 (1 eq, 1 wt) and imidazole (2.5 eq, 0.80 wt) were combined, purged with $N_2$, and suspended in anhydrous THF (10 v). TMSCl (1.2 eq, 0.61 wt) was added at a rate that maintained the temperature below 30° C. The reaction was cooled to ambient temperature, heptane (10 v) was added and the resulting suspension filtered. The filter cake was washed with 1:1 hpt/THF (10 v) the filtrate solvent was exchanged with toluene by atmospheric distillation to provide a solution of 2a (calcd. at 1.34 wt) in toluene (~5 wt).

The solution of 2a was cooled to −78° C. and DIBAL-H (1.5 M in toluene, 1.2 eq, 2.1 wt) was added at a rate that maintained the temperature below −65° C. The excess DIBAL-H was quenched with MeOH (0.3 eq, 0.034 wt) and the solution warmed to 0° C. The solution was transferred to a solution of 30% wt/wt aqueous Rochelle salt (10 wt) and sodium bicarbonate (1 wt) at a rate that maintained the temperature below 25° C. The mixture was stirred vigorously to obtain a biphasic solution. The layers were separated and the aqueous layer was extracted with MTBE (5v). The combined organic layers were washed with water (2.5 wt) and then saturated brine (2.5 wt). The organics were concentrated and solvent exchanged with THF to provide a solution of 2b (calcd. at 0.98 wt) in THF (5 v).

The solution of 2b was cooled to 5° C. and acetic acid (2.9 eq, 0.51 v) was added. Water (1.0 eq, 0.055 v) was added and the solution stirred at 0° C. to 5° C. Up to two additional aliquots of acetic acid and one aliquot of water were added as needed to facilitate deprotection of the silyl group. $Et_3N$ (12 eq, 3.6 wt) and DMAP (0.05 eq., 0.02 wt) were added at a rate that maintained the temperature below 20° C. Acetic anhydride (6 eq, 2.0 wt) was added and the reaction stirred at rt. The reaction was cooled to 5° C. and added to saturated aqueous sodium bicarbonate (10 v) at a rate that maintained the temperature below 30° C. The resulting mixture was allowed to stir for 3-4 hours and the layers allowed to separate. The aqueous layer was extracted with MTBE (5 v) and the combined organics were washed with water (5 v). The extracts were solvent exchanged with IPA by distillation to provide a solution of 2c in IPA (3 v). The solution was cooled to 5° C. and the resulting crystals were filtered. The mother liquor was concentrated and a second crop obtained after recrystallization to provide 2c (0.87 wt) as a white crystalline solid.

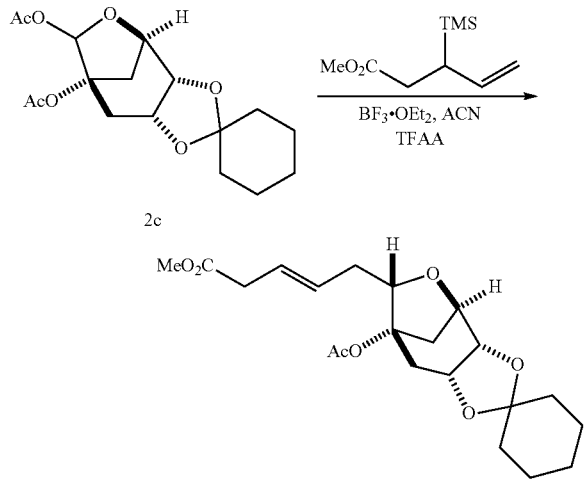

2c

3

2c (1 wt) was dissolved in acetonitrile (6 v) and methyl 3-trimethylsilylpent-4-eneoate (3.0 eq, 1.86 wt) was added followed by TFAA (0.2 eq, 0.083 v). $BF_3 \cdot OEt_2$ (1.0 eq, 0.42 v) was then added to the solution at a rate that maintained the temperature below 25° C. The reaction was added to saturated aqueous sodium bicarbonate (10 v) and the resulting mixture stirred for 15 minutes. The mixture was extracted with heptane (10 v), followed by MTBE (5 v) and the combined extracts were concentrated to provide 3 (calcd. at 0.72 wt) as an orange oil.

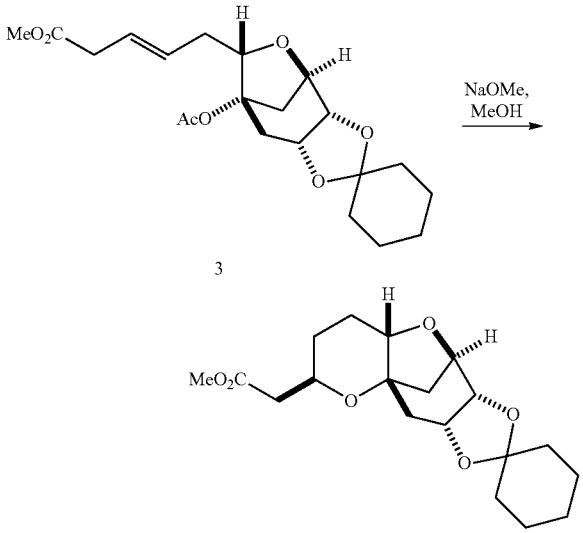

A solution of 3 (1 wt) in THF (9 v) was treated with sodium methoxide (25% wt/wt in methanol (1.5 eq, 2.2 wt)) at a rate that maintains the temperature below 25° C. The reaction was quenched by addition to 1 N HCl (10 v). The organic layer was separated and the aqueous was extracted with MTBE (10 v). The combined organics were washed with water (2.5 v), saturated sodium bicarbonate (2.5 v), and water (2.5 v). The solution was concentrated to provide a solution of 4 (calcd. at 0.88 wt) in THF (2.5 v). The solution was used directly in the next step.

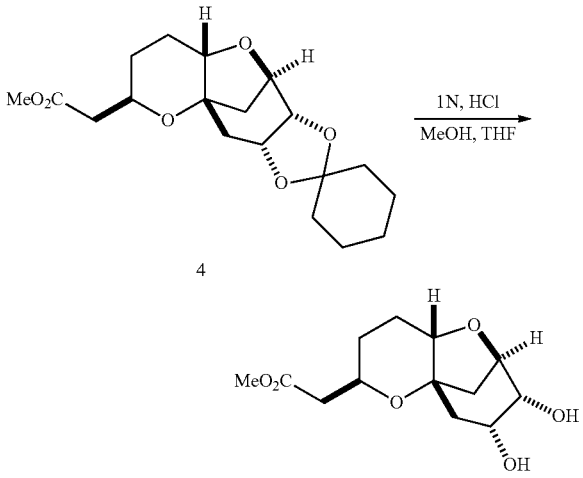

Methanol (5 v) was added to the solution of 4 (1 wt) in tetrahydrofuran (2.5 v). 1N HCl (0.75 eq, 2 v) was added and the reaction was warmed to 60-80° C. The reaction was cooled to rt and added to saturated aqueous bicarbonate. The mixture was extracted with DCM (3×2.5 v) and the combined DCM extracts were solvent exchanged with EtOAc to provide a solution of 5 in EtOAc (3 v). Heptane (2 v) was added to induce crystallization and the resulting suspension cooled to 0° C. The solids were collected by filtration and the filter cake washed with cold EtOAc/heptane (1:1 v/v) and dried to provide 5 (0.55 wt) as a white powder.

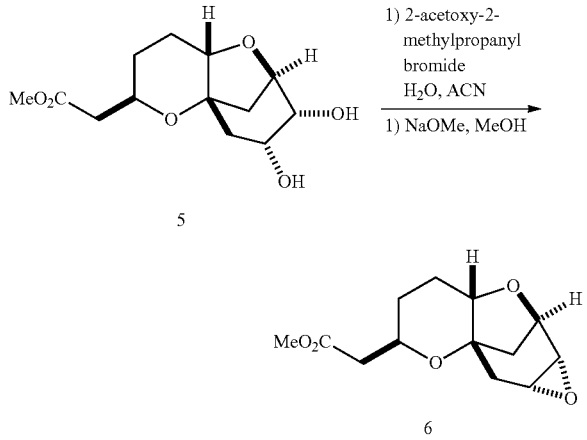

Compound 5 (1 wt) was dissolved in ACN (10 v) then 2-acetoxy-2-methylpropanyl bromide (4.0 eq, 2.2 wt) and water (1 eq, 0.067 wt) were added consecutively. The resulting mixture was stirred at ambient temperature then cooled to 5-10° C. NaOMe (25% wt/wt in MeOH, 8 eq, 6.2 wt) was added and the reaction allowed to warn to ambient temperature. The reaction was quenched by the addition of saturated sodium bicarbonate (10 v) and extracted with MTBE (2×10 v). The solvent was exchanged with methanol by atmospheric distillation to provide a solution of 6 (calcd at 0.91 wt) in methanol (10 v).

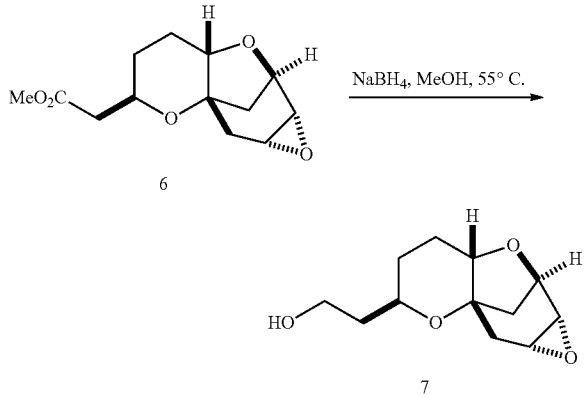

A solution of 6 (1 wt) in methanol (10 v) was heated to 55° C. Sodium borohydride (5 eq, 0.68 wt) was added in 6 portions and the reaction cooled to 5° C. and quenched with 1 N HCl (10 v). Brine (5 v) was added and the reaction extracted with EtOAc (2×10 v). The extracts were combined and concentrated to provide 7 as a tan residue.

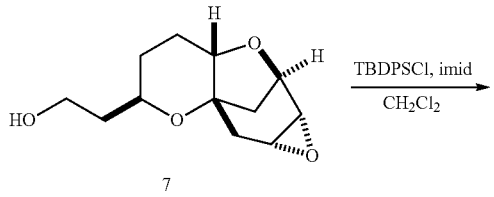

-continued

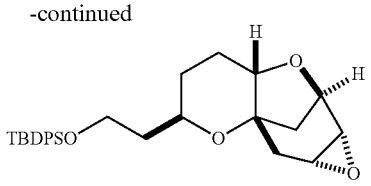

8

Compound 7 (1 wt) was dissolved in $CH_2Cl_2$ (10 v) then DMAP (0.1 eq, 0.054 wt), $Et_3N$ (3.0 eq, 1.85 v), and TBDP-SCl (1.2 eq, 1.38 v) were added at ambient temperature. Sodium bicarbonate (10 v) was added and the organic layer separated. The aqueous layer was extracted again with $CH_2Cl_2$ (10 v), the organic extracts combined and concentrated to provide 8 (calculated at 1.8 wt) as a colorless oil.

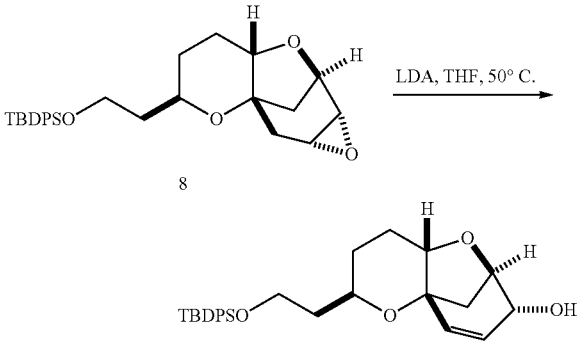

8

9

LDA (1.5 M in cyclohexane, 4 eq, 6 v) was added to a solution of 8 (1 wt) in THF (10 v) at ambient temperature. The solution was warmed to 50° C. then quenched with 1 N HCl (5 v) and extracted with MTBE (10 v). The extracts were concentrated to provide 9 (0.9 wt) as an oil.

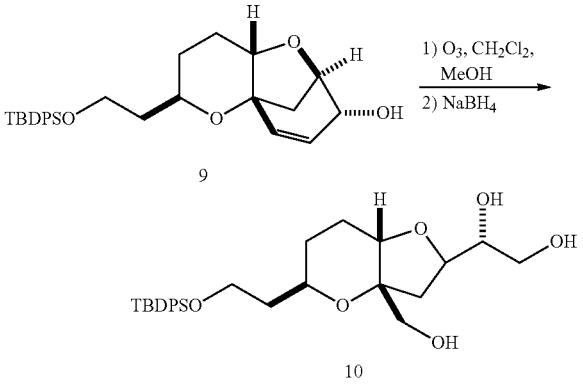

9

10

A solution of 9 (1 wt) in $CH_2Cl_2$ (5 v) in MeOH (5 v) was cooled to −60° C. and treated with $O_3$ keeping temperature below −50° C. The reaction was purged with $N_2$, $NaBH_4$ (0.5 eq, 0.04 wt) was added and the mixture warmed to 0° C. Additional $NaBH_4$ (1 eq, 0.08 wt) was added in portions and the reaction allowed to warm to ambient temperature. After 3 hours, the mixture was quenched with 1N HCl, (10 v), $CH_2Cl_2$ (5 v) was added and the layers were allowed to partition. The aqueous layer was re-extracted with $CH_2Cl_2$ (10 v) and the organic extracts were combined and concentrated to provide 10 (0.97 wt) as a colorless oil.

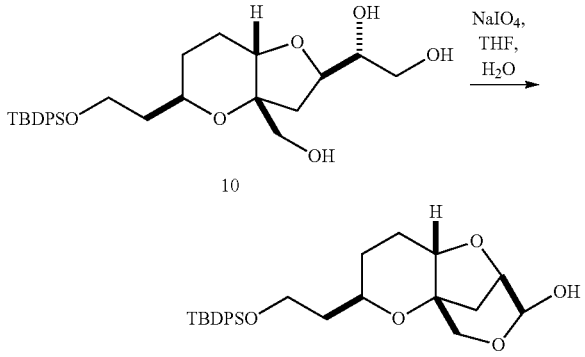

10

11

Compound 10 was dissolved in THF (10 v) and phosphate buffer (pH=7, 5 v) was added. $NaIO_4$ (2 eq, 0.854 wt) was added and the reaction warmed to ambient temperature. Water (5 v) and MTBE (10 v) were added and the resulting mixture was stirred vigorously for 10 minutes. The organic layer was separated and washed with 10% wt/v aqueous sodium thiosulfate (5 v), water (5 v), and brine (5 v) then dried by azeotropic distillation with THF (~200 ppm water) to provide a solution of 11 (calcd. at 0.93 wt) in THF (10 v). This solution was used directly in next step.

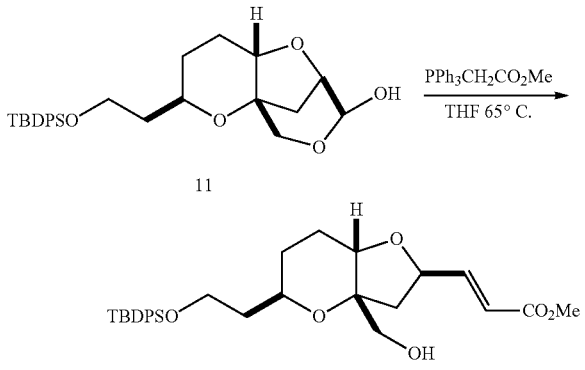

11

12

(Carbomethoxymethylene)triphenylphosphorane (1 wt) was added to the solution of 11 (1 wt) in THF (10 v) and heated to 65° C. Heptane (40 v) was added and the resulting mixture stirred for 30 minutes. The resulting precipitate was filtered and the filtrate concentrated to a total 10 v. $SiO_2$ (5 wt) was added and the suspension filtered over a pad of $SiO_2$ eluting with MTBE (20-40 v). The solvent was exchanged with MeOH to provide a solution of 12 (calcd. at 0.95 wt) in MeOH (10 v) which was used directly in the next step.

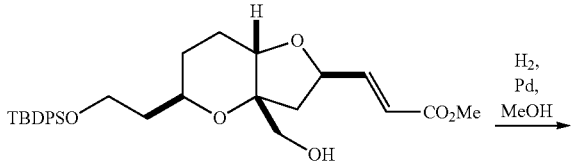

12

-continued

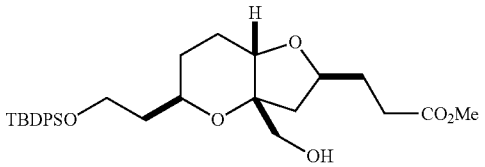

13

A solution of 12 (1 wt) in MeOH (10 v) was added to 10% Wt/wt Pd(C) (0.23 eq, 0.37 wt) and treated with $H_2$. The suspension was filtered while rinsing the filter cake with THF (10 v). The solvent was exchanged with THF to provide a solution of 13 (calcd. at 0.95 wt) in THF (10 v) which was used directly in the next step.

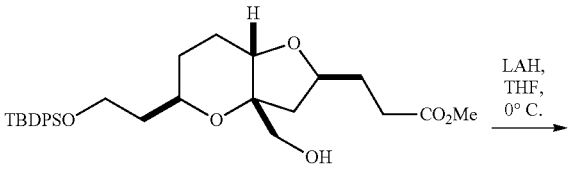

13

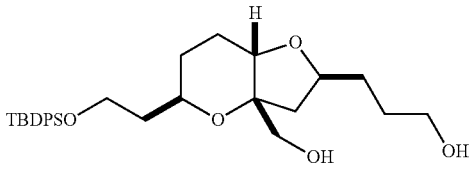

14

The solution of 13 (1 wt) in THF (10 v) was cooled to 0-5° C. and LAH (1 M (THF), 0.78 eq, 1.5 v) was added at a rate that maintained the temperature below 10° C. Water (1.7 eq, 0.06 v) was then added at a rate that maintained the temperature below 10° C. NaOH (10% wt/wt in water, 0.16 eq, 0.06 v) was added followed by water (4.98 eq, 0.17 v) at a rate that maintained the temperature below 10° C. and the resulting mixture stirred vigorously while warming to ambient temperature. The suspension was filtered and the filter cake rinsed with THF (5 v). The filtrate was partially concentrated to provide 14 (calcd. at 0.9 wt) in THF (10 v) which was used directly in next step.

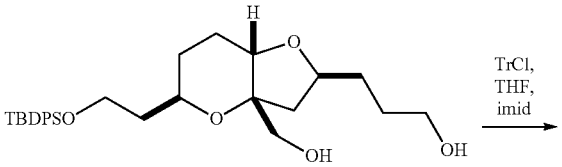

14

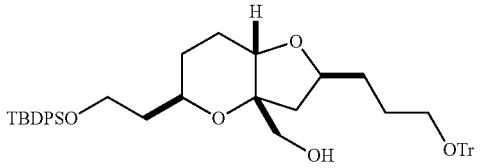

15

The solution of 14 (1 wt) in THF (10 v) was cooled to 0° C. then imidazole and TrCl (1.5 eq, 0.59 wt) were added. Saturated aqueous $NaHCO_3$ (5 v) was added and the mixture extracted with heptane (10 v). The extract was washed with brine (10 v) and concentrated to provide 15 (1.35 wt).

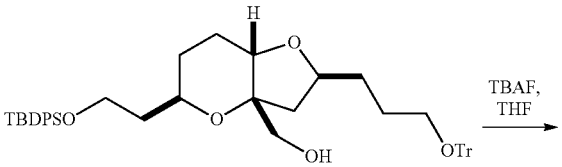

15

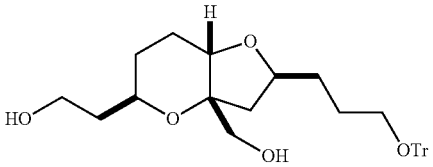

16

Compound 15 (1 wt) was dissolved in THF (10 v) and treated with TBAF (1M, 1.2 eq, 1.6 v). The reaction mixture was concentrated to 2 v then heptane (5 v) and $SiO_2$ (5 wt) were added. The resulting suspension was filtered and eluted with heptane (5 v) followed by THF (10 v). The THF eluent was collected to provide a solution of 16 (calcd at 0.61 wt) in THF (10 v) which was used directly in the next step.

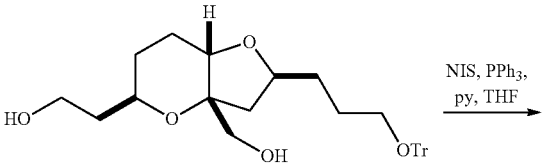

16

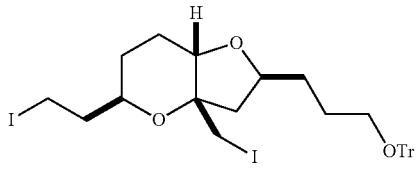

17

$PPh_3$ (5 eq, 2.3 wt), pyridine (10 eq 1 vol), and NIS (3.0 eq, 1.1 wt) were added to the solution of 16 (1 wt) in THF (10 v). 20% wt/wt aqueous citric acid (10 eq, 14 wt) was then added and the resulting mixture allowed to stir for 10 minutes. The reaction was diluted with heptane (10 v) and the aqueous layer separated. The organic layer was washed with water (5 v), 10% wt/v aqueous sodium thiosulfate (5 v), water (5 v) and brine (5 v). The solvent was exchanged with EtOH and concentrated to 5 v. Water (10 v) was added and the resulting precipitate was collected by filtration to obtain 17 (0.65 wt) as a white solid.

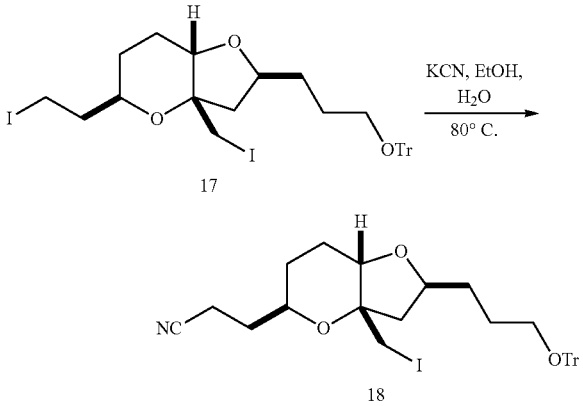

Compound 17 (1 wt) and KCN (6 eq, 0.54 wt) were suspended in EtOH (5 v) and water (10 v) and the resulting suspension heated to 80° C. The reaction was diluted with water (5 v) and EtOAc (10 v) and mixed for 10 minutes. The aqueous layer was removed and the organic layer washed with water (5 v) and brine (5 v). The solvent was exchanged with EtOH to provide 18 (0.75 wt) in EtOH (10 v) which was used directly in next step.

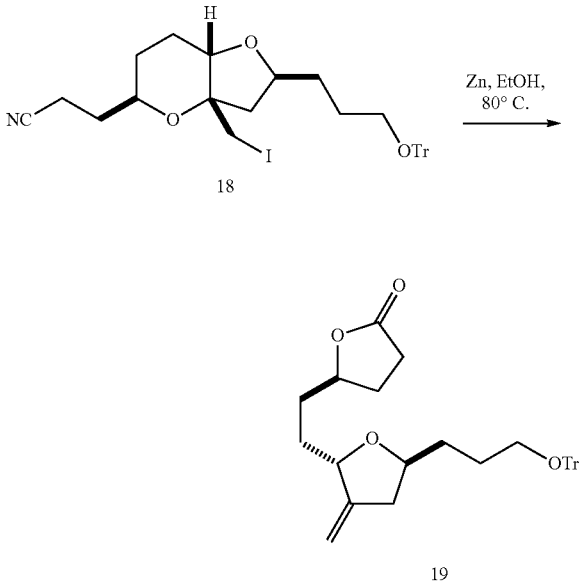

Zn (37 eq, 3.9 wt) was added to the solution of 18 (1 wt) in EtOH (10 v) and the mixture heated to 75-80° C. The reaction was partially concentrated to 2-3 v, cooled to ambient temperature, and partitioned between MTBE (10 v) and water 5 (v). The aqueous layer was removed and the organic layer washed with saturated bicarbonate (5 v), water (5 v), and brine (5 v), then dried by THF azeotropic distillation to ~200 ppm water to provide 19 (0.81 wt) in THF (10 v). The resulting solution was used directly in next step.

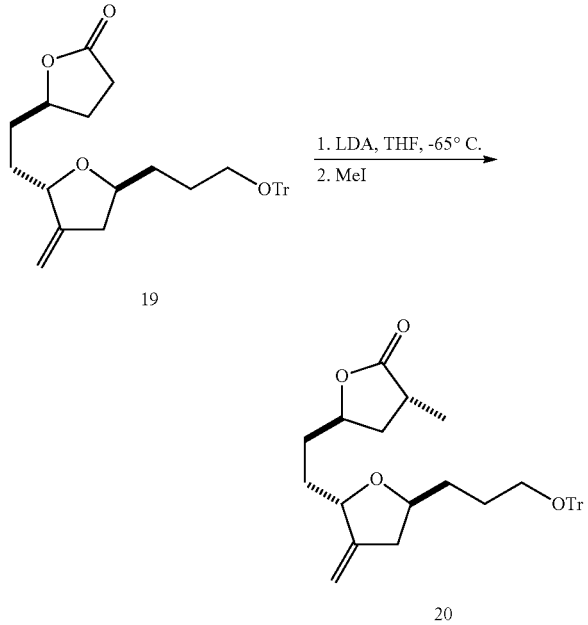

LDA (1.0 M in THF, 1.2 eq, 2.4 v) was added to the solution of 19 (1 wt) in THF (10 v) at −78° C. The resulting mixture was stirred for 10 minutes then the enolate solution was added to a solution of MeI (1.5 eq, 0.19 v) in THF (5 v) at −78° C. The reaction was inverse quenched into saturated sodium bicarbonate (10 v) and extracted with MTBE (15 v). The extract was washed with brine (5 v), concentrated, then purified by chromatography to provide 20 (0.86 wt).

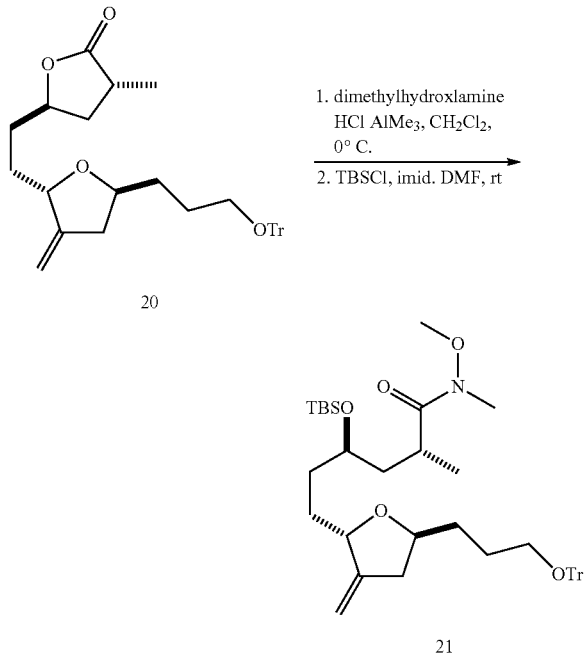

$AlMe_3$ (2 M in toluene, 1.5 eq, 1.5 v) was added to a suspension of dimethylhydroxylamine hydrogen chloride (1 wt) in $CH_2Cl_2$ (2.5 v) at 0° C. A solution of 20 (1 wt) in $CH_2Cl_2$ (5 v) was added at a rate that maintained the reaction temperature below 5° C. The reaction mixture was then added to aqueous sodium tartrate (1.3 M, 20 v) keeping the temperature below 10° C. The layers were allowed to partition, were separated, and the organic layer was dried with $Na_2SO_4$ (5 wt). The resulting suspension was filtered and the filtrate concentrated. The residue was dissolved in DMF (2 v) then imidazole (0.19 wt) and TBSCl (0.29 wt) were added. The reaction was diluted with water (5 v) and MTBE (10 v) and allowed to stir for 10 minutes. The aqueous layer was removed and the organic layer washed with water (5 v). The extract was added to a solution of aqueous NaOH (1N, 0.78 v) and MeOH (0.7 v). The reaction was allowed to stir then the aqueous layer was removed and the organic washed with brine (2.5 v) then concentrated to provide 21 (1.2 wt).

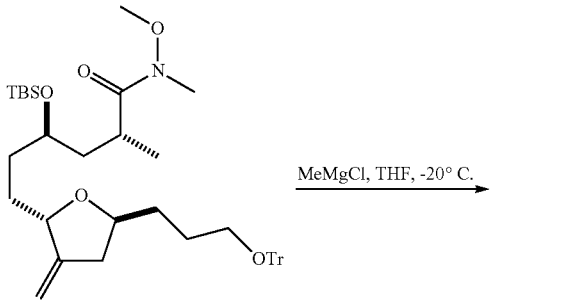

21

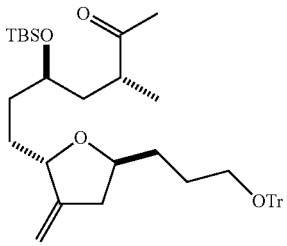

22

Methyl magnesium chloride (3.0 M, 59 wt, 1.2 eq) was is added to a solution of 21 (1 wt) in anhydrous THF (1.11 wt, 1.25 v) at a rate that maintained the reaction temperature below 0° C. After stirring at 0° C., the reaction was reverse quenched into saturated ammonium chloride (2.5 v) and water (2.3 v). The resulting mixture was diluted with MTBE (10 v) and stirred vigorously. The aqueous layer was separated and the organic layer washed with brine (2.5 v) and concentrated to provide 22 (0.84 wt).

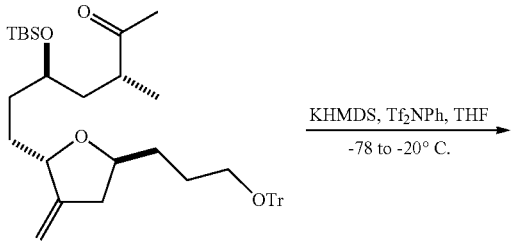

22

-continued

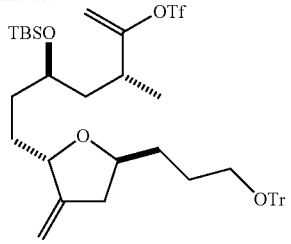

23

Compound 22 (1 wt) was dissolved in THF (4 v) and cooled to −78° C. KHMDS (1.5 M in toluene, 1.01 eq, 2.78 wt,) was added while maintaining the temperature below −60° C. A solution of $Tf_2NPh$ (0.62 wt, 1.1 eq) in THF (1.5 v) was added and the reaction warmed to −20° C. Saturated ammonium chloride (2.5 v), water (2.5 v), and n-heptane (2.5 v) were added and the mixture warmed to ambient temperature. The layers were allowed to partition and the aqueous layer removed. The organic extract was washed with saturated aqueous sodium bicarbonate (3×2.5 v) and brine (2.5 v) then concentrated in vacuo to provide 23 (1.1 wt).

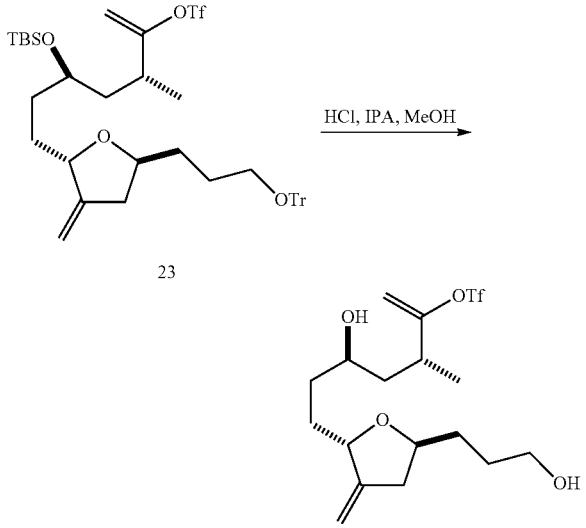

23

24
ER-806730

Compound 23 was dissolved in MeOH (2.5 v) and cooled to 15° C. HCl (5N in IPA, 1.30 eq, 1.18 wt) was added and the resulting solution allowed to warm to 25° C. The reaction was cooled to 0° C. and sodium bicarbonate (3 eq, 0.33 wt) was added. The reaction was stirred for 15 minutes and the resulting precipitate removed by filtration. The filter cake was washed with ACS grade methanol (1 v) and filtrates were combined and concentrated. The crude concentrate was purified by chromatography to provide ER-806730 (24) (0.5 wt).

Example 4a

Example 4a provides an alternate method of preparing compounds of formula A, an intermediate to F 2, using the general scheme set forth at Scheme V above. This method uses ER-812935 as an intermediate as prepared according to Example 3 (compound 4), above.

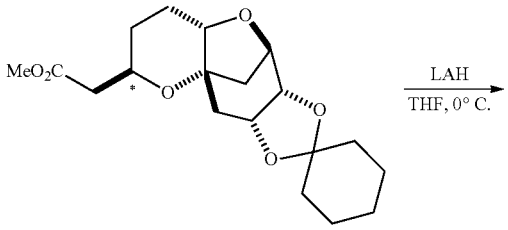

ER-812935
*9:1 C.23 diastereomers

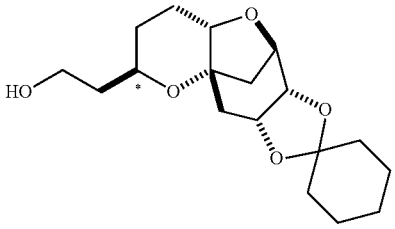

ER-817633
*9:1 C.23 diastereomers

ER-812935 (1 wt) was dissolved in THF (10 v) and cooled to 0° C. LAH (1.0 M in THF, 0.70 eq, 2.0 v) was added keeping the temperature below 5° C. While stirring vigorously, excess reagent was quenched with water (0.078 v) keeping the temperature below 5° C. While maintaining the vigorous stirring, NaOH (15% wt/wt in water (0.078 v)) was added followed by water (0.18 v). After adding Celite® (2 wt), the suspension was filtered and the cake rinsed with THF (5 v). The solution of ER-817633 (0.92 wt, calcd. based on 100% conversion) was concentrated to 5 v and used directly in the next stage.

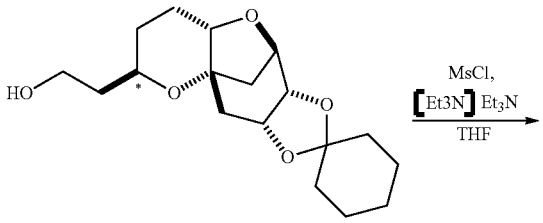

ER-817633
*9:1 C.23 diastereomers

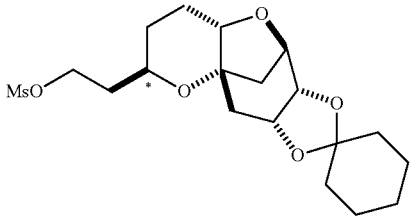

ER-818937
*9:1 C.23 diastereomers

The previously prepared solution of ER-817633 (1 wt in 5 v THF) was diluted with THF (5 v), cooled to 5° C. and $Et_3N$ (3 eq., 0.94 wt) was added. MsCl (1.05 eq, 0.25 v) was added at a rate that maintained the temperature below 10° C. The reaction was quenched by addition of water (5 wt). Heptane (8 v) was added and the mixture allowed to partition. The aqueous phase was separated and extracted with MTBE (2 v). The combined organic extracts were washed with saturated sodium bicarbonate (5 v) and water (1.9 v) The organic layer was concentrated and solvent exchanged with EtOH to prepare a solution of ER-818937 (1.23 wt calcd. based on 100% conversion) in EtOH (1 v) which was used directly in the next stage.

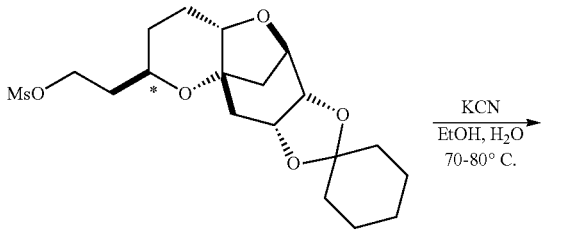

ER-818937
*9:1 C.23 diastereomers

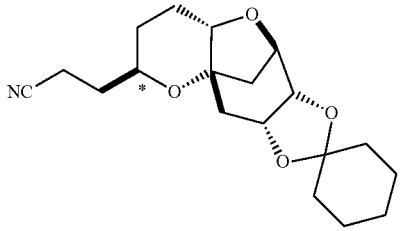

ER-818950
*9:1 C.23 diastereomers

The previously prepared solution of ER-818937 (1 wt in EtOH (0.8 v) is diluted with EtOH (190 proof, 9 v). KCN (3 eq., 0.41 wt) was added and the suspension was heated to 70-80° C. The reaction was cooled to ambient temperature and water (10 v) was added followed by MTBE (10 v). The layers were separated and the aqueous extracted with MTBE (5 v). The combined organics are washed with water (2 v) and saturated brine (4 wt). The extracts were concentrated and used directly in the next stage.

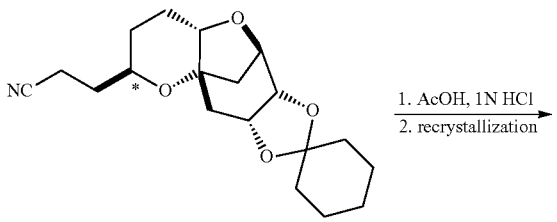

ER-818950
*9:1 C.23 diastereomers

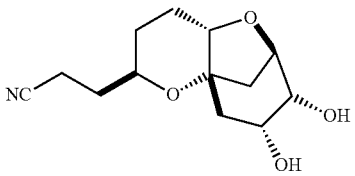

ER-817664
single diastereomer

ER-818950 was dissolved in acetic acid (5 v) and hydrogen chloride (1.0 M, 1 eq, 3 v) was added and the reaction was stirred at ambient temperature. The reaction was cooled to 0° C. and NaOH (50% wt/wt, 30 eq, 7 wt) was added at a rate that maintained the temperature below 10° C. The solution was extracted with heptane (2×10 vol). The aqueous phase was saturated with NaCl and extracted with ACN (2×10 v). The combined ACN extracts were concentrated and solvent exchanged with EtOAc by atmospheric distillation to provide a solution of ER-817664 in EtOAc (3 v). Salts were filtered from the hot solution which was then cooled to 0° C. The suspension was filtered to provide ER-817664 as a white crystalline solid.

Example 4b

Example 4b provides an alternate method of preparing compounds of formula F-2 using the general scheme set forth at Schemes Vb and Vc above. This method uses ER-817664 as an intermediate as prepared according to Example 4a, above.

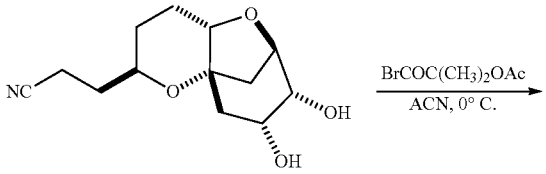

ER-817664
$C_{13}H_{19}NO_4$
Exact Mass: 253.1314
Mol. Wt.: 253.2943

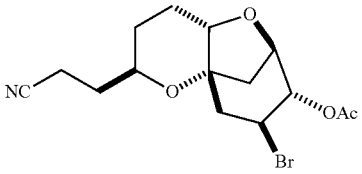

$C_{15}H_{20}BrNO_4$
Exact Mass: 357.0576
Mol. Wt.: 358.2276

ER-817664 (1 wt) was dissolved in ACN (10 v), the suspension was cooled to 0° C. and 2-acetoxy-2-methylpropanyl bromide (4.0 eq, 2.4 v) was added followed by the addition of $H_2O$ (1.0 eq., 0.07 v). The resulting mixture was stirred at 0° C. for 2 hours. $NaHCO_3$ (sat. aqueous, 8.0 eq. 40 v) was added slowly at 0° C. The resulting mixture was stirred at room temperature for 30 minutes prior to extraction with MTBE (2×20 v). The organic layer was washed with brine (5 v) and concentrated to give the product as colorless oil.

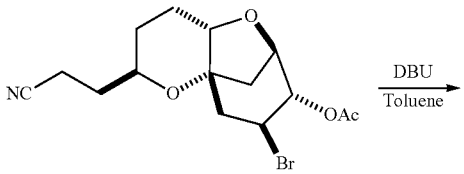

$C_{15}H_{20}BrNO_4$
Exact Mass: 357.0576
Mol. Wt.: 358.2276

-continued

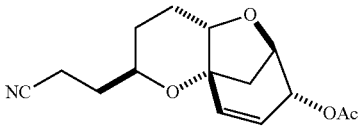

$C_{15}H_{19}NO_4$
Exact Mass: 277.1314
Mol. Wt.: 277.3157

The starting bromide (1 wt), depicted immediately above, was dissolved in toluene (10 v). DBU (1.8 eq., 0.73 v) was added and the mixture was heated at 80° C. The mixture was cooled to room temperature, diluted with MTBE (20 v), and washed with water (5 v) and then brine (5 v). The organic layer was then concentrated to give the product as an off-white powder.

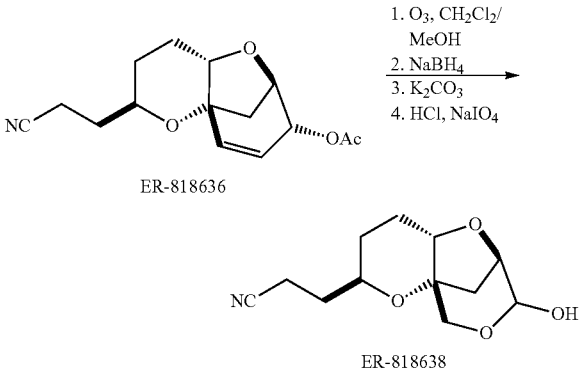

ER-818636

ER-818638

The starting olefin compound (1 wt), depicted immediately above, was dissolved in $CH_2Cl_2$ (5 v) and MeOH (5 v), and cooled to between −40° C. to −45° C. The solution was then treated with $O_3$. Excess $O_3$ was removed by $N_2$ purge and the solution was warmed to −15° C. $NaBH_4$ (1.0 eq, 0.18 wt) was added and the mixture was [warm] *warmed* to 0° C. $K_2CO_3$ (1.3 eq.) was added and the suspension stirred at rt. The reaction was neutralized with 1N HCl (~4 eq, ~20 v) at 0° C. and the solution was extracted with MTBE(10 v) to remove lypophilics. The aqueous layer was concentrated to remove $CH_2Cl_2$ and MeOH. THF (4 v) was added followed by $NaIO_4$ (2 eq, 2 wt). The reaction was extracted with MTBE (10 v) and n-BuOH (10 v). The combined organic extracts were concentrated and the resulting powder was triturated with EtOAc. After filtration the lactol was isolated as a pale yellow powder.

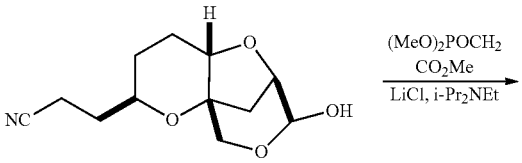

ER-818638

-continued

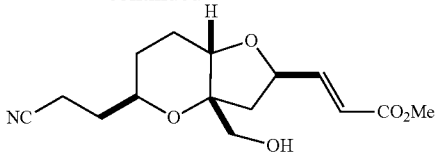

ER-818640

ER-818638 (1 wt) and LiCl (2.0 eq, 0.35 wt) was stirred in ACN (8.7 v). Hunig's base (1.5 eq) was added at 25° C. 1 N HCl (5 v) was added and the mixture was extracted with MTBE (10 v). The organics were concentrated to provide ER-818640 which was used as is in the next step.

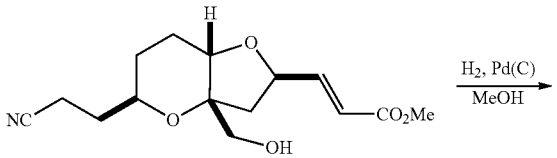

$C_{15}H_{21}NO_5$
Exact Mass: 295.142
Mol. Wt.: 295.3309

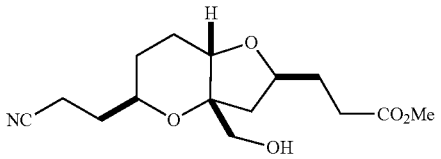

$C_{15}H_{23}NO_5$
Exact Mass: 297.1576
Mol. Wt.: 297.3468

The starting α-olefin ester compound (1 wt), depicted immediately above, was dissolved in MeOH (10 v) and added to 10 wt % of Pd(C) (0.09 eq, ~0.33 wt) under $N_2$. The suspension was then stirred under $H_2$. The suspension was filtered through a Celite® pad (20 wt), rinsing the filter cake with MeOH (20 v). The filtrate was concentrated and purified by flash chromatography to give product as colorless oil (94.3% yield).

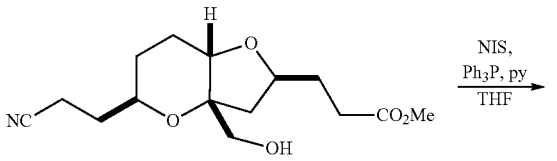

$C_{15}H_{23}NO_5$
Exact Mass: 297.1576
Mol. Wt.: 297.3468

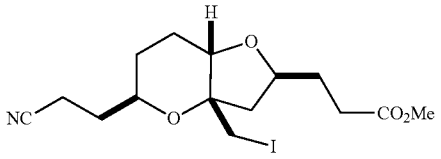

$C_{15}H_{22}INO_4$
Exact Mass: 407.0594
Mol. Wt.: 407.2439

Pyridine (10 eq.), $Ph_3P$ (7 eq.) and NIS (4 eq.) were added to the solution of the ester (1 wt) in THF (15 v) separately. The reaction mixture was stirred at ambient temperature. Aqueous citric acid (20 wt %, 10 eq) was added and the mixture diluted with TBME (30 v). The aqueous layer was separated and the organic layer washed with water (5 v), aqueous $Na_2S_2O_3$ (10% wt/v, (5 v), water (5 v) and brine (5 v). The organic layer was concentrated and purified by flash chromatography to give product as colorless oil.

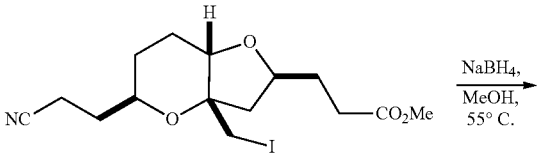

$C_{15}H_{22}INO_4$
Exact Mass: 407.0594
Mol. Wt.: 407.2439

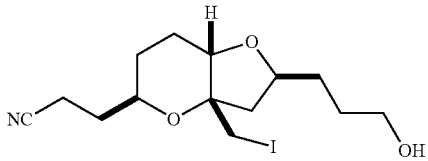

$C_{14}H_{22}INO_3$
Exact Mass: 379.0644
Mol. Wt.: 379.2339

The starting iodide (1 wt) was dissolved in MeOH (30 v) and heated to 55° C. $NaBH_4$ (47 eq.) was added in 6 portions at 55° C. over 80 minutes. The reaction was cooled to 0° C. and quenched with 1N HCl (30 v). After stirring 5 minutes, the mixture was diluted with brine (30 v) and extracted with DCM (50 v×2). The organic layer was dried over $Na_2SO_4$ and concentrated. The crude product was used directly in the next step.

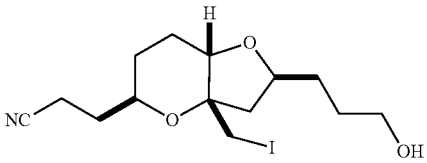

$C_{14}H_{22}INO_3$
Exact Mass: 379.0644
Mol. Wt.: 379.2339

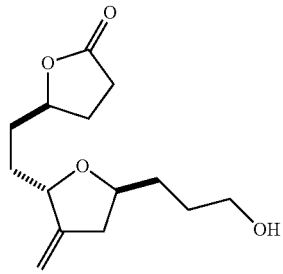

$C_{14}H_{22}O_4$
Exact Mass: 254.1518
Mol. Wt.: 254.3221

The starting alcohol (1 wt), depicted immediately above, was dissolved in EtOH (70 v) and Zn (165 eq.) was added.

The suspension was refluxed at 75-80° C. The reaction mixture was cooled to ambient temperature and 1N HCl (70 v) was added. The mixture was extracted with DCM (3×100 v), the organic layer washed with brine and concentrated.

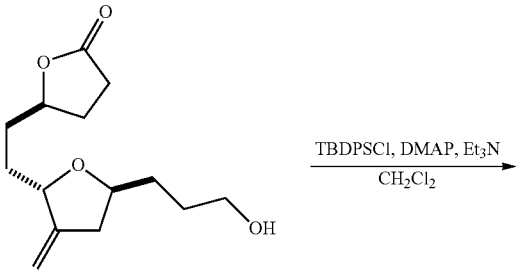

$C_{14}H_{22}O_4$
Exact Mass: 254.1518
Mol. Wt.: 254.3221

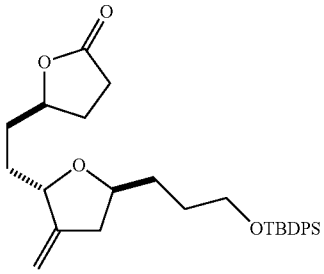

$C_{30}H_{40}O_4Si$
Exact Mass: 492.2696
Mol. Wt.: 492.7217

The starting lactone, as depicted immediately above, was dissolved in DCM (50 v), $Et_3N$ (5.0 eq.), DMAP (0.3 eq.) and TBDPSCl (1.5 eq.) were added separately at ambient temperature under $N_2$, and the resulting solution was stirred at ambient temperature for 2-3 hours. Upon the completion of the reaction, the mixture was diluted with TBME (100 v), washed with sat. aq. $NaHCO_3$ solution (10 v), $H_2O$ (10 v) and brine (10 v). The organic layer was concentrated and purified by flash chromatography to give the product as colorless oil.

Example 4c

Example 4c provides another alternate method of preparing compounds of formula F-2 using the general scheme set forth at Scheme VII above. This method uses ER-811510 as an intermediate as prepared according to Example 3, above where acetone is used instead of cyclohexanone.

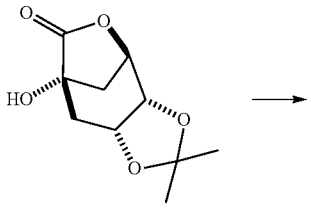

ER-811510

-continued

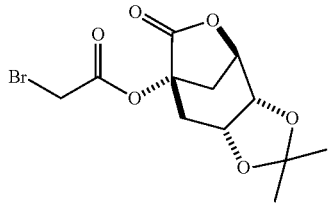

ER-812771

ER-811510 (1 wt, 1 eq) was dissolved in methylene chloride (6.3 v) and cooled to −5° C. Pyridine (0.41 vol, 1.1 eq) was added followed by bromoacetyl bromide (0.44 vol, 1.1 eq) while keeping the temperature below 0° C. The reaction was stirred at [1] *1* hour and warmed to room temperature. Water (8 vol) was added and the layers separated. The organic layer was washed sequentially with aqueous copper sulfate pentahydrate (1.0 M, 10 vol), water (8 vol), and brine (10 vol) then dried over magnesium sulfate, filtered and concentrated in vacuo to afford ER-812771 as a tan solid.

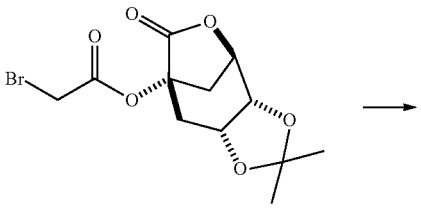

ER-812771

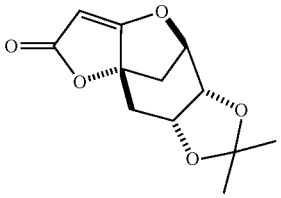

ER-812772

ER-812771 (1 wt, 1 eq) was dissolved in acetonitrile (6 v) and triphenylphosphine was added and the reaction heated at 50° C. for 45 minutes. The reaction was cooled to −10° C. then 1,8-diazabicyclo[5.4.0]undec-7-ene (DBU, 0.35 vol, 0.8 eq) was added. The reaction was stirred for 15 minutes, heated to 80° C. for 45 minutes then cooled to ambient temperature. Ammonium chloride (saturated aqueous, 10 vol) was added and the aqueous layer extracted with ethyl acetate (3×10 v). The combined organic layers were dried over magnesium sulfate and concentrated in vacuo. The crude product was purified by chromatography to afford ER-812772 as a white solid.

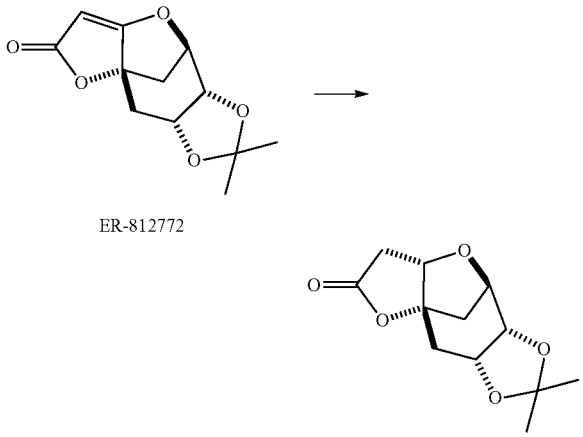

ER-812772

ER-812829

ER-812772 (1 wt, 1 eq) was dissolved in ethyl acetate (8 v). 10% Palladium on carbon (0.05 wt, 0.01 eq) was added, the reaction purged with nitrogen then stirred under hydrogen atmosphere for 2 hours. The catalyst was removed by filtration through Celite with ethyl acetate washed. The combined filtrates were concentrated in vacuo to afford ER-812829 as a white solid.

Example 5

Preparation of F-3a

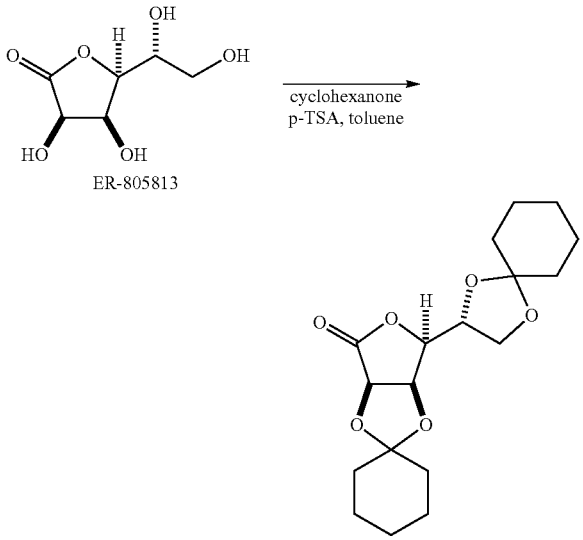

ER-805813

ER-805715

D-Gulonolactone (1 wt., 1 eq.), cyclohexanone (2 to 3 eq.), toluene (6 vol.), and p-toluenesulfonic acid (0.021 wt., 0.02 eq.) were charged to the reaction vessel. Reaction mixture was heated to reflux with stirring. Upon azeotropic removal of water the reaction was complete. The reaction mixture was cooled to 85 to 90° C. and agitation was increased. Heptane (5.2 vol.) was added over 20-30 minutes with stirring. Cooled to 65-70° C. and stirred for 30 minutes at 65-70° C. The solid product was filtered at 65-70° C., maintaining mother liquor temp [35° C] *>35° C*. Re-filtered at 35-40° C. and maintained the mother liquor at ambient temperature for 30 minutes. Re-filtered the mother liquor. The filter cake was washed two times with heptane (2×1.7 vol.) then dried to afford ER-805715. Yield 84% (1.6 wt.).

In an alternate method for preparing ER-805715, D-gulonolactone (1 wt), cyclohexanone (1.32 wt, 2.4 eq), p-TsOH-monohydrate (0.02 wt, 0.02 eq) and toluene (12 vol) were refluxed together for 19 hours, while azeotropically removing water. The mixture was washed with 5% aqueous $NaHCO_3$ (4 vol) followed by saturated aqueous NaCl (2 vol×2, pH=7). The organic phase was concentrated by distillation (ca. 4.5 vol of toluene remaining) and cooled to 100° C. before heptane (10 vol) was added, maintaining internal temperature [80° C] *>80° C*. The mixture was heated to reflux for at least 1 hour before it was cooled to and aged at 85° C. for 3 hours, at 80° C. for 3 hrs and then cooled to 40° C. in 12 hrs. The product was collected by filtration and the cake washed with heptane (2 vol). The filter cake was dried by airflow to afford ER-805715 (1.48 wt) in 78% of yield.

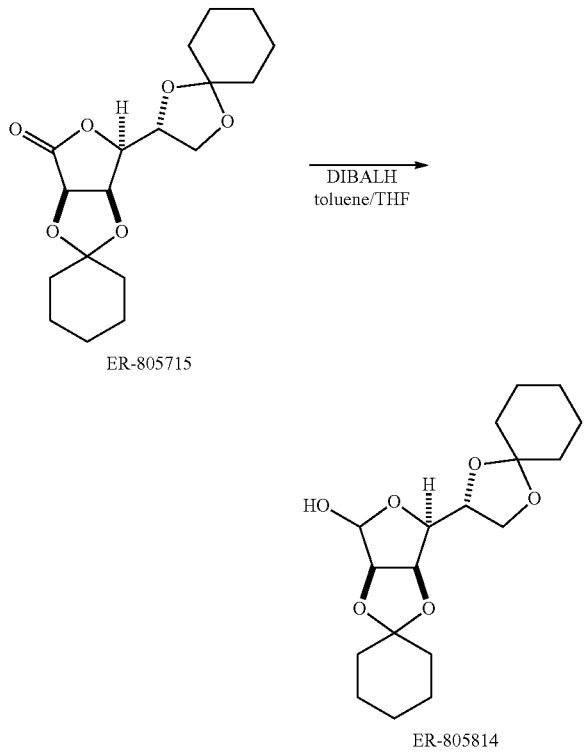

ER-805715

ER-805814

ER-805715 (1 wt., 1 eq.) was charged to reaction vessel and dissolved in anhydrous THF (3.34 vol.) and anhydrous toluene (2.5 vol.). The mixture was cooled to −15 to −10° C. DIBALH (1.5M in toluene, 2.4 vol., 1.2 eq.) was added over 1 hour and the mixture stirred for 15-30 minutes at −15 to −10° C. The reaction was inverse quenched into KNa-Tartrate solution (1 wt. KNa Tartrate in 2.9 wt. water) at 10° C. and the resulting mixture allowed to warm to room temperature and stir for 4 hours. The mixture was filtered then the layers separated and extracted with MTBE (2 vol.). The organic layers were combined and the solvents removed in vacuo to afford ER-805814. Yield 100%, (1.02 wt.).

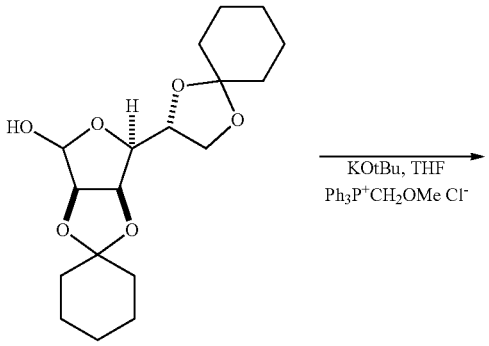

ER-805814

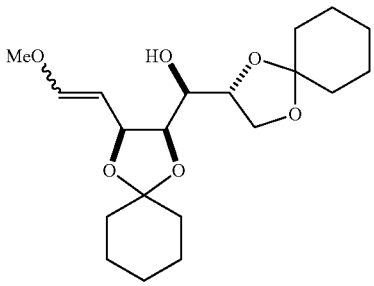

ER-805815

ER 805814 (1 wt.) was dissolved in anhydrous THF (3.3 vol.) and treated with (methoxymethyl)triphenylphosphonium chloride (2.11 wt., 2.1 eq.). The reaction mixture was heated to 28-32° C. then a solution of KOtBu (0.66 wt., 2 eq.) in anhydrous THF (2.64 vol.) was added over 100-140 minutes, maintaining reaction temperature 30-35° C. After 5 hours, the reaction was cooled to 20-25° C., MTBE (5.11 vol.) was added and the mixture stirred. Brine (3 wt.) and water (3 wt.) were added (exothermic at start of addition, controlled by bath @20-25° C.). Organic layer was separated and treated with a solution of maleic anhydride (0.27 wt.) in MTBE/THF (1/1 v/v, 1.78 vol.). NaOH solution (0.088 wt. in 2.5 vol. water) was added slowly to the reaction mixture. The organic layer was concentrated to give crude ER 805815 (0.985 wt.). The residue was triturated three times with MTBE/heptane (1/4 v/v, 6.6 vol.). The extract was filtered through $SiO_2$ (3 wt), eluting with MTBE/heptane (1/2 v/v, 45 vol.). The filtrate was concentrated to give ER-805815 (0.88 wt., 81% yield).

In an alternate method for preparing ER-805815, a solution of t-BuOK (0.989 wt, 3 eq) in THF (4 wt) was added to a suspension of (methoxymethyl)triphenylphosphonium chloride (3.12 wt, 3.1 eq) in THF (1.78 wt), maintaining the reaction temperature between 0-10° C. The addition vessel was rinsed with THF (2×0.7 wt). A solution of ER-805814 (1 wt, 1 eq) in THF (1.42 wt) was added to the reaction, maintaining 0-10° C. The addition vessel was rinsed with THF (2×0.7 wt). The mixture was stirred at 20-30° C. overnight and 30-35° C. for 3 hours. The reaction was cooled below 30° C. and diluted with MTBE (3.7 wt) followed by 10 wt % aqueous NaCl (4 wt) solution. The mixture was stirred for 30 minutes and the layers were separated. Maleic anhydride (0.63 wt, 2.2 eq) was added and the mixture stirred at room temperature for 30 minutes. Water (6 wt) and a solution of NaOH (48 wt %, 0.64 wt, 2.6 eq) was added dropwise, maintaining the reaction below 15° C. After stirring below 15° C., the lower layer was separated. Water (6 wt) was added followed by a solution of NaOH (48 wt %, 0.64 wt, 2.6 eq), keeping the mixture below 15° C. during the addition. After stirring below 15° C., the lower layer was separated. The organic layer was washed three times with a 15 wt % aqueous NaCl solution (3×4 wt). The organic layer was concentrated in vacuo. The residue was diluted with MTBE (1 wt) and concentrated in vacuo. The residue was diluted dropwise with IPE (3 wt) at 40-50° C. over 30 minutes. The suspension was stirred for 1 hour at 40-50° C. and slowly cooled to 0-10° C. and stirred for 1 hour. The solids were filtered and the cake washed with IPE (2 wt). The filtrate and washings were concentrated in vacuo. The residue was treated with MeOH (2.37 wt) and water (0.4 wt) and extracted with heptane (2.74 wt). The lower layer was extracted 9 times with heptane (2.05 wt). The extracted solutions were combined and concentrated in vacuo to give ER-805815 (1.07 wt, 98.6%).

In an alternative method for workup of ER-805815, the crude organic layer that is produced following brine wash and concentration is treated with MTBE (2.86 wt) and celite (0.5 wt). After stirring for 2.5 h, heptane (1.46 wt) was added over 2 hrs and the mixture stirred overnight. The precipitate was filtered. The filter cake was washed with MTBE/Heptane (1:1) (5 wt). The filtrate was concentrated in vacuo until the volume was decreased to about 3 volume. The residue was dissolved in MeOH (2 wts) and $H_2O$ (6 wts). The mixture was extracted with heptane/MTBE (5:1) (3*6 wts). The organic layer was separated and concentrated to provide ER-805815 which was used as is for the following step.

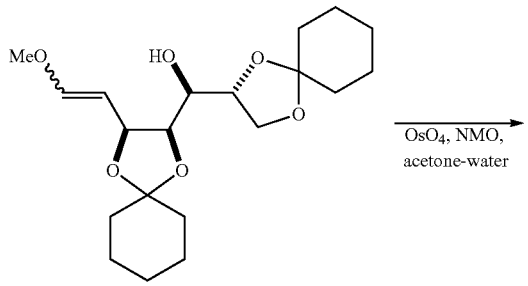

ER-805815

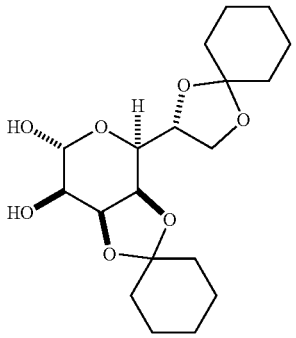

ER-805816

ER-805815 (1 wt) was dissolved in acetone (2.4 vol) and water (0.4 vol). N-Methylmorpholine N-oxide (0.62 wt, 2 eq) was added and the mixture cooled to 0-5° C. $OSO_4$ (0.15M in water, 0.065 vol) was added and the reaction was maintained at 0-5° C. The reaction mixture was stirred at 0-5° C. for 12 hours. Water (0.2 vol) was added over 1 hour at 0-2° C. The mixture was stirred for one hour at 0-5° C. The product was filtered and the solids washed twice with pre-cooled (0-5° C.) acetone/water (1/1, v/v, 2×0.7 vol). The product was dried to afford ER-805816 (0.526 wt, 52% yield, residual Os <17 ppm).

In an alternate method for preparing ER-805816, a solution of ER-805815 (1 wt, 1 eq) in acetone (4 wt) was charged into a four-necked flask, then water (0.5 wt) was added at ambient temperature. To the mixture was added anhydrous N-methylmorpholine-N-oxide (0.38 wt, 1.2 eq). Potassium osmate dihydrate (0.003 wt, 0.003 eq) was added portion-wise at 25 to 35° C. while cooling with water. The mixture was kept at this temperature for 4 hours. A solution of sodium thio sulfate 0.075 wt, 0.49 eq) in water (0.5 wt) was added at ambient temperature, then the mixture was stirred for 0.5 hour. The mixture was cooled to 0-5° C. and stirred for 2 hours. The resulting precipitate was collected and the wet cake was washed with methanol (0.6 wt) and water (1.5 wt) to obtain the crude product (1.25 wt). The crude product sample was dried (0.611 wt). The crude ER-805816 (1.25 wt) was added to water (3.05 wt) and stirred for 2 hours at about 25° C. The precipitate was filtered and washed with water (1.53 wt) to afford the crude wet cake (1.05 wt). The crude product sample was dried and sampled, ICP Os=37 ppm. The crude ER-805816 (1.05 wt) was added to water (2.81 wt) and stirred for 2 hours at about 25° C. The precipitate was filtered and washed with water (1.4 wt) and methanol (0.45 wt) to afford the crude ER-805816 (0.736 wt). The wet cake was dried crude product (0.56 wt, ICP (Os)=28 ppm). ER-805816 (0.56 wt) was dissolved in acetone (1.76 wt) at 45 to 55° C. To the solution was added active carbon (0.027 wt) and stirred at same temperature for 0.5 hour. The mixture was filtered and the cake was washed with hot acetone (0.214 wt). The filtrate was kept at 45 to 50° C. and water (0.83 wt) was added over 10 minutes and temperature was kept at 40 to 50° C. during water addition. The mixture was cooled to 0 to 5° C. and stirred for 1.5 hours. The white precipitate was filtered and washed with a solution of acetone (0.17 wt) and water (0.22 wt) then dried to give ER-805816 (0.508 wt, 0.49 eq, KF 5.0%, ICP (Os) 9.6 ppm).

ER-805816 (1 wt) was slurried in acetic acid (0.89 vol, 5.8 eq) and acetic anhydride (3.57 wt, 13 eq). Anhydrous $ZnCl_2$ (0.2 wt, 0.54 eq) was added. Reaction mixture was stirred for 24 hours 18-22° C. Reaction was quenched into ice (5 wt) and water (5 vol). EtOAc (10 vol) was added with stirring and the aqueous layer is separated. The aqueous layer was back extracted with EtOAc (10 vol). The combined organic layers were washed sequentially with brine (10 vol), 5% aqueous NaOAc (6 vol), and brine (6 vol). The organic layer was concentrated. The crude concentrate was dissolved in 25% EtOAc/hex (4 vol) and filtered through $SiO_2$. The pad was washed with 25% EtOAc/hex (2×12 vol) and further 25% EtOAc/hex (48 vol). The organic layer was concentrated to give ER-805819 (1 wt, 81%).

In an alternate method for preparing ER-805819, zinc chloride (0.2 wt, 0.54 eq), acetic anhydride (2.75 wt, 10 eq), and acetic acid (1 wt, 6 eq) were combined. The mixture was cooled to 15-20° C. ER-805816 (1 wt, 1 eq) was added, maintaining the internal temperature at 15 to 30° C. The mixture was then stirred at 35-40° C. for 6 hours. The reaction mixture was cooled below 25° C. Methanol (3.2 wt, 4 vol) was added drop-wise maintaining reaction temperature below 25° C. Heptane (2.7 wt, 4 vol) was added. Water was added (4 wt, 4 vol) maintaining reaction temperature below 25° C. The mixture was stirred for 15 minutes, and then the phases were separated. The lower layer was washed twice with heptane (2.7 wt, 4 vol) and the heptane layers were discarded. The lower layer was extracted twice with toluene (6.1 wt, 8 vol). The combined toluene layers were washed twice with 17 wt % potassium bicarbonate aqueous solution (0.82 wt KHCO3 in 3.98 wt water, 4.36 vol), twice with water (4 wt), and concentrated. Methanol (3.95 wt, 5 vol) was added at 25-30° C. and the mixture stirred for 10 minutes. Water (0.3 wt) was added at 25-30° C. The mixture was cooled to 0° C. and seeded. The mixture was stirred at 0° C. for 1 hour. Water (0.7 wt) was added drop-wise over 1 hour. Water (4 wt) was added drop-wise over 1 hour. The resulting precipitated solids were filtered, and the filter cake washed twice with a 0° C. methanol (1.03 wt) and water (0.7 wt) solution. The cake was dried to afford ER-805819 (0.99 wt, 0.84 eq).

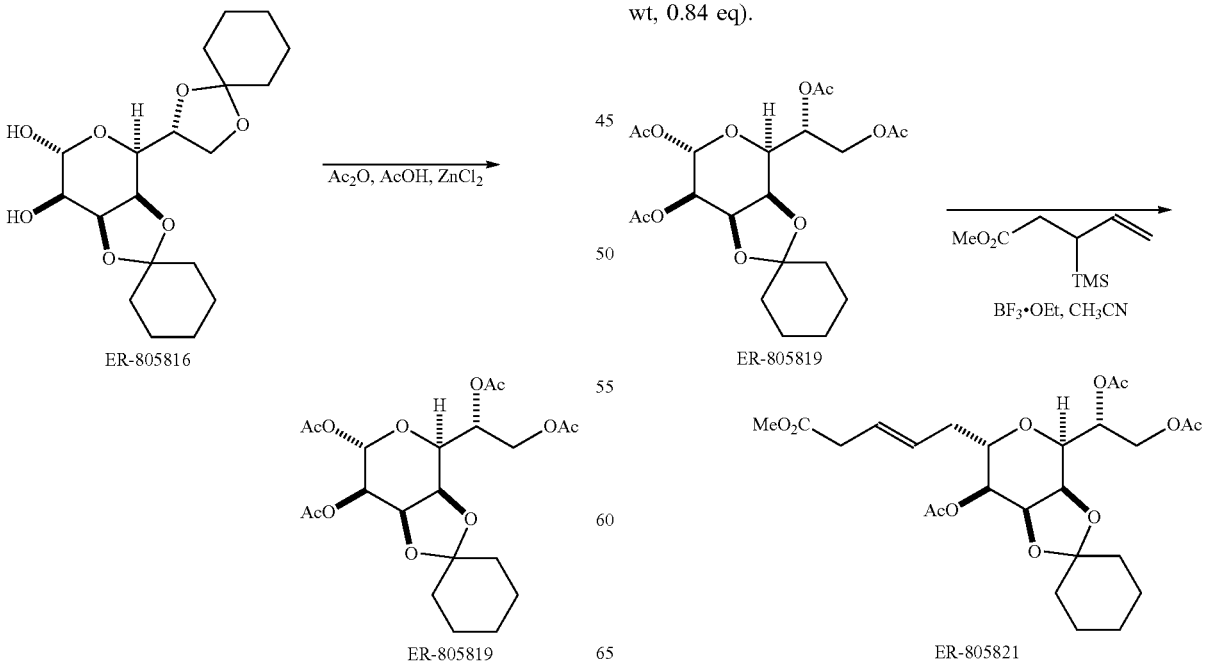

ER-805819 (1 wt) was dissolved in anhydrous acetonitrile (15 vol) and treated with methyl 3-trimethylsilylpent-4-eneoate (0.93 vol, 2 eq). The reaction mixture was cooled to 0-5° C. and $BF_3 \cdot OEt_2$ (0.54 vol, 1.95 eq) was added over 5 minutes, maintaining reaction temperature between 0-5° C. Reaction mixture was stirred 0-5° C. for 12 hours. Reaction was quenched into saturated sodium bicarbonate (20 vol) with vigorous stirring. Extracted twice with EtOAc (2×8 vol). The combined organics were washed with brine (12 vol) and concentrated to give ER-805821 (1 wt, 88% yield, use as is).

In an alternate method for preparing ER-805821, ER 805819 (1 wt, 1 eq) and [ER] methyl 3-trimethysilylpent-4-eneoate (0.93 vol, 2 eq) were dissolved in anhydrous acetonitrile (5.46 wt, 7 vol). The reaction mixture was cooled to 0-5° C. and $BF_3$[·] -$OEt_2$ (0.54 vol, 1.95 eq) was added over 5 minutes, while maintaining reaction temperature between 0-5° C. The reaction mixture was stirred at 0-5° C. for 20 hours then heptane (5.47 wt, 8 vol) was added at 0-5° C. The phases were separated and the lower layer treated with heptane (5.47 wt, 8 vol) at 0-5° C. The reaction was quenched by dropwise addition of 7.4% potassium bicarbonate aqueous solution (0.64 wt $KHCO_3$ and 8 wt water), while maintaining the reaction temperature at 0-15° C. Toluene (8.65 wt, 10 vol) was added and the mixture stirred for 30 minutes. The lower layer was separated and the upper organic layer washed twice with water (10 vol) and concentrated to afford ER-805821 as a crude oil (1.05 wt, 0.935 eq).

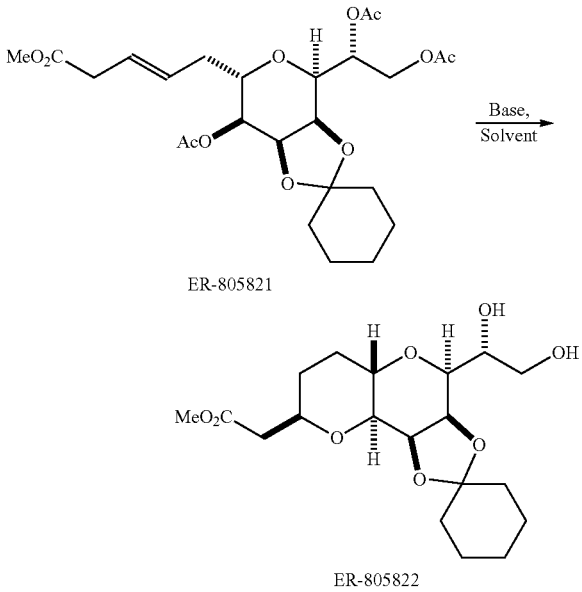

ER-805821 (1 wt) was dissolved in anhydrous THF (8.4 vol) and anhydrous MeOAc (2 vol). Triton B(OH) (3.6 vol) was added over 2 minutes, reaction maintained 17-23° C. Reaction was stirred for 1.5 hour. Reaction mixture was filtered. The filtrate was concentrated and passed through a pad of $SiO_2$ (5 wt, EtOAc, 20 vol). The filtrate was washed with brine (2.2 vol) and evaporated to give ER-805822 (0.54 wt, 72% yield).

In an alternate method for preparing ER-805822, ER-805821 (1 wt, 1 eq, 11.18 g, 21.81 mmol) was dissolved in anhydrous MTBE (4.4 wt, 6 vol.) and cooled to 0-5° C. NaOMe (28 wt % in MeOH, 0.564 wt, 1.5 eq) was added to the mixture over 1 hour at 0-5° C. and stirred for 3 hour at same temperature range. The reaction was quenched by addition of acetic acid (0.188 wt, 1.6 eq.), maintaining 0-5° C. during addition. The mixture was stirred overnight then treated with a 5 wt % aqueous solution of $KHCO_3$ (3 wt) and ethyl acetate (3.6 wt, 4 vol) at 0-5° C., and then stirred for 15 minutes. After phase separation, the lower layer was extracted with ethyl acetate (3.6 wt, 4 vol) twice. The combined organic layer was concentrated. To the residue was added acetone (2 wt, 2.5 vol) and IPE (2 wt, 2.7 vol) and stirred overnight at 0-5° C. The mixture was filtered through Celite® (0.25 wt) and washed with acetone (2 wt). The filtrate was concentrated to afford the crude oil (0.55 wt). To the residue was added acetone (0.2 wt, 0.25 vol.) and IPE (0.54 wt, 0.75 vol.) and stirred for 1 hour at 40-50° C. The solution was seeded with ER-805822 at room temperature and stirred overnight at room temperature. To the suspension was added IPE (1.27 wt, 1.75 vol.) over 2 hours at room temperature. After stirring for 5 hours at room temperature, the precipitate was collected by filtration, and the cake washed with acetone/IPE (1/10) (2 vol.). The obtained cake was dried in a tray-type chamber at 30-40° C. overnight to afford the desired product ER-805822 (0.286 wt, 0.38 eq) in 38.0% yield from ER-805819.

In an alternative method for workup of crude ER-805822, the residue following concentration of the final EtOAc solution was dissolved in IPA (2 wt) and the solution was heated to 50° C. Heptane (5 wts) was added and the mixture was cooled to 20° C. and seeded. The mixture was stirred at 20° C. overnight. Heptane (10 wts) was added and the mixture was cooled to −5° C. in 30 min and stirred at −5° C. for 5 hrs. The mixture was filtered and the filter cake was washed with heptane (2 wts). The filter cake was dried with air flow under vacuum to provide ER-805822 (60%).

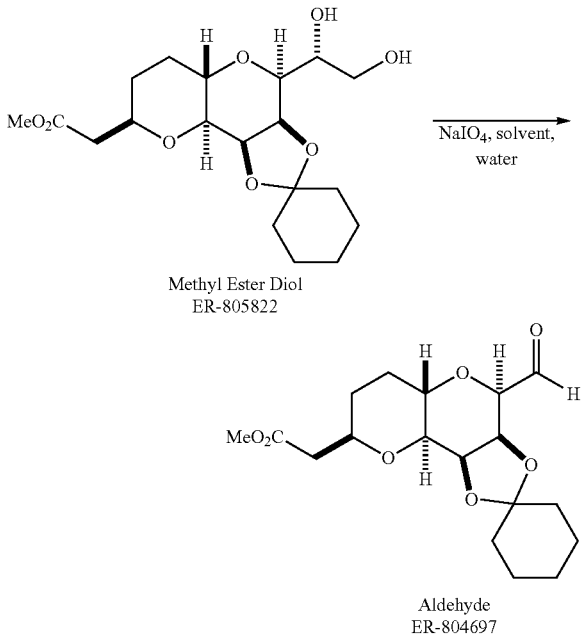

ER 805822 (1 wt) was dissolved in ethyl acetate or another appropriate solvent (5 vol) and water (5 vol). $NaIO_4$ (0.58 wt, 1.05 eq) is added portionwise over 30 min to 1 hour, maintaining reaction temperature 0-10° C. Reaction is stirred for up to 2 hours. The reaction mixture was treated with NaCl (1 wt) and stirred for 30 min at 0 to 10° C. The reaction mixture was filtered and the cake is rinsed with ethyl acetate (2 vol). The phases were separated and the lower layer extracted with EtOAc (5 vol) three times. The combined organic layer was washed with 20% aqueous NaCl (5 wt). The organic layer was concentrated to give ER 804697 (1 wt). The residue was dissolved in toluene (2 vol) and the solution concentrated. The residue was dissolved in acetonitrile (7 vol) and used for the next step.

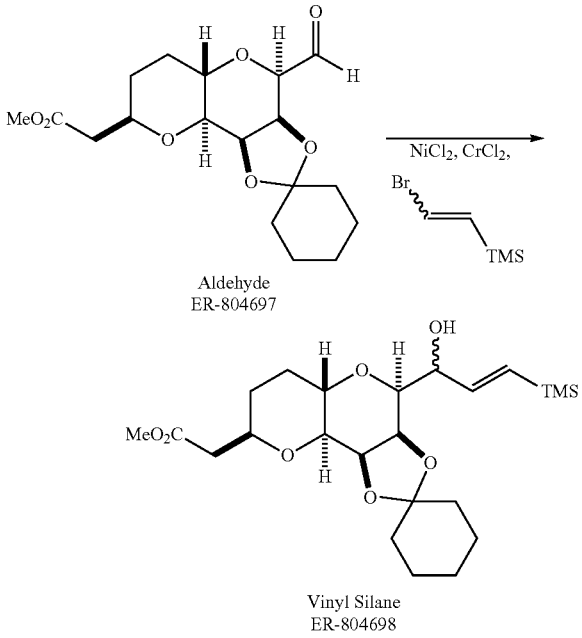

$NiCl_2$ (0.025 wt) and $CrCl_2$ (2.5 wt) were charged to reaction vessel under inert atmosphere. Anhydrous dichloromethane (5 vol) was charged. Stirring was initiated and the mixture was cooled to 0-3° C. Anhydrous DMSO (6.7 vol) was added with vigorous stirring over 45 minutes, maintaining temperature below 20° C. ER-804697 (1 wt) was dissolved in anhydrous dichloromethane (1 vol) and charged to the reaction vessel. The resulting mixture was warmed to 25° C. and 1-bromo-2-trimethylsilylethylene (2.58 wt) was added neat over 20 minutes. The reaction temperature was maintained below 45° C. The reaction was stirred for 30 minutes at 25-35° C. following complete addition. Methanol (5 vol) was added and the mixture was stirred for 10 minutes. MTBE (33 vol) was charged and the slurry transferred into 1N HCl (25 vol) and water (10 vol). The mixture was stirred for 5 minutes. The aqueous layer was back extracted with MTBE (10 vol) and the combined organics washed sequentially with 0.2N HCl (17 vol), twice with 1% NaCl solution (2×17 vol), and brine (13 vol). The organic layer was concentrated and purified ($SiO_2$, 25 wt, 10 column vol EtOAc/Hex 1/3.5 v/v) to give ER-804698 (0.53 wt, 61%).

In an alternate method, this reaction was performed in the presence of the chiral ligand ER-807363 in a manner substantially similar to that described for the preparation of ER-118047, infra.

In an alternate method for preparing ER-804698, DMSO (7 vol.) and MeCN (7 vol) were degassed and cooled to 0-10° C. The solution was treated portionwise with $CrCl_2$ (10 eq, 3.47 wt) and $NiCl_2$ (0.1 eq, 0.037 wt) such that the internal temperature did not exceed 20° C. A solution of ER-804697 (1 wt, 1 eq) in MeCN (7 vol) and 1-bromo-2-trimethylsilylethylene (5 eq, 2.5 wt) were added dropwise at 0-10° C., not allowing the internal temperature to exceed 15° C. The reaction mixture was stirred at 5-15° C. overnight. To the mixture was added methanol (5.5 wt), water (7 wts), and MTBE (5.2 wts). The reaction was stirred for 1 hour and the lower layer was separated (layer 1). To the upper layer was added a premixed solution of NaCl (1.5 wts) and water (13.5 wts). The mixture was stirred for 1 hour and the lower layer was separated (layer 2). To the upper layer was added heptane (4.8 wts), methanol (2.8 wts), and a premixed solution of NaCl (1.5 wts) and water (13.5 wts). The mixture was stirred for 1 hour and the lower layer was separated (layer 3). The upper layer was drained and saved (organic 1). The reactor was charged with layer 1, methanol (2.8 wts), and MTBE (2.8 wts). The mixture was stirred overnight. The lower layer was separated and discarded. The upper layer was treated with layer 2. The mixture was stirred for 1 hour and the lower layer was separated and discarded. The upper layer was treated with layer 3 and heptane (4.8 wts). The mixture was stirred for 1 hour and the lower layer was separated and discarded. The upper layer was drained and saved (organic 2). The reactor was charged with layer 3, MTBE (0.8 wts), and heptane (2.7 wts). The mixture was stirred for 1 hour and the lower layers was separated and discarded. The upper layer was combined with organic 1 and organic 2. The combined organics were filtered and concentrated at reduced pressure to afford the crude ER-804698 which was purified by chromatography ($SiO_2$, 25 wt, 10 column vol EtOAc/Hex 1/3.5 v/v) to give ER-804698 (0.67 wt, 57% yield).

In an alternate method of preparation of ER-804698, the crude material is taken directly to the next step without purification.

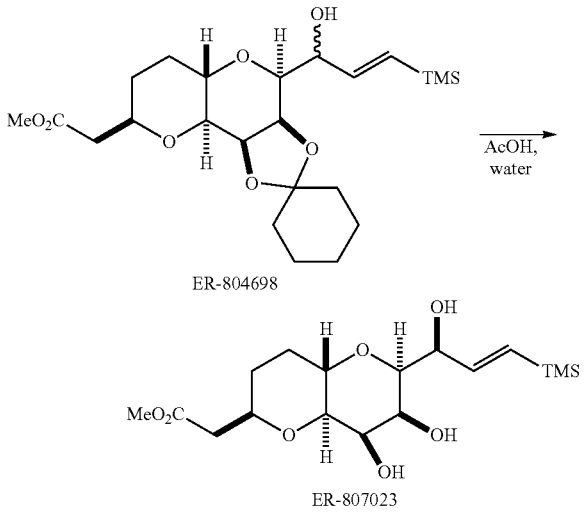

ER 804698 (1 wt, 1 eq) was treated with AcOH (4.2 wts) and water (4.2 wts). The mixture was heated to 90-97° C. for 100 min. The mixture was cooled to below 15° C. then washed with heptane (2×2.7 wts) twice below 15° C. After phase separation, a mixture of 20 wt % aqueous $KHCO_3$ solution (7.7 wts, 35 eq) and MTBE (5.95 wts) was added dropwise to the lower layer such that temperature does not exceed 15° C. After phase separation the upper layer was washed successively with 5 wt % aqueous $KHCO_3$ solution (0.2 wts), and twice with 5 wt % aqueous NaCl solution (2×0.2 wts). The organic layer was concentrated under reduced pressure and MTBE (1.49 wts) was added. The mixture was heated to 55° C. and stirred until dissolved. Heptane (1.00 wts) was added to the solution and the solution was cooled to 40-45° C. Additional heptane (4.47 wts) was added to the solution and the solution was cooled to 5-15° C. and then stirred overnight. The crystals were filtered and rinsed with heptane to provide ER-807023 (0.58 wts, 71% yield).

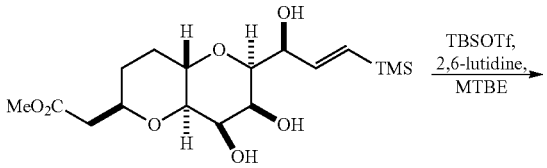

ER-807023

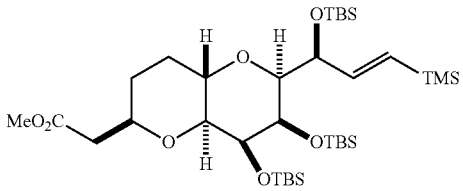

ER-804699

ER-807023 (1 wt, 1 eq) and MTBE (7.43 wts) were charged to a reactor under a nitrogen atmosphere. To the reaction was added 2,6-lutidine (2.15 wts, 7.5 eq). To the mixture was added dropwise TBSOTf (2.47 wts, 3.5 eq) at 0° C. The reaction mixture was stirred for 30 min at 0-10° C., then warmed to 23° C. over 1 hr and held at 23° C. for 16 hrs. MeOH (0.21 wts, 2.5 eq.) and water (14.8 wts) were added dropwise sequentially to the reaction mixture, maintaining temperature below 30° C. After phase separation, the upper layer was washed with 1N aqueous hydrochloric acid (16.2 wts), 5% NaCl aq. (14.8 wts), 5% $NaHCO_3$ aq. (14.8 wts), 5% NaCl aq. (14.8 wts), and 5% NaCl aq. (14.8 wts), respectively. The upper organic layer was concentrated by distillation under reduced pressure to afford the crude ER-804699. MeOH (7.91 wts) was added and the mixture was heated to 50° C. for 30 min. The mixture was cooled to 0° C. over 5 h, and then stirred overnight at 0° C. The solid was filtered, and the cake was washed with cold MeOH (4 wts) and dried to yield ER 804699 (1.42 wts, 74% yield).

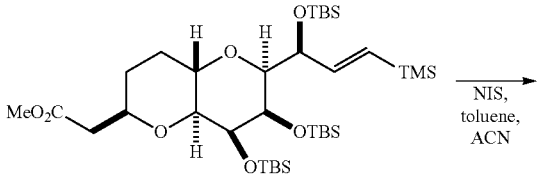

ER-804699

-continued

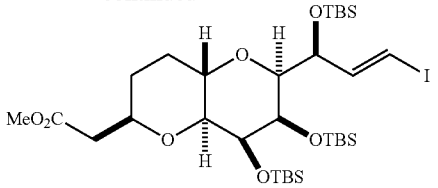

ER-803895

Into a reactor under a nitrogen atmosphere was charged a solution of ER-804699 (1 wt, 1 eq) in toluene (2.60 wts). Acetonitrile (4.72 wts) was added. TBSCl (0.011 wts, 0.05 eq) was added. The reaction mixture was warmed to 30° C. and the NIS was added (1.25 wts, 4 eq). The reaction mixture was stirred at 22 hrs at 30° C. The reaction was cooled to 25° C. and the mixture of aqueous sodium thiosulfate and sodium bicarbonate (10.35 wts) were added over 10 minutes keeping the internal temperature below 30° C. The reaction was stirred for 30 minutes at 25° C. The aqueous layer was separated. The upper layer was washed twice with 10% NaCl (aq) (2×9.9 wts). The organic layer was concentrated under reduced pressure to give crude ER-803895 that was purified using silica gel chromatography to provide ER-803895 (0.96 wt, 89.5% yield).

Example 6

Assembly of F-1a, F-2a, and F-3a and Preparation of B-1939

A. Preparation of (R) or (S) N-[2-(4-Isopropyl-4,5-dihydro-oxazol-2-yl)-6-methyl-phenyl]-methanesulfonamide

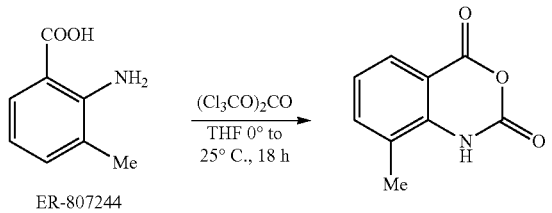

ER-807244 ER-807245

A pre-dried glass lined reactor was charged with triphosgene (1 wt., 1 eq.) and anhydrous THF (2 vol.) and was cooled to an internal temperature of −10° C. A second pre-dried glass lined *reactor* was charged with ER-807244 (1.27 wt., 2.5 eq.) and anhydrous THF (3 vol.) then cooled to an internal temperature of −10° C. The contents of the first reactor were transferred into the second reactor at a rate such that internal temperature did not exceed 15° C. After complete addition, the reaction was stirred at an internal temperature of 0° C. for 1 hour and then gradually warmed to 25° C. A sparge of nitrogen was used for 18 hours to scrub away excess phosgene with trapping of the off-gases through a 2 N NaOH solution. MTBE (3 vol.) was added and the solvent removed by distillation under $N_2$ purge at 40° to 46° C., adding more MTBE as needed. Upon complete removal of the phosgene, the mixture was cooled to an internal temperature of 5° to 10° C. and the solution filtered with MTBE (3 vol.) washes to yield ER-807245 (1.12 wt., 0.97 eq.) as a white crystalline solid.

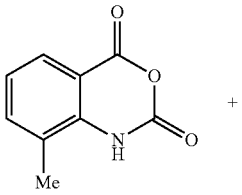

ER-807245

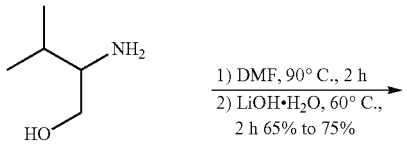

D-valinol or L-valinol

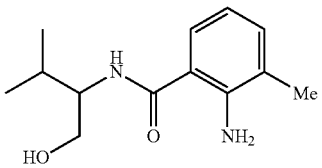

ER-806628 (D-valinol)
ER-808056 (L-valinol)

Into a pre-dried and inerted reactor 1, was added ER-807245 (1 wt., 1 eq.) and anhydrous DMF (4 vol.). With stirring, the mixture was heated to an internal temperature of 95° C. D or L-Valinol (1.05 eq., 0.61 wt.) was dissolved in anhydrous (DMF 1.3 vol.) in reactor 2 with heating to an internal temperature of 90° C. The contents of reactor 2 were transferred into reactor 1 at internal temperature 90° C. $CO_2$ evolution was [be] observed and the reaction was vented with a $N_2$ bleed. The reaction solution was stirred at 90° C. for 3 hours and then cooled to an internal temperature of 65° C. Then, an aqueous slurry of lithium hydroxide (0.47 wt., 2 eq.) in water (2 vol.) was added to reactor 1 and the suspension stirred at an internal temperature of 65° C. for 1 hour. The reactor was charged with water (5 vol.) cooled to an internal temperature of ~5° C. over 3 hours. The mixture was stirred for 8 hours at internal temperature ~5° C. and the desired product collected by filtration with water (2×4 vol.) washes followed by n-heptane (2×3 vol.). The product was dried under vacuum and $N_2$ flow at 35° C. for 24 hours or until KF≤250 ppm to yield ER-806628 or ER-808056 (0.80 wt., 0.60 eq.) as a crystalline solid.

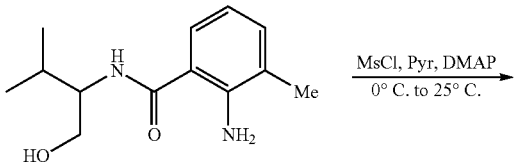

ER-806628 (R)
ER-808056 (S)

-continued

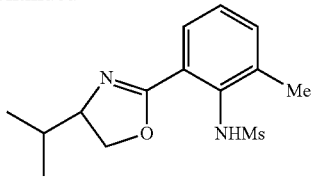

ER-806629 (R)
ER-807363 (S)

A pre-dried and inerted reactor under nitrogen was charged with ER-806628 or ER-808056 (1 wt., 1 eq.), pyridine (3 wt., 11.4 eq.) and DMAP (0.03 wt., 0.05 eq.). The reaction was cooled to an internal temperature of −10° C. then methanesulfonyl chloride (1.46 wt., 3 eq.) was added at a rate such that internal temperature was below 15° C. Upon complete addition, the reaction was stirred at an internal temperature of 0-15° C. for 1 hour and then slowly warmed to 25° C. over 2 hours. MTBE (2.6 vol.), was added followed by process water (2 vol.) at a rate such that the internal temperature did not exceed 35° C. The biphasic mixture was titrated with 6N hydrochloric acid, (~1.9 vol.) portion-wise until the pH of the aqueous layer=~3 to 5. If pH went under 3, 30% (w/w) aqueous solution of $Na_2CO_3$ was added to back titrate to the desired pH. The phases were allowed to partition and the aqueous phase separated. All organics were combined with water (0.7 vol.) and the aqueous phase discarded. The MTBE was distilled to a level of ~2 vol. at atmosphere pressure to constant bp 55° C. and KF <500 ppm. Additional MTBE was added if necessary. The solution was cooled to an internal temperature of 5-10° C. with seeding when necessary to induce crystallization. n-Heptane (0.5 vol.) was added and the mixture stirred for 18 hours at 5° C. ER-806629 or ER-807363 was collected by filtration with n-heptane (2×3 vol.) washes. A second crop of crystals was obtained by concentration of the filtrates to ½ volume and cooling to 0° C. The filter cake was dried under $N_2$ for 18 hours. The crude weighted ER-806629 was charged into a pre-dried reactor and MTBE (3 vol.) was added. The resulting mixture was heated to an internal temperature of 45-50° C. for 45 minutes and then slowly cooled to 5° C. over 3 hours, with seeding when necessary. n-Heptane (0.5 vol.) was added and the mixture stirred for 18 hours at an internal temperature of 5° C. The solid product was collected via filtration and n-heptane (2×3 vol.) washes then dried under vacuum at 35° C. for 24 hours to yield ER-806629 or ER-807363 (1.7 wt., 0.57 eq.) as a crystalline solid.

B. Assembly of F-1a and F-2a Intramolecular Ether Formation

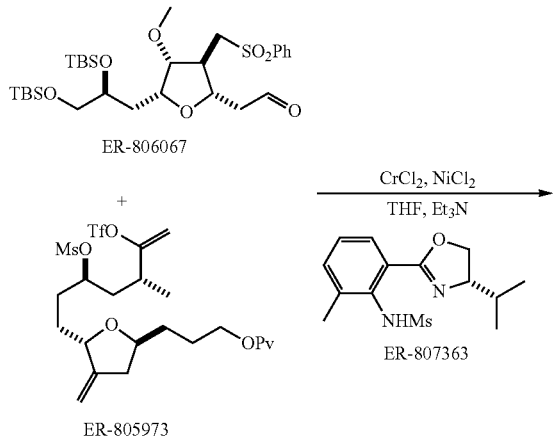

ER-806067

ER-805973

ER-807363

-continued

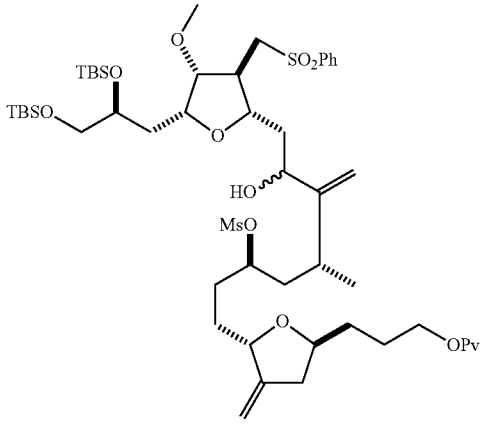

ER-808227

An appropriately sized reactor 1 was charged with ER-807363 (1.82 wt, 3.55 eq) and the atmosphere was exchanged for nitrogen. Anhydrous THF (15 vol) was added. In reactor 2, ER-806067 (F-1a, 1.14 wt, 1.1 eq) and ER-805973 (F-2a, 1 wt, 1 eq) were combined and dissolved in anhydrous THF (6.3 vol). With stirring, both reactors were sparged with nitrogen for 30-45 minutes. Under an inert atmosphere, reactor 2 was charged with $CrCl_2$ (0.75 wt, 3.55 eq) and then heated to an internal temperature of 30° C. Reactor 2 was charged with triethylamine (0.62 wt, 3.55 eq) at a rate such that internal temperature did not exceed 45° C. After complete addition, an internal temperature of 30° C. was maintained for 1 hour. After 1 hour, reactor 2 was cooled to 0° C. and charged in an inert fashion with $NiCl_2$ (0.02 wt, 0.1 eq), followed by the contents of reactor 1 and the reaction was warmed to rt. Reactor 2 was cooled to an internal temperature of 0° C. and then ethylenediamine (1.2 vol, 10 eq) was added at a rate such that the internal temperature did not exceed 10° C. Note: An exotherm was observed. The reaction was stirred for 1 hour, and then water (8 vol) and n-heptane (20 vol) were added and the biphasic mixture stirred for 4 minutes and the layers allowed to partition. The organic layer was separated and the aqueous layer back extracted with MTBE (20 vol). The combined organic layers were concentrated in vacuo to a crude oil followed by an azeotrope with anhydrous THF (2×10.5 vol). The crude product was dissolved in anhydrous THF (4.5 vol) and then stored at −20° C. until utilization in the next stage.

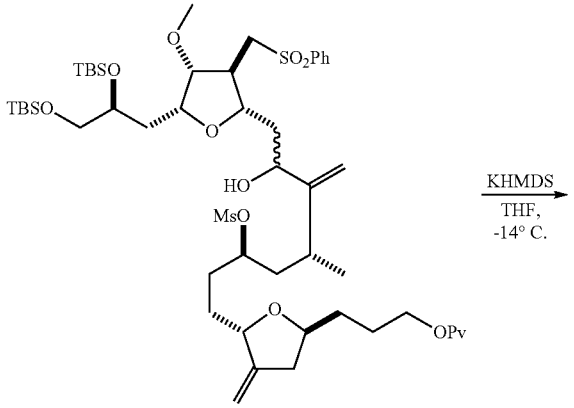

ER-808227

-continued

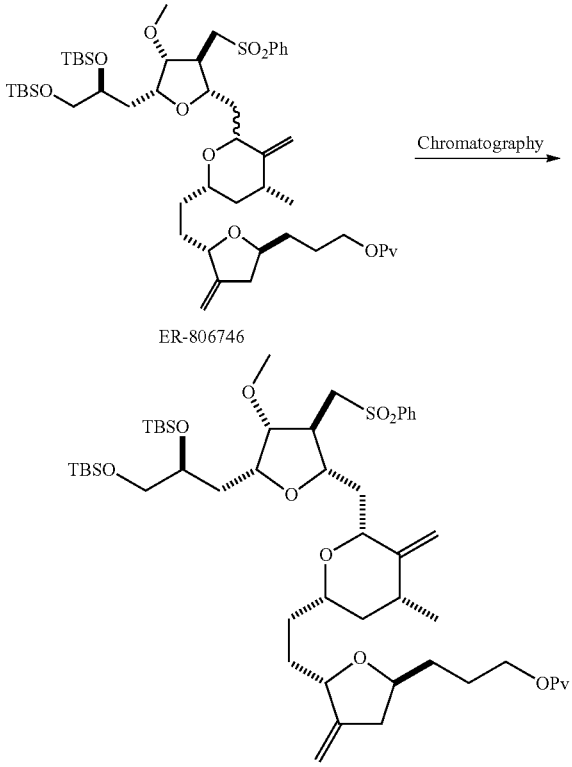

ER-806746

ER-804027

The ER-808227/THF solution from the previous step was analyzed via KF analysis. If KF <1000 ppm, then proceeded. If [KF 1000 ppm] *KF>1000 ppm*, azeotroped in vacuo with anhydrous THF (4.1 vol.). Repeated azeotrope until specification was met. The final solution meeting specifications contained the dissolved crude ER-808227 in anhydrous THF (4.1 vol.). Once the specification was met, an appropriately sized inerted reactor was charged with anhydrous THF (106 vol.) and the ER-808227/THF solution from the previous step. The reactor was cooled to an internal temperature of −15 to −20° C., then 0.5 M KHMDS in toluene (9.1 wt., 3.0 eq.) was added at a rate such that internal temperature did not exceed −12° C. Approximately 4.5 eq. KHMDS was necessary to drive the reaction to completion. The reaction was reverse quenched into semi-saturated ammonium chloride (40 vol.) at an internal temperature of 0° C. n-Heptane (80 vol.) was added, stirred for 2-5 minutes, and then allowed to partition. The organic layer was separated, the aqueous layer was back extracted with MTBE (70 vol.), then the organic layers were combined and washed with saturated sodium chloride solution (70 vol.). The organic layer was separated and concentrated in vacuo. To the crude concentrate was added n-heptane (60 vol.). Note: ER-807363 precipitated out of solution. The resulting suspension was filtered and the solids washed with n-heptane (20 vol.). The filtrate was concentrated in vacuo to afford crude ER-806746 (~4 wt.) as a brown oil[:]. Note: When additional ER-807363 precipitated out of solution, the filtration process was repeated. The crude ER-806746 was purified via $SiO_2$ column chromatography to yield ER-804027 (1.16 wt., 0.55 eq.) as a clear yellowish oil. The chromatography was performed as follows: the column was first flushed with sufficient MTBE to remove water then flushed with heptane to remove the MTBE. The ER-806746 was loaded onto the column as a solution in heptane then eluted from the column with heptane/MTBE (5:1) then heptane/MTBE (4:1) with the fractions monitored at 230 nm by UV detector.

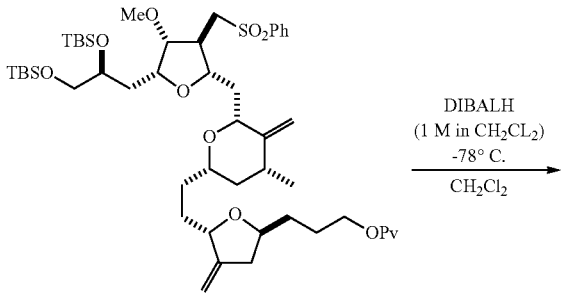

ER-804027

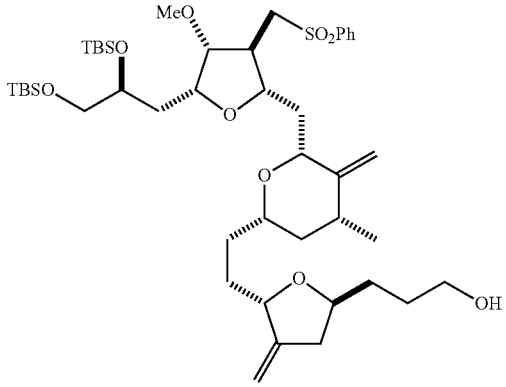

ER-804028

A reactor was charged with ER-804027 (1 wt, 1 eq) and anhydrous dichloromethane (7.6 vol). The reactor was cooled to an internal temperature of −78° C. and then 1 M DIBALH in dichloromethane (3.0 wt, 2.25 eq) was added at a rate such that internal temperature did not exceed −60° C. Methanol (0.1 vol) was added at a rate such that internal temperature did not exceed −60° C. Note: hydrogen gas evolved and was diluted with a stream of nitrogen. Upon complete addition, the mixture was warmed to ambient temperature and then 1 N hydrochloric acid (10.6 vol) and MTBE (25 vol) were added. The mixture was stirred for 20 minutes and the layers allowed to partition. The organic layer was separated and the aqueous layer *was* back extracted [layer] with MTBE (15.3 vol). The organic layers were combined and washed with water (3 vol), saturated sodium bicarbonate (3 vol), and saturated sodium chloride (3 vol), respectively, then concentrated in vacuo. The crude concentrate was purified via $SiO_2$ column chromatography to yield ER-804028 (0.84 wt, 0.93 eq) as a white foam.

C. Incorporation of F-3a and Transformations to B-1939

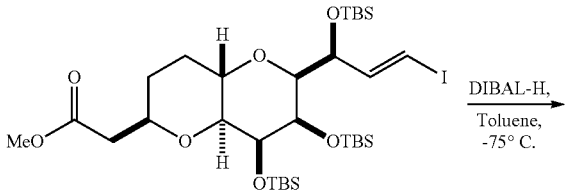

ER-803895

-continued

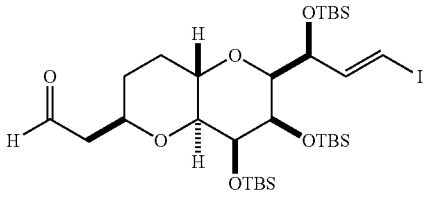

ER-803896

ER-803895 (F-3a) was dissolved in anhydrous toluene (14 wt.) and cooled to [←75° C.] <−*75° C.* under an argon atmosphere. DIBALH (1.5M in toluene, 0.95 wt., 1.3 eq.) was added at a rate to maintain the internal reaction temperature [←70° C.] <−*70° C.* The resulting mixture was stirred for 30 minutes then quenched with anhydrous methanol (0.13 wt., 3.2 eq.), maintaining the internal reaction temperature [←65° C.] <−*65° C.* The reaction mixture was allowed to warm to −10° C. and transferred with an MTBE rinse (3.74 wt.) to a workup vessel containing 1N HCl (10.2 wt.). The mixture was stirred for 30 minutes and the aqueous layer [is] *was* drained. The organic phase was washed sequentially with 1N HCl (10.2 wt.), water (10 wt.), saturated aqueous sodium bicarbonate (10 wt.), and brine (10 wt.) then concentrated under reduced pressure. The concentrate was purified via silica gel chromatography to afford ER-803896 (0.96 wt., 93% yield). The product is stored at −20° C. under argon.

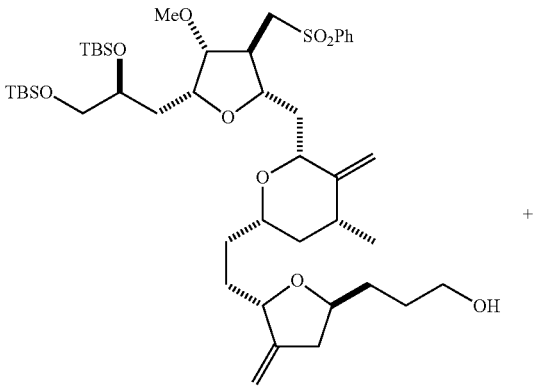

ER-804028

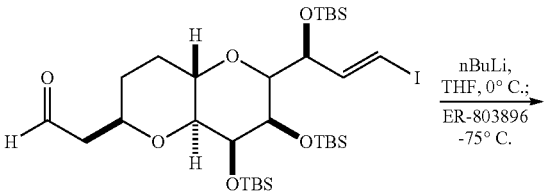

ER-803896

-continued

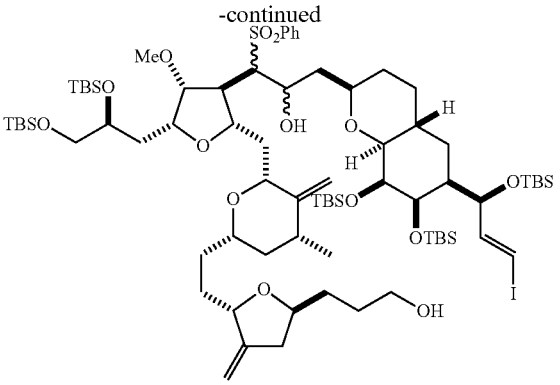

ER-804029

At 0° C., a solution of azeotropically dried sulfone ER-804028 (1.0 wt., 1 eq.) in anhydrous tetrahydrofuran (5 vol., 4.45 wt.) was treated with n-butyl lithium (1.6M in hexanes, 1.02 wt., 1.5 vol., 2.05 eq.) such that the internal temperature did not exceed 5° C. The mixture was stirred at internal temperature 0 to 5° C. for 10 minutes then cooled to [←75° C.] *<−75° C.* Azeotropically dried aldehyde ER-803896 (1.07 wt., 1.23 eq.) was dissolved in anhydrous hexanes (3.53 wt., 5.35 vol.) then cooled to [←75° C.] *<−75° C.* The aldehyde solution was added to the ER-804028 anion by cannula such that internal temperature ≤−65° C. The mixture was stirred for 45 minutes at internal temperature −78° C. then quenched by the addition of saturated ammonium chloride (5 vol.), methyl tert-butyl ether (10 vol.), and water (5 vol.). The aqueous layer was discarded and the organic layer concentrated under reduced pressure. The crude material was purified via C-18 reverse phase chromatography to afford ER-804029 (84%, 1.57 wt.).

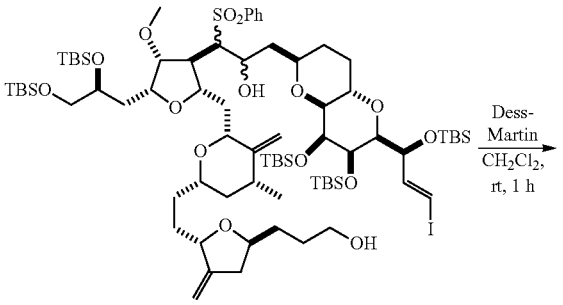

ER-804029

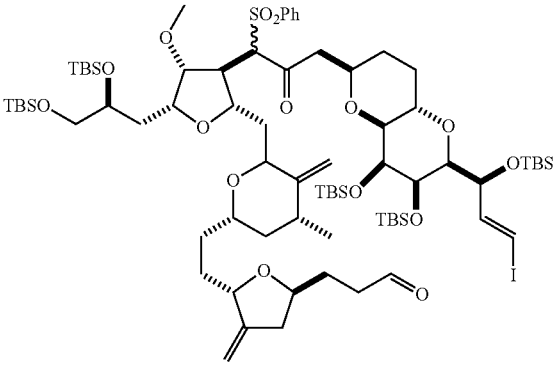

ER-804030

Sulfone-diol ER-804029 (1 wt., 1 eq.) was dissolved in wet dichloromethane (7.4 vol., 0.04 wt % water) and placed in a 20-25° C. water bath. Dess-Martin Reagent (0.67 wt., 2.5 eq.) was added in one portion. The reaction mixture was quenched with saturated sodium bicarbonate (10 vol) and 10 wt % aqueous sodium sulfite (10 vol.) and stirred for 30 minutes. The mixture was diluted with saturated sodium chloride (10 vol) and extracted with MTBE (25 vol). The aqueous layer was discarded and the organic layer concentrated and purified by silica gel chromatography to afford ER-804030 (0.9 wt., 90%). The material was stored under inert gas atmosphere at −20° C.

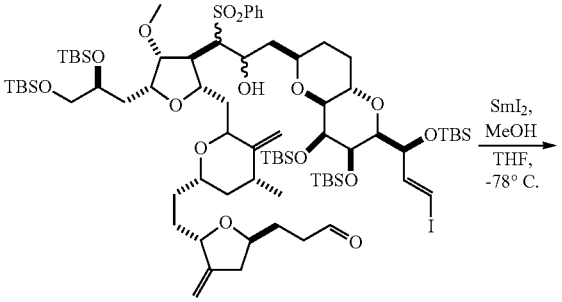

ER-804029

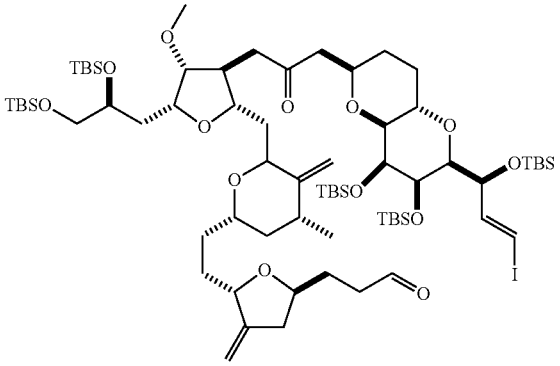

ER-118049

To a pre-dried reactor under inert atmosphere was charged samarium diiodide solution (2.5 eq.) and the solution cooled to internal temperature [←70° C.] *<−70° C.* ER-804030 (1 wt.) was dissolved in anhydrous methanol (4.1 wt.) and anhydrous THF (2.3 wt.) and then cooled to [←70° C.] *<−70° C.* ER-804030 was added to the cold samarium solution at a rate such that the internal temperature did not exceed −70° C. The reaction was quenched with potassium carbonate/Rochelle's Salts/water (1/10/100; w/w/v, 15 vol.) and MTBE (5 vol.) such that internal temperature did not exceed −65° C. Upon complete addition of the workup solution, the reaction was warmed to room temperature and the mixture transferred to a separatory vessel using the workup solution (20 vol. rinse) and MTBE (20 vol. rinse). The aqueous layer was discarded, the organic layer evaporated, and the residue purified via silica gel chromatography to afford ER-118049 (0.77 wt., 85%). The product was stored at −20° C. under inert atmosphere.

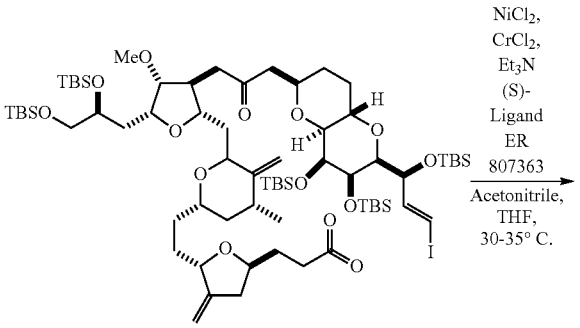

Keto Aldehyde ER-118049

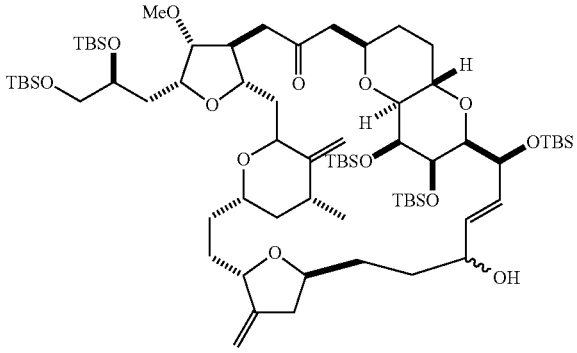

Allylic Alcohol ER-118047/048

A pre-dried reactor was charged with (S)-ligand ER-807363 (2.05 wt) and the atmosphere was exchanged for nitrogen. The $CrCl_2$ (0.85 wt, 10 eq) was added in one portion followed by anhydrous acetonitrile (21.5 wt) and the mixture was warmed and maintained between 30° C. to 35° C. Triethylamine (0.7 wt, 0.96 vol, 10 eq) was added in one portion and the mixture stirred for one hour. The $NiCl_2$ (0.09 wt, 1 eq) was added in one portion, followed by the keto-aldehyde ER-118049 in anhydrous THF (2.43 wt, 2.73 vol) over 30 minutes. The heat was removed then heptane (20.5 wt, 30 vol) and Celite® (1.5 wt) were added. The mixture was stirred for 5 minutes and filtered over a pad of Celite® (15 wt) and the Celite® pad rinsed with heptane (7.3 vol) and acetonitrile (5 vol). The filtrate was transferred to a separatory funnel and the lower layer removed. The combined heptane layers were washed with acetonitrile (maximum 47.2 wt, maximum 60 vol) as necessary. The heptane layer was evaporated under reduced pressure and the product purified by silica gel chromatography to afford ER-118047/048 (0.64 wt, 70%).

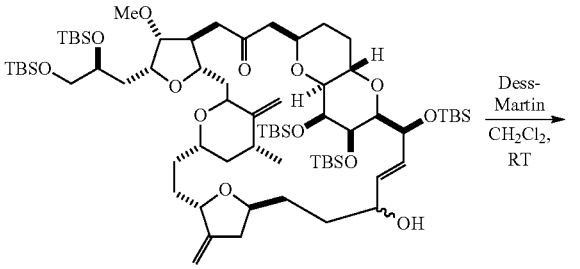

ER-118047/048

-continued

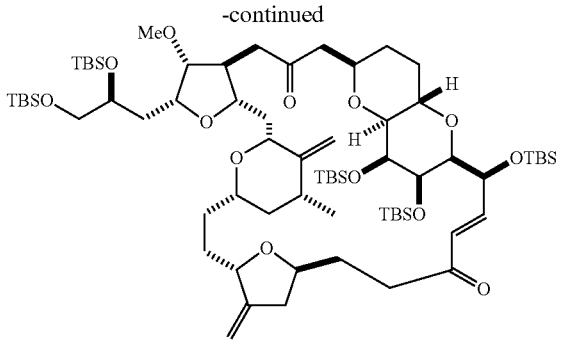

ER-118046

Allyl alcohol ER-118047/048 was dissolved in dichloromethane (0.04 wt % water, 9 vol) and the reactor was placed in a water bath (20° C.) and the solution was treated with Dess-Martin Reagent (0.48 wt, 1.5 eq). The reaction mixture was treated with saturated aqueous sodium bicarbonate (9 vol) and 10 wt % aqueous sodium sulfite (9 vol) then stirred for 20 minutes and transferred to a separatory funnel with DCM (10 vol). The aqueous layer was discarded, and the organic layer evaporated to a residue. The crude material was purified by flash chromatography (prepped with 3 CV (1:1 (V/V) DCM/heptane, the material was loaded with 1:1 DCM/heptane then eluted with 10/10/1 heptane/DCM/MTBE). The product-containing fractions were concentrated and stored under inert atmosphere at −20° C.

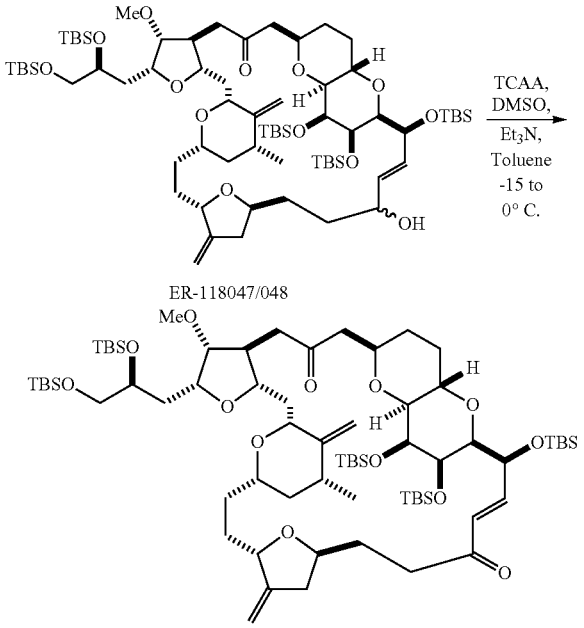

ER-118047/048

ER-118046

Alternatively, the oxidation of ER-118047/48 to form the di-ketone ER-118046 was accomplished as follows. A flask was charged with ER-118047/48 (1 wt, 1.0 eq) and toluene (10 vol) and DMSO (0.15 wts, 2.5 eq) were added at room temperature. $Et_3N$ (0.31 wts, 4.0 eq) was added and the solution was cooled to −15° C. TCAA (0.33 wts, 1.4 eq) was added neat and the reaction warmed to 0° C. then stirred for 10 minutes at 0° C. The reaction was stirred for additional 10 minutes then was quenched with IPA (0.15 vol). The reaction was stirred at 0° C. for 10 minutes. 1N HCl (5 vol) was added over 2 minutes, and the reaction was warmed to room temperature and diluted with MTBE (5 vol). Two clear layers formed and the aqueous layer was removed and discarded. The organic layer was washed with 5 vol of 5% bicarbonate (aqueous), concentrated to a heavy yellow oil on a rotary evaporator and purified by silica gel chromatography (91% isolated yield).

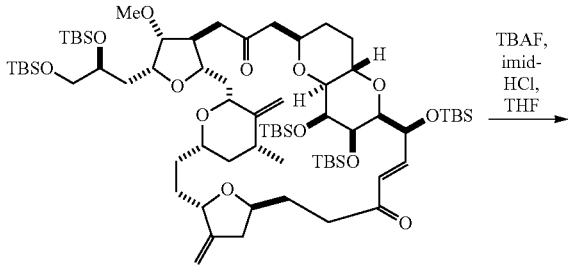

ER-118046

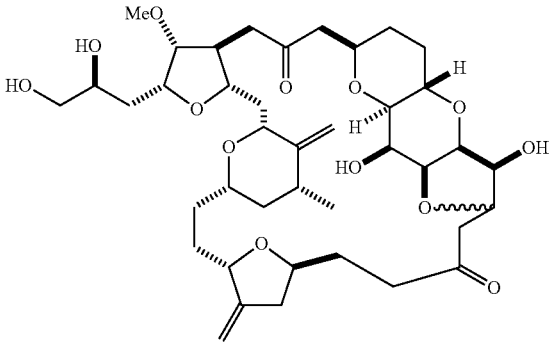

ER-118064

Into an appropriately sized reaction vessel (vessel A) was charged imidazole hydrochloride (0.39 wt, 5 eq) followed by 1 M TBAF in THF (7.6 vol, 10 eq) at ambient temperature. The resulting mixture was stirred until it is homogenous (15-30 minutes). Into a second reaction vessel (vessel B) was charged ER-118046 (1 wt, 1 eq) and THF (33 vol). The contents of vessel B were placed under an inert atmosphere and stirred until ER-118046 was fully dissolved. The contents of flask A (TBAF/Imidazole) were charged as a single portion into flask B (ER-118046/THF). After 3-4 days, the reaction solution was loaded onto a column and purified by silica gel chromatography.

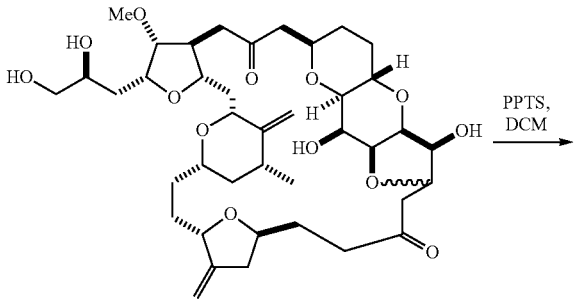

ER-118064

-continued

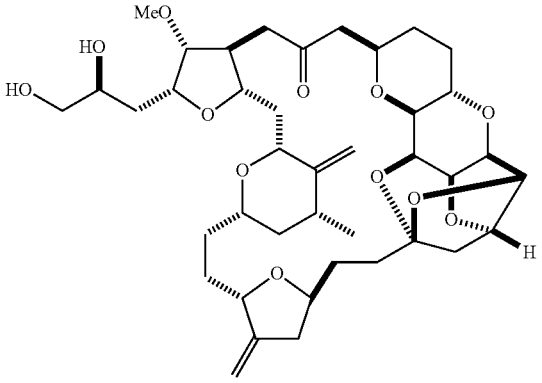

ER-076349

The dried ER-118064 (F-12 wherein $R^1$ is MeO) residue was dissolved in anhydrous dichloromethane (28 vol) under a nitrogen atmosphere and treated with PPTS (1.0 wt, 5.2 eq) in one portion. After 30-90 minutes, the reaction mixture was directly loaded atop an appropriate column and purified by silica gel chromatography. The desired fractions of ER-076349 were concentrated in vacuo. The material resulting from the concentration of all pure fractions was azeotroped twice from toluene (20 vol), affording ER-076349 as a crunchy colorless solid/foam (0.44 wt, 0.79 eq after correction for residual toluene).

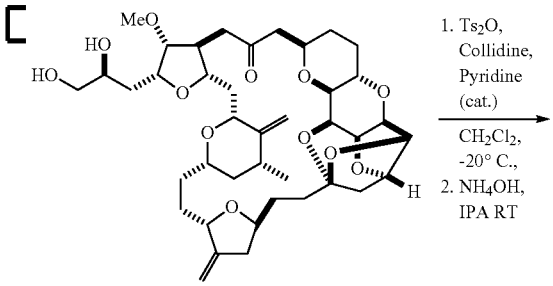

ER-076349

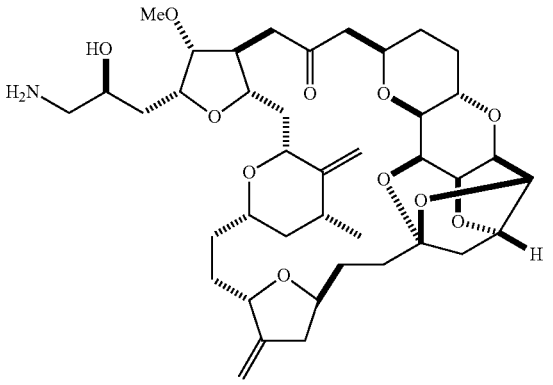

ER-086526

-continued

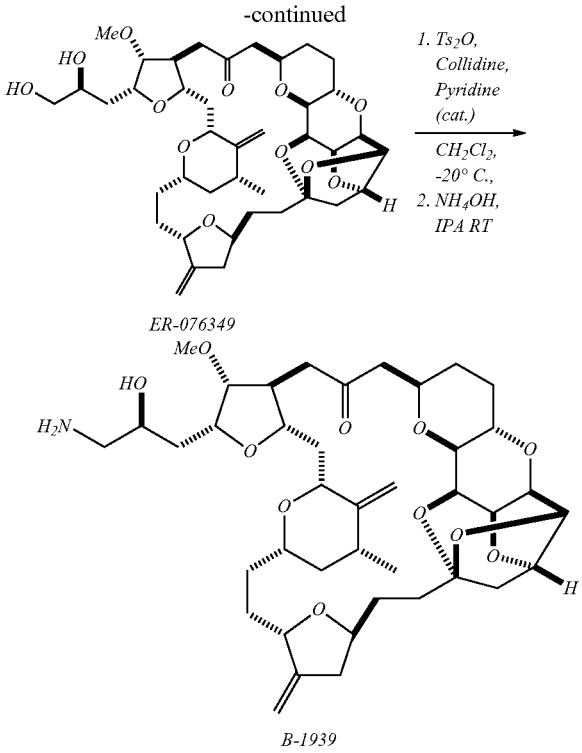

In a clean dry reaction vessel (flask C) ER-076349 (1 wt, 1 eq) was dissolved in anhydrous toluene (20 vol) and concentrated to dryness under reduced pressure. The substrate was re-dissolved in anhydrous toluene (20 vol) and concentrated to dryness. The substrate was dissolved in DCM (5 vol), and the solution placed under an argon atmosphere. Collidine (0.66 wts, 4.0 eq) was added as a single portion. Pyridine, as a solution in DCM (Flask B), was added as a single portion (5 mole %). The resulting mixture in flask C was cooled to an internal temperature of −20 to −25° C. A DCM solution of $Ts_2O$ was added drop-wise keeping the internal temperature below −16° C. (1.02 eq). The reaction was stirred at −20 to −25° C. for 80 minutes then warmed to 0° C. over 20 minutes and stirred for an additional 20 minutes. The reaction was quenched with water (2 vol). The bath was removed, and the reaction allowed to warm to room temperature (15-20° C.) and stirred (20 minutes). The reaction was rinsed to a larger vessel using the IPA (100 vol) and aqueous ammonium hydroxide (100 vol) was added to the reaction. The reaction was stirred at room temperature for 15-36 hours, monitoring for the disappearance of the tosylate (ER-082892) and epoxide (ER-809681) which formed in situ. The reaction was concentrated to dryness or near dryness at reduced pressure. The resulting material was diluted with DCM (25-40 vol) and washed pH 10 buffer ($NaHCO_3/Na_2CO_3$ (aq), 10 vol). The aqueous phase was back extracted with 25 vol of DCM and the combined organic layers were concentrated to dryness. The resulting free amine was purified by silica gel chromatography using a buffered ACN/water mobile phase. The pooled fractions were concentrated at reduced pressure to remove ACN. The resulting aqueous layer was diluted with DCM (40 vol) and with 30 vol of a pH 10 buffered stock solution ($NaHCO_3/Na_2CO_3$). The layers were mixed well and separated. The aqueous phase was back extracted with 25 vol of DCM and the combined organic layers were concentrated to dryness. The resulting free amine was polish filtered as a solution in 3:1 DCM/pentane and concentrated to dryness (0.80 wts) to afford B-1939.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

[1. A compound of formula F-4:

F-4

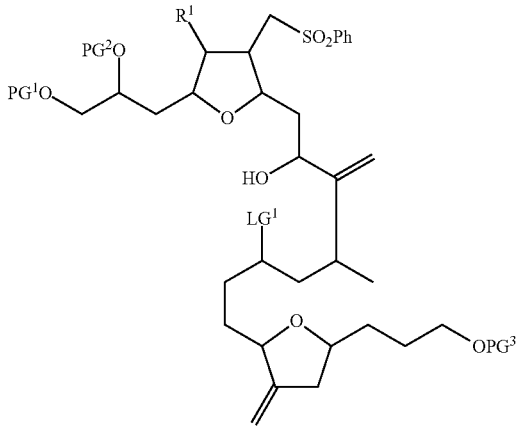

wherein:

each of $PG^1$, $PG^2$, and $PG^3$ is independently hydrogen or a suitable hydroxyl protecting group;

$R^1$ is R or —OR;

each R is independently hydrogen, $C_{1-4}$ haloaliphatic, benzyl, or $C_{1-4}$ aliphatic; and $LG^1$ is a suitable leaving group.]

[2. The compound according to claim 1, wherein said compound is of formula F-4':

F-4'

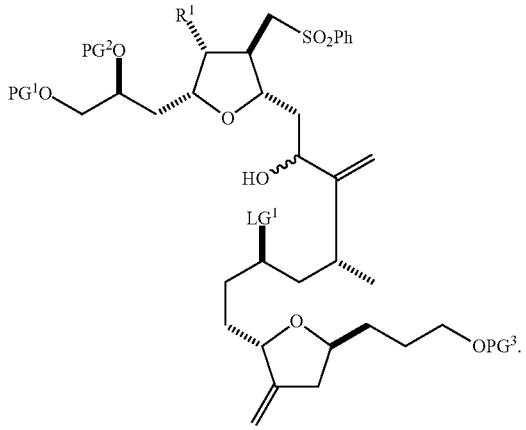

]

[3. The compound according to claim 2, wherein $R^1$ is OR wherein R is hydrogen, methyl, or benzyl.]

[4. The compound according to claim 2, wherein $PG^1$ and $PG^2$ are both hydrogen.]

[5. The compound according to claim 2, wherein each of $PG^1$ and $PG^2$ is independently a suitable hydroxyl protecting group.]

[6. The compound according to claim 5, wherein one or both of $PG^1$ and $PG^2$, taken together with the oxygen atom to which each is bound, is a silyl ether or an arylalkyl ether.]

[7. The compound according to claim 6, wherein $PG^1$ and $PG^2$ are both t-butyldimethylsilyl.]

[8. The compound according to claim 5, wherein $PG^1$ and $PG^2$ are taken together, with the oxygen atoms to which they are bound, to form a diol protecting group.]

[9. The compound according to claim 8, wherein said diol protecting group is a cyclic acetal or ketal, a silylene derivative, a cyclic carbonate, or a cyclic boronate.]

[10. The compound according to claim 2, wherein $LG^1$ is sulphonyloxy, optionally substituted alkylsulphonyloxy, optionally substituted alkenylsulfonyloxy, optionally substituted arylsulfonyloxy, or halogen.]

[11. The compound according to claim 10, wherein $LG^1$ is mesyloxy tosyloxy, chloro, iodo, bromo, or triflate.]

[12. The compound according to claim 2, wherein said compound is:

F-4a

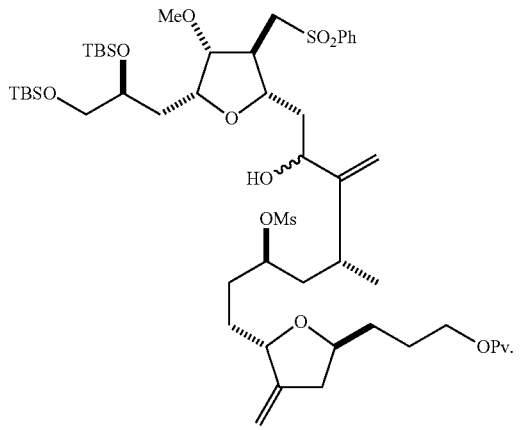

]

[13. The compound according to claim 1, wherein said suitable hydroxyl protecting group, taken with the oxygen atom to which it is bound, is selected from an ester, an ether, a silyl ether, an alkyl ether, an arylalkyl ether, and an alkoxyalkyl ether.]

[14. The compound according to claim 13, wherein
said ester is a formate, acetate, carbonate, or sulfonate;
said silyl ether is a trialkylsilyl ether; or
said alkoxyalkyl ether is an acetal.]

[15. The compound according to claim 13, wherein said ester is formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetyl), crotonate, 4-methoxy-crotonate, benzoate, p-benzylbenzoate, 2,4,6-trimethylbenzoate, methyl carbonate, 9-fluorenylmethyl carbonate, ethyl carbonate, 2,2,2-trichloroethyl carbonate, 2-(trimethylsilyl)ethyl carbonate, 2-(phenylsulfonyl)ethyl carbonate, vinyl carbonate, ally! carbonate, or p-nitrobenzyl carbonate;

said silyl ether is trimethylsilyl, triethylsilyl, t-butyldimethylsilyl, t-butyldiphenylsilyl, or triisopropylsilyl ether;

said alkyl ether is methyl, trityl, t-butyl, allyl, or allyloxycarbonyl ether;

said alkoxyalkyl ether is methoxymethyl, methylthiomethyl, (2-methoxyethoxy)methyl, benzyloxymethyl, beta-(trimethylsilyl)ethoxymethyl, and tetrahydropyranyl ethers; or said arylalkyl ether is benzyl, p-methoxybenzyl (MPM), 3,4-dimethoxybenzyl, o-nitrobenzyl, p-nitrobenzyl, p-halobenzyl, 2,6-dichlorobenzyl, p-cyanobenzyl, 2- picolyl, or 4-picolyl.]

[16. The compound according to claim 1, wherein $LG^1$ is mesyloxy or tosyloxy.]

[17. The compound according to claim 9, wherein said cyclic acetal or ketal is methylene, ethylidene, benzylidene, isopropylidene, cyclohexylidene, or cyclopentylidene; or said silylene derivative is di-t-butylsilylene or a 1,1,3,3-tetraisopropyldisiloxanylidene derivative.]

[18. The compound according to claim 1, wherein $LG^1$ is sulphonyloxy, optionally substituted alkylsulphonyloxy, optionally substituted alkenylsulfonyloxy, optionally substituted arylsulfonyloxy, or halogen.]

*19. A compound of formula:*

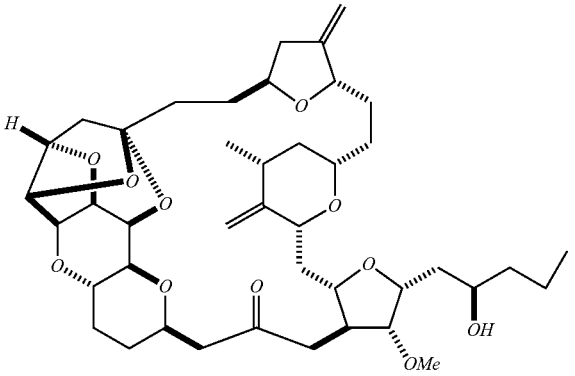

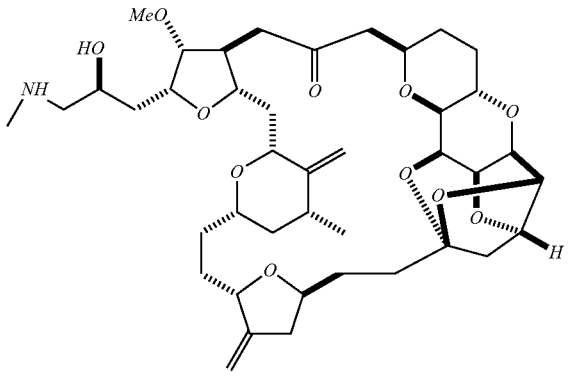

*and/or a pharmaceutically acceptable salt thereof.*

*20. A composition comprising a compound:*
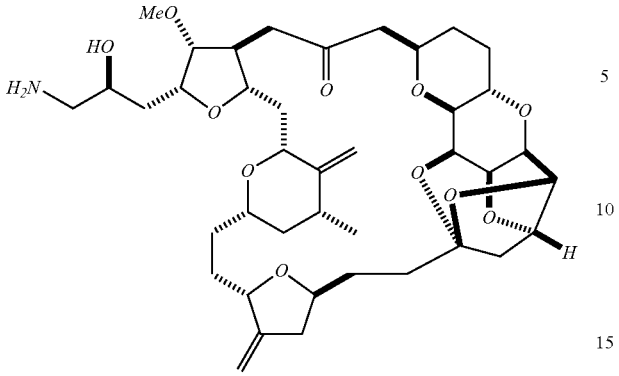
*and/or a pharmaceutically acceptable salt thereof, and a compound of formula:*
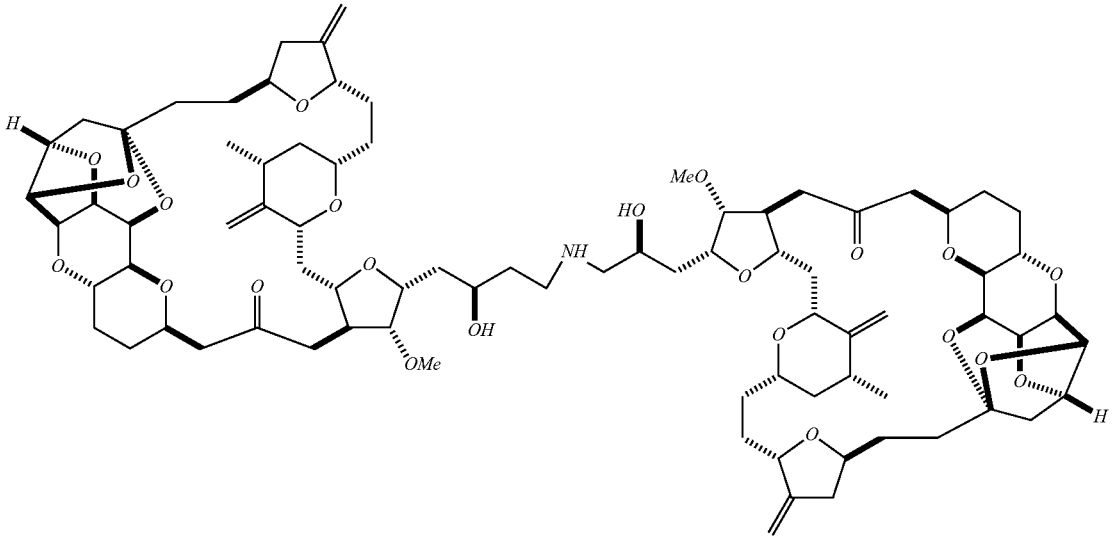
*and/or a pharmaceutically acceptable salt thereof.*
* * * * *